(12) United States Patent
Haddleton et al.

(10) Patent No.: US 9,200,104 B2
(45) Date of Patent: Dec. 1, 2015

(54) POLYMER

(71) Applicant: Warwick Effect Polymers Limited, Coventry (GB)

(72) Inventors: David M. Haddleton, Kenilworth (GB); Francois LeColley, Trivieres (BE); Lei Tao, Coventry (GB); Giuseppe Mantovani, Coventry (GB); Adrian Carmichael, Coventry (GB); Adam Peter Jarvis, Coventry (GB); Andrew Gregory Steward, Cubbington (GB)

(73) Assignee: Warwick Effect Polymers Limited, Coventry (GB)

( * ) Notice: Subject to any disclaimer, the term of this patent is extended or adjusted under 35 U.S.C. 154(b) by 150 days.

(21) Appl. No.: 13/857,513

(22) Filed: Apr. 5, 2013

(65) Prior Publication Data

US 2013/0295040 A1 Nov. 7, 2013

Related U.S. Application Data

(63) Continuation of application No. 11/498,525, filed on Aug. 3, 2006, now Pat. No. 8,436,104, and a continuation of application No. 11/311,922, filed on Dec. 19, 2005, now abandoned, and a continuation of application No. PCT/GB2004/002894, filed on Jul. 6, 2004, and a continuation-in-part of application No. PCT/GB2004/002608, filed on Jun. 18, 2004.

(30) Foreign Application Priority Data

Jun. 20, 2003 (GB) .................... 0314472.2

(51) Int. Cl.
| | | |
|---|---|---|
| *A61K 47/48* | (2006.01) | |
| *C07D 207/404* | (2006.01) | |
| *C07D 209/48* | (2006.01) | |
| *C08F 2/38* | (2006.01) | |
| *C08F 290/06* | (2006.01) | |
| *C08F 4/00* | (2006.01) | |
| *C08F 299/02* | (2006.01) | |
| *C07D 207/452* | (2006.01) | |
| *C07D 213/70* | (2006.01) | |
| *C07D 233/54* | (2006.01) | |
| *C07D 249/18* | (2006.01) | |
| *C07D 251/26* | (2006.01) | |
| *C07D 251/42* | (2006.01) | |
| *C08F 293/00* | (2006.01) | |

(52) U.S. Cl.
CPC ....... *C08F 299/024* (2013.01); *A61K 47/48176* (2013.01); *A61K 47/48215* (2013.01); *C07D 207/404* (2013.01); *C07D 207/452* (2013.01); *C07D 209/48* (2013.01); *C07D 213/70* (2013.01); *C07D 233/54* (2013.01); *C07D 249/18* (2013.01); *C07D 251/26* (2013.01); *C07D 251/42* (2013.01); *C08F 4/00* (2013.01); *C08F 290/062* (2013.01); *C08F 293/005* (2013.01); *C08F 299/022* (2013.01); *C08F 2438/01* (2013.01)

(58) Field of Classification Search
CPC .................. A61K 7/48176; A61K 47/48215; C08F 290/062; C08F 293/005; C08F 299/022; C08F 299/024; C08F 4/00; C08F 116/20; C08F 216/1416; C08F 2216/1425; C08F 2216/1433; C08F 2216/1441
USPC ................ 424/78.27; 526/89, 320, 332, 334; 525/54.1, 54.2, 167, 328.9, 330.3, 374, 525/383
See application file for complete search history.

(56) References Cited

FOREIGN PATENT DOCUMENTS

WO WO-03062290 A1 * 7/2003

OTHER PUBLICATIONS

Wang, X.S. et al. Macromolecules vol. 33 pp. 6640-6647 published online Aug. 2000.*
Haddleton, D.M. et al, Macromolecules vol. 32 pp. 8732-8739 published online Dec. 1999.*

* cited by examiner

*Primary Examiner* — Irina S Zemel
*Assistant Examiner* — Jeffrey Lenihan
(74) *Attorney, Agent, or Firm* — Edgar W. Harlan; Carolyn S. Elmore, Esq.; Elmore Patent Law Group, P.C.

(57) ABSTRACT

The application provides a method of producing a comb polymer comprising the steps of:
(a) Providing:
(i) a plurality of monomers which are linear, branched or star-shaped, substituted or non-substituted, and have an olefinically unsaturated moiety, the olefinically unsaturated moiety being capable of undergoing addition polymerisation;
(ii) an initiator compound; the initiator compound comprising a homolytically cleavable bond.
(iii) a catalyst capable of catalysing the polymerisation of the monomer; and
(b) Causing the catalyst to catalyse, in combination with the initiator, the polymerisation of a plurality of the monomers to produce the comb polymer.
Catalysts and polymers obtainable by the process are also provided.
Preferably, the comb polymer is capable of binding proteins and may be produced from monomers which are alkoxy polyethers, such as poly(alkyleneglycol) or polytetrahydrofuran.

19 Claims, 34 Drawing Sheets

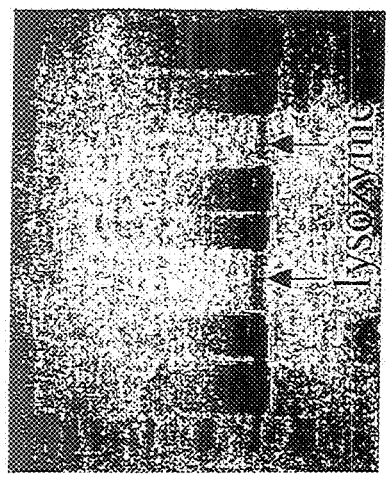
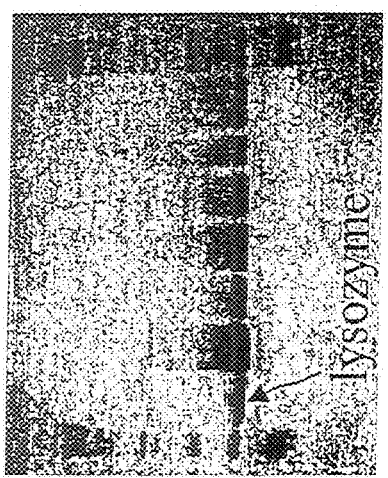
FIG. 32

POLYMER

RELATED APPLICATION(S)

This application is a continuation of U.S. application Ser. No. 11/498,525, filed Aug. 3, 2006, which is a continuation of U.S. application Ser. No. 11/311,922, filed Dec. 19, 2005 (Abandoned), which is a continuation of International Application No. PCT/GB2004/002894, which designated the United States and was filed on Jul. 6, 2004, published in English, which is a continuation-in-part of International Application No. PCT/GB2004/002608, which designated the United States and was filed on Jun. 18, 2004, published in English. This application claims priority under 35 U.S.C. §119 or 365 to Great Britain, Application No. GB0314472.2, filed Jun. 20, 2003. The entire teachings of the above applications are incorporated herein by reference.

The invention relates to processes of making comb polymers from monomers comprising alkoxy polyethers, such as polyalkylene glycol such as poly (ethylene glycol), or polytetrahydrofuran (PTHF). Such methods may include the use of an initiator compound which comprises a moiety which, wizen attached to the comb polymer, is capable of binding to a protein or polypeptide. The initiator compounds and finished comb polymers, and their uses, are also included within the invention.

The modification of proteins with polymers such as poly (ethylene glycol), which is known by the abbreviation PEG, is well-known in the art. PEG-derivatives are manufactured, for example, by Shearwater Corporation, Huntsville, Ala., USA, and Enzon, Inc., Bridgewater, N.J., USA. Uses of PEG are reviewed in catalogues from both of those companies, and indeed in the 2002 Enzon, Inc. Annual Report.

The attachment of PEG to proteins or polypeptides, known as PEGylation has been found to have a number of benefits. Firstly, this reduces the antigenicity and immunogenicity of a molecule to which PEG is attached. PEG also produces markably improved circulating half-lives in viva due to either evasion of renal clearance as a result of the polymer increasing the apparent size of the molecule to above the glomerular filtration limit, and/or through evasion of cellular clearance mechanisms. PEG can markably improve the solubility of proteins and polypeptides to which it is attached, for example PEG has been found to be soluble in many different solvents, ranging from water to many organic solvents such as toluene, methylene chloride, ethanol and acetone. An application of this has been to use PEG-modified antibodies, for example to phase partition target molecules or cells. PEGylation has also been found to enhance proteolytic resistance of the conjugated protein, and improve bioavailability via reduced losses at subcutaneous injection sites. PEGylation also has been observed to reduce the toxicity of the proteins or polypeptides to which it is attached, improve thermal and mechanical stability of the molecules and allow the improved formulation into materials used for some slow release administration strategies. These advantages are reviewed in, for example, the articles by Chapman A. P. (Advanced Drug Delivery Reviews, Vol. 54 (2002), pages: 531-545). The chemistry of polypeptide and protein PEGylation is further reviewed in the article by Roberts, M. J., et al, (Advanced Drug Delivery Reviews, Vol. 54 (2002), pages 459-476), and the article by Kinstler, O., et al. (Advanced Drug Delivery Reviews, Vol. 54 (2002), pages 477.485).

A number of PEGylated drags are on the market, For example. PEG-INTRON™ is an α-interferon product produced by Schering-Plough and Enzon, Inc. which is used to treat hepatitis C and cancer. Prothecan™ is a PEG-enhanced version of camptothecin, topoisomerase I inhibitor that is effective against some cancers, PEGylated taxol and several enzyme-based products have also been produced which show, for example, better uptake in tumours and reduced side-effects compared to non-PEGylated compounds. As discussed in the review by Roberts (Supra), polymers such as PEG may be attached via a number of reactive amino acids on protein or polypeptide molecules, including lysine, cysteine, histidine, arginine, aspartic acid, glutamic acid, serine, threonine, tyrosine, N-terminal amino groups and C-terminal carboxylic acid groups. In the ease of glycoproteins, vicinal hydroxyl groups can be oxidised with periodate to form two reactive formyl moieties. A wide range of functional groups may be attached to compounds such as PEG to allow them to attach to lysine amine groups and N-terminal amine groups. These include succinimidyl succinate, hydroxysuccinamide and hydroxysuccinamide esters, aldehyde derivatives such as propionaldehyde and acetaldehyde, propionate and buterwate derivatives of succinimidyl, benzotriazole carbonate, ρ-nitrophenyl carbonate, trichlorophenyl carbonate and carbonylimidazole. Compounds such as tresylate are known to bind to proteins via nucleophilic attack. There are also a number of compounds which can react with cysteine residues on proteins or polypeptides. These include maleimides, vinylsulphones, pyridyl sulphides and iodoacetamides. Furthermore, succinimidyl carbonate can also be used as a functionalised group to attach PEG or other polymers to alanine or histidine amino acids within a protein or polypeptide. As already indicated, the reaction of such functionalised groups is already well-characterised as indicated in the articles by Roberts, Kinsler and Chapman, and indeed as shown in, for example, the Shearwater Catalogue (2001).

The PEG currently on the market is usually in the form of long poly (ethylene glycol) polymers or branched or star-shaped poly (ethylene glycols).

The Applicants have now identified that it is possible to produce comb polymers which allow the size of the polymer attached to biological substances, for example, proteins and polypeptides, nucleic acids (DNA and RNA), carbohydrates and fats, to be varied and to be controlled. This allows the possibility of producing a wide variety of different polymers for attaching to proteins and polypeptides, which may be varied in their size and hydrodynamic volume to vary the properties of the compound to which the polymer is attached. For example, this may be used to vary the stability, solubility, toxicity and/or drug retention time of a drug which has been covalently attached to such co-polymers. Such co-polymers are capable of being produced in, a controlled manner by so-called living radical polymerisation.

Living radical polymerisation is subject of International Patent Application No. WO 97/47661. Supported polymerisation catalysts and specific polymerisation initiators are also shown in WO 99/28352 and WO 01/94424. Basically, the system uses a compound complexed with a transition metal. This compound is preferably an organodiimine, although one of the nitrogens of the diimine, is preferably not part of an aromatic ring (e.g. a 1,4-diaza-1,3-butadiene, a 2-pyridinecarbaldehyde imine, an oxazolidone or a quinoline carbaldehyde).

Living free radical systems, which involve the use of free radical initiators are also known, see for example WO 96/30421 and WO 97/18247. This is reviewed in Kamigaito, et al., Chem. Rev. (2001), Vol. 12, pages 3689-3745.

A combination of the catalyst and the initiators has in the past been used to polymerise un-saturated monomers, such as vinylic monomers. The inventors have now realised that these systems may be used to produce comb polymers in a controlled manner. These comb polymers may have a functional group attached to them via conventional chemistry. However, the inventors have also realised that the initiators used in living radical polymerisation are attached to the comb polymer as a result of the reaction of the initiator with the monomers. This means that it is possible to functionalise the comb polymer at the same time as producing the co-polymer, by using a functionalised initiator.

Accordingly, the first aspect of the invention provides a method of producing a comb polymer comprising the steps of:
(a) Providing:
  (i) a plurality of monomers which are linear, branched or star-shaped, substituted or non-substituted, preferably containing 2, especially from 3 to 10, carbon atoms, and have an olefinically unsaturated moiety attached thereto, the olefinically unsaturated moiety being capable of undergoing addition polymerisation;
  (ii) an initiator compound; the initiator compound comprising as homolytically cleavable bond;
  (iii) a catalyst capable of catalysing the polymerisation of the monomer; and
(b) Causing the catalyst to catalyse, in combination with the initiator, the polymerisation of a plurality of the monomers to produce the comb polymer;
wherein the initiator compound (ii) comprises a moiety which, when attached to the comb polymer, is capable of binding to a biological substance.

The monomers in (i) are preferably alkoxy polyethers such as poly (alkylene glycol) or polytetrahydrofuran.

The comb polymer may have a moiety which, when attached to the comb polymer, is capable of binding e.g. a protein or polypeptide, attached to it using conventional chemistry. However, as already indicated, it is possible to produce initiator compounds which have that moiety attached to them. Therefore, preferably the initiator compound comprises a moiety which, when attached to a comb polymer, is capable of binding to a biological substance, such as a protein or polypeptide, nucleic acid (DNA or RNA), carbohydrates or fats.

Preferably, the poly (alkylene glycol) is a polymer of an alkylene glycol containing from 2-10, especially at least 3, carbon atoms, most preferably poly (ethylene glycol), of (propylene glycol) or poly (butylene glycol). For example, poly (ethylene glycol) may be used.

In its most common form, this is a linear or branched polyether terminated with hydroxyl groups. This is synthesised by anionic ring opening polymerisation of ethylene oxide initiated by nucleophilic attack of a hydroxide ion on the epoxide ring. It is also possible to modify polyethylene glycol, for example by placing a monomethoxy group on one end to produce monomethoxy PEG (mPEG). This is synthesised by an ionic ring opening polymerisation initiated with methoxide ions and is commercially available. However, trace amounts of water present in the reaction mixture causes the production of significant quantities of PEG which is terminated at both ends by hydroxy groups. This is undesirable, as the moiety capable of binding to proteins or peptides will then attach to both ends of the polymer chain, which will cause unwanted crosslinking of proteins in the body.

A method intended to minimise the production of this impurity is to initiate the ring opening of ethylene oxide by nucleophilic attack of a benzoxy ion on the epoxide ring. In a similar manner to the above process, monobenzoxy PEG is produced, as well as the PEG chain terminated at both ends by hydroxy. This mixture is methylated, producing one chain terminated with BzO and OMe, and dimethoxy PEG. Hydrogenation of this mixture eliminates the benzoxy group to yield mPEG and dimethoxy PEG, Dimethoxy PEG remains present as an inert impurity. However, even using this process, the product obtained still contains 5-10% of the unwanted dihydroxy PEG according to its certificate of analysis.

The process of the present invention yields a product which is substantially 100% pure, eliminating substantially all of the dihydroxy PEG impurity, thus avoiding the disadvantages of the known processes, and removing the possibility of the cross-linking of proteins.

Branched and star-shaped polymers such as PEG are available from a number of commercial sources, such as Enzon and Shearwater. Polytetrahydrofurans may also be obtained from commercial sources, such as Aldrich (Gillingham, Dorset, UK.).

Preferably, the molecular weight of the PEGmethacrylate is 475, 1100, 2080, 5000 or 20,000.

The polyalkylene glycol and polytetrahydrofuran comprises an olefinically unsaturated moiety, for example at the end of the polymer chain. This olefinically unsaturated moiety is capable of undergoing additional polymerisation.

The olefinically unsaturated monomer may be a methacrylate, an acrylate, a styrene, methacrylonitrile or a diene such as butadiene.

Examples of olefinically unsaturated moieties that may be used include methyl methacrylate, ethyl methacrylate, propyl methacrylate (all isomers), butyl methacrylate isomers), and other alkyl methacrylates; corresponding acrylates; also functionalised methacrylates and acrylates including glycidyl methacrylate, trimethoxysilyl propyl methacrylate, allyl methacrylate, hydroxyethyl methacrylate, hydroxypropyl methacrylate, dialkylaminoalkyl methacrylates such as dimethylethylamino methacrylate; fluoroalkyl (meth)acrylates; methacrylic acid, acrylic acid; fumaric acid (and esters), itaconic acid (and esters), maleic anhydride: styrene, α-methyl styrene; vinyl halides such as vinyl chloride and vinyl fluoride; acrylonitrile, methacrylonitrile; glycerol; vinylidene halides of formula $CH_2=C(Hal)_2$ where each halogen is independently Cl or F; optionally substituted butadienes of the formula $CH_2=C(R^{15})C(R^{15})=CH_2$ where $R^{15}$ is independently H. C1 to C10 alkyl, Cl, or F; sulphonic acids or derivatives thereof of formula $CH_2=CHSO_2OM$ wherein M is Na, K, Li, $N(R^{16})_4$, where each $R^{16}$ is independently H or $C_1$ to $C_{10}$ alkyl, COZ, ON, $N(R^{16})_2$ or $SO_2OZ$ and Z is H, Li, Na, K or $N(R^{14})_4$; acrylamide or derivatives thereof of formula $CH_2CHCON(R^{16})_2$ and methacrylamide or derivative thereof of formula $CH_2=C(CH_3)CON(R^{16})_2$.

Mixtures of such monomers may be used.

Such unsaturated moieties may be attached, for example, at an end of the polymer, by conventional chemistry. Alternatively, such monomers may be obtained commercially. For example, PEGacrylate, diacrylate, methacrylate and dimethacrylate are commercially available from Aldrich (Gillingham, Dorset, UK.).

The unsaturated moiety may be attached to the polyalkylene glycol or polytetrahydrofuran by means of any suitable linkage groups, for example via a methyl ether linkage. Hence, it is possible to use poly (ethylene glycol) methyl ether methacrylate (available from Aldrich Chemicals). One advantage of using the living radical polymerisation technique is that commercially available compounds such as this, which have free-radical inhibitors, such as hydroquinones, may be used without further purification. With conventional free-radical-based systems the presence of a free-radical inhibitor will inhibit the addition polymerisation reaction. This is not the case with living radical polymerisation.

The initiator compound may comprise a homolytically cleavable bond with a halogen atom. This may contain a bond that breaks without integral charge formation on either atom by homolytic fission. As described in WO 97/01589, WO 99/28352 and WO 01/94424, it is believed that true free-radicals do not appear to be formed using some catalysts. It is believed that this occurs in a concerted fashion whereby the monomer is inserted into the bond without formation of a discrete free-radical species in the system. That is, during propagation this results in the formation of a new carbon-carbon bond and a new carbon-halogen bond without free-radical formation. A free-radical which is an atom or group of atoms having an unpaired valance electron and which is a separate entity without interactions, is not produced by the interaction of the initiator compound with the monomer with which it interacts.

Suitable initiator compounds are described in, for example, WO 97/47661. However, it is preferable that the initiator compound also comprises a moiety which, when attached to the comb polymer, is capable of binding to a protein or polypeptide. These moieties are known in the art, as indeed described in Roberts, et al. (Supra), Chapman (Supra) and, for example, in the catalogues of Enzon and Shearwater.

The initiator may be a thioester or xanthate. These are used in so called RAFT (Reversible Addition Fragmentation chain transfer and nitric oxide mediated polymerisation) and MADIX catalysation. The initiators and their reactions are described in WO 99/31144, WO 98/01478 and U.S. Pat. No. 6,053,705.

Preferably, the initiator compound (ii) is selected from
A-S—C(O)—R, A-S—C(S)—O—R, R—S—C(O)-A, R—S—C—(S)—O-A, when R is $C_1$ to $C_{20}$ substituted or loon-substituted, straight chain, branched chain, cyclic, heterocyclic or aromatic alkyl;

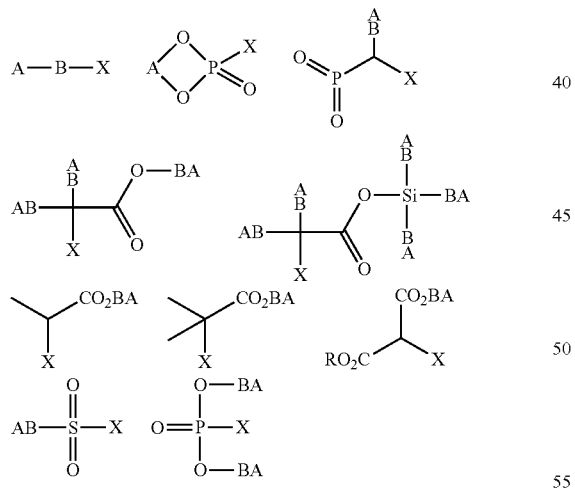

where: X=a halide, especially Cl or Br,
A a moiety which, when attached to the comb polymer, is capable of binding to a protein or polypeptide,
B is a linker and may or may not be present.

A is preferably selected from succinimidyl succinate, N-hydroxy succimimide, succinimidyl propionate, succinimidyl butanoate, propionaldehyde, acetaldehyde, tresylate, triazine, vinylsulfone, benzotriazole carbonate, maleimide, pyridyl sulfide, iodoacetamide and succinimidyl carbonate.

The linker is preferably selected from a $C_1$ to $C_{20}$ substituted or non-substituted, straight chain, branched chain cyclic, heterocyclic or aromatic alkyl group; —$(CH_2Z)_a$ $CH_2$—, —$CH_2ZCH_2$—, —$(CH_2CH_2Z)_n$—R, —$(CH_2CH(CH_3Z)_n$—R, —$(CH_2)_b$—C(O)—NH—$(CH_2)_c$—, —$(CH_2)_a$—NH—C(O)—$(CH_2)_y$—, —N(H)$_2$—; —S—; —N—R; or —O—R; where R=$C_1$ to $C_{20}$ substituted or non-substituted, straight chain, branched chain cyclic, heterocyclic or aromatic alkyl, Z is O or S, and n, a, b and c are independently selectable integers between 1 and 10. Preferably, the linker contains 1, 2, 3, 4, 5, 6, 7, 8, 9 or 10 carbon atoms. Most preferably, the linker is methyl, ethyl, propyl, butyl or pentyl.

Preferably, the moiety which is capable of reacting with the protein or polypeptide has the formula:

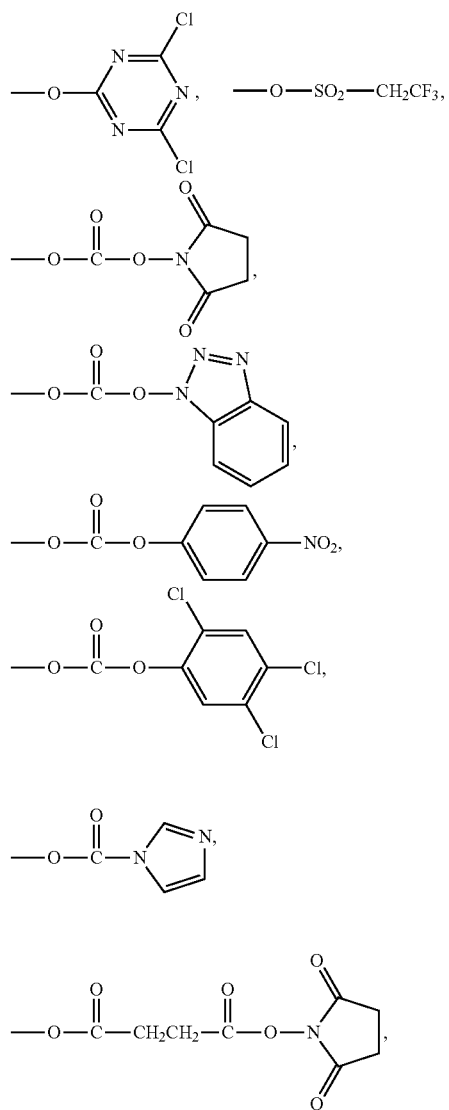

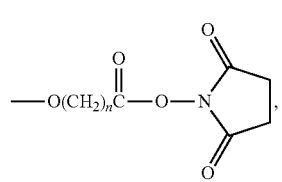

where n=integer of 0 to 10

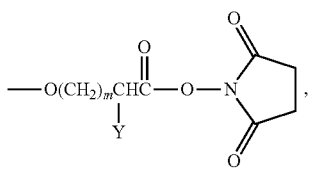

where m=integer of 0 to 10, Y is an aliphatic or aromatic moiety

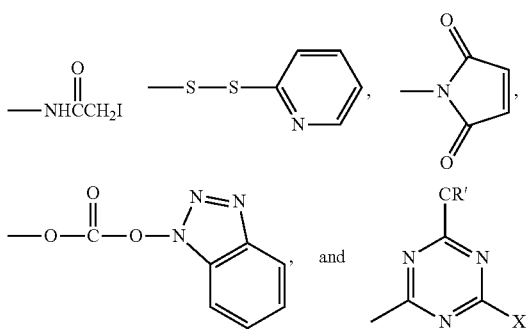

where R' is H, methyl, ethyl, propyl or but X is a halide, especially Cl or Br.

Most preferably, the initiator (ii) has a formula:

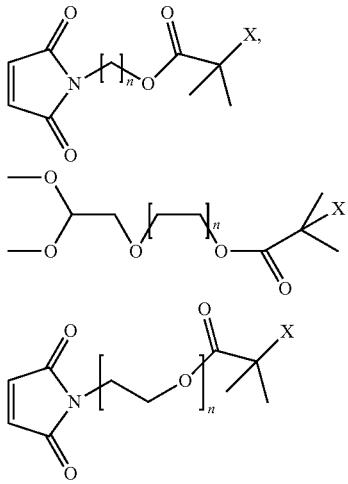

where n is an integer of 0 to 10, and X is a halide, especially Cl or Br.

The initiator has a compound selected from

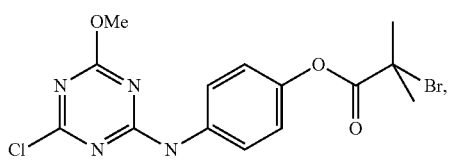

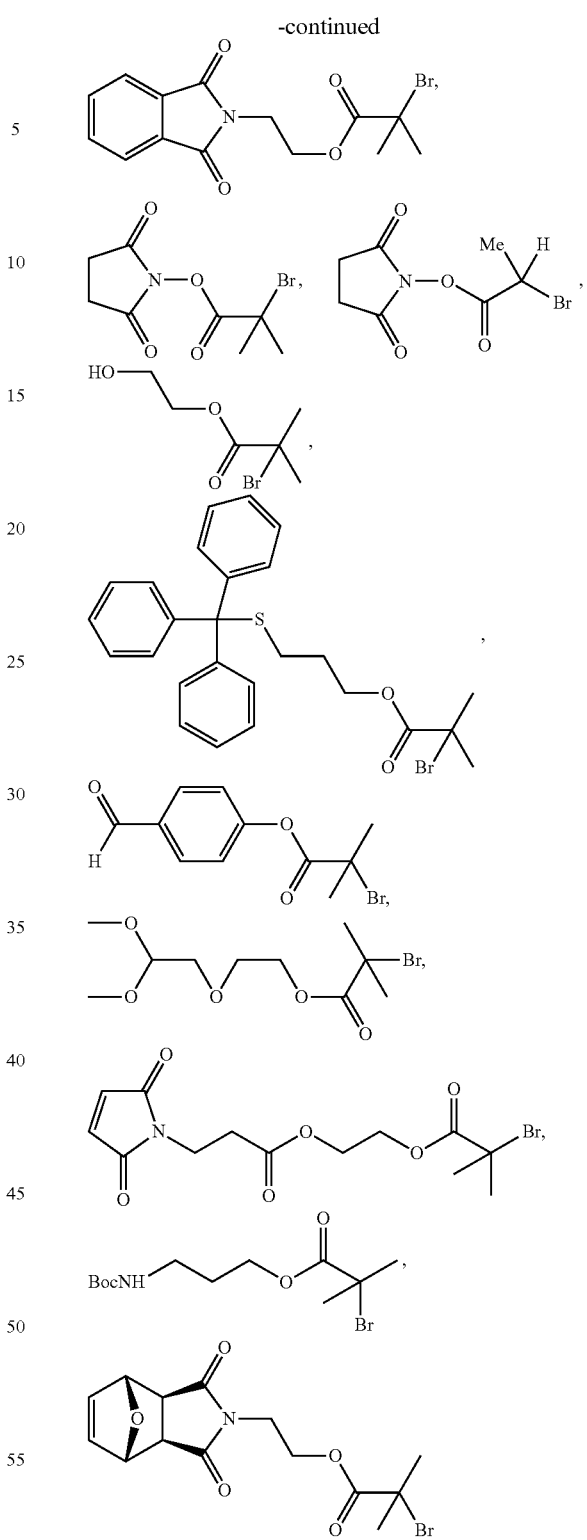

The catalyst may be capable of catalysing the polymerisation reaction by living radical polymerisation (see e.g. WO 97/47661) or living free radical polymerisation (see e.g. WO 96/30421, WO 97/18247 and Karnagaito M., et al., Chem. Rev. (2001), Vol. 101 (12), pages 3689-3745).

Preferably the catalyst comprises a ligand which is any N—, O—, P— or S— containing compound which can coordinate in a δ-bond to a transition metal or any carbon-containing compound which can coordinate in a π-bond to the transition metal, such that direct bonds between the transition metal and growing polymer radicals ate not formed.

The catalyst may comprise a first compound

MY where: M is a transition metal having an oxidation state which is capable of being oxidised by one form a oxidation state, Y is a mono, divalent or polyvalent counterion.

The catalyst may also be defined by the formula:

$$[ML_m]^{n+}A^{n-}$$

where: M=a transition metal having an oxidation state which is capable of being oxidised by one formal oxidation state, L=an organodilmine where at least one of the nitrogens of the diimine is not part of an aromatic ring, A=anion, n=integer of 1 to 3, m=an integer of 1 to 2.

The metal on may be attached to a coordinating ligand, such as $(CH_3CN)_4$. Y may be chosen from Cl, Br, F, I, $NO_3$, $PF_6$, $BF_4$, $SO_4$, CN, SPh, SCN, SePh or inflate ($CF_3SO_3$). Copper (I) inflate may be used. This is available; in the form of a commercially available benzene complex $(CF_3SO_3Cu)_2C_6H_6$.

The especially preferred compound used is CuBr.

A may be F, Cl, Br, I, N, $O_3$, $SO_4$ or $CuX_2$ (where X is a halogen).

The transition metal may be selected from $Cu^+$, $Cu^{2+}$, $Fe^{3+}$, $Ru^{2+}$, $Ru^{3+}$, $Cr^{2+}$, $Cr^{3+}$, $Mo^{2+}$, $Mo^{3+}$, $W^{2+}$, $W^{3+}$, $Mn^{3+}$, $Mn^{4+}$, $Rh^{3+}$, $Rh^{4+}$, $Re^{2+}$, $Re^{3+}$, $Co^+$, $Co^{2+}$, $V^{2+}$, $V^{3+}$, $Zn^+$, $Zn^{2+}$, $Au^+$, $Au^{2+}$, $Ag^+$ and $Ag^{2+}$.

Preferably the organodiimine has a formula selected from:

a 1,4-diaza-1,3-butadiene a 2-pyridine carbaldehyde imine an oxazolidone, or a quinoline carbaldehyde where $R_1$, $R_2$, $R_{10}$, $R_{11}$, $R_{12}$ and $R_{13}$ may be varied independently and $R_1$, $R_2$, $R_{10}$, $R_{11}$, $R_{12}$ and $R_{13}$ may be H, straight chain, branched chain or cyclic saturated alkyl, hydroxyalkyl, carboxyalkyl, aryl (such as phenyl or phenyl substituted where substitution is as described for $R_4$ to $R_9$) $CH_4Ar$ (where Ar=aryl or substituted aryl) or a halogen. Preferably $R_1$, $R_2$, $R_{10}$, $R_{11}$, $R_{12}$ and $R_{13}$ may be a $C_1$ to $C_{20}$ alkyl, hydroxyalkyl or carboxyalkyl, in particular $C_1$ to $C_4$ alkyl, especially methyl or ethyl, n-propylisopropyl, n-butyl, sec-butyl, tert butyl, cyclohexyl, 2-ethylhexyl, octyl decyl or lauryl.

Preferred ligands include:

Formula 28

Formula 29

Formula 30

Formula 31

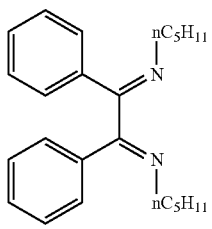
Formula 32
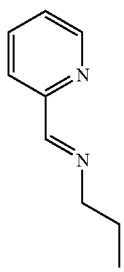
Formula 33
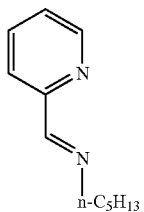
Formula 34
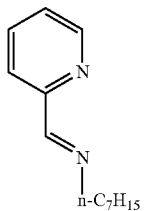
Formula 35
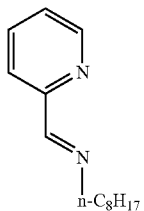
Formula 36
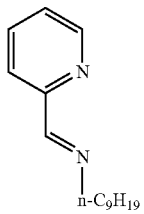
Formula 37
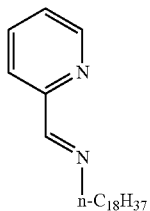
Formula 38
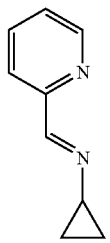
Formula 39
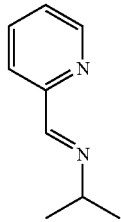
Formula 40
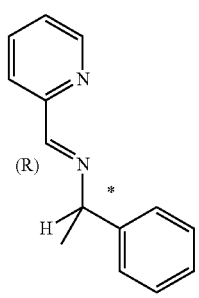
Formula 41
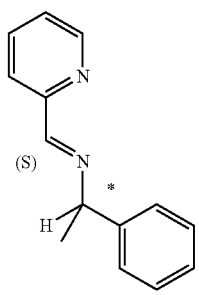
Formula 42
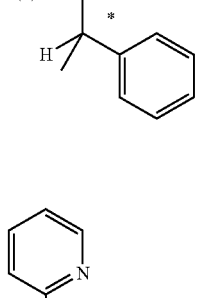
Formula 43
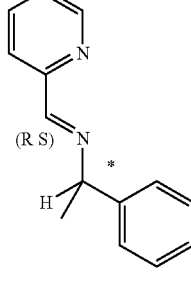
Formula 44
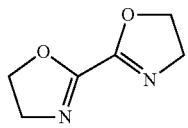

-continued

Formula 45

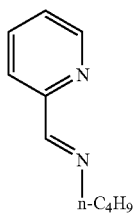

Formula 46

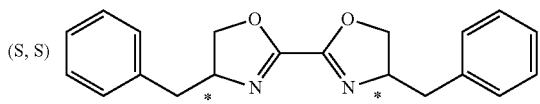

Formula 47

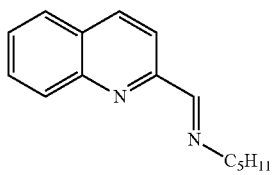

Formula 48

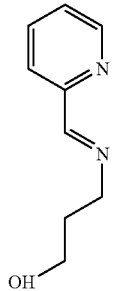

Formula 49

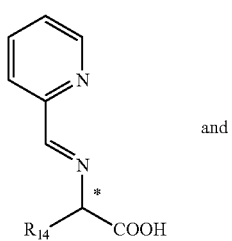

and

Formula 50

-continued

Formula 51

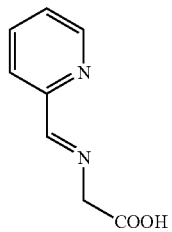

where * indicates a chiral centre

R14=Hydrogen, $C_1$ to $C_{10}$ branched chain alkyl, carboxy- or hydroxy-$C_1$ to $C_{10}$ alkyl.

Preferably the catalyst is

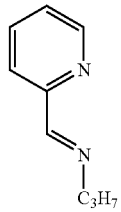

with CuBr

Preferably the organodiimine is N-(n-propyl)-2-pyridyl-methanimine (NMPI), N-ethyl-2-pyridyl methanimine or N-(n-ethyl)-2-pyridylmethanimine.

Other catalysts are described in WO 96/30421 and WO 97/18247.

Preferably the catalyst comprises a bipyridine group, such as 4,4'-di(5-nonyl)-2,2'-bipyridyl (dNbpy).

A plurality of different monomers as defined in part (i) of the invention may be used. This allows the production of statistical co-polymers.

Alternatively, or additionally, a block co-polymer may be produced by additionally polymerising one or more different olefinically unsaturated monomers. For example, the olefinically unsaturated monomers may be selected from methyl methacrylate, ethyl methacrylate, propyl methacrylate all isomers), butyl methacrylate (all isomers), and other alkyl methacrylates; corresponding acrylates; also functionalised methacrylates and acrylates including glycidyl methacrylate, trimethoxysilyl propyl methacrylate, allyl methacrylate, hydroxyethyl methacrylate, hydroxypropyl methacrylate, dialkylaminoalkyl methacrylates; fluoroalkyl (meth)acrylates; methacrylic acid, acrylic acid; fumaric acid (and esters), itaconic acid (and esters), maleic anhydride; styrene, α-methyl styrene; vinyl halides such as vinyl chloride and vinyl fluoride; acrylonitrile, methacrylonitrile; vinylidene halides of formula $CH_2=C(Hal)_2$ where each halogen is independently Cl or F; optionally substituted butadienes of the formula $CH_2=C(R^{15}) C(R^{15})=CH_2$ where $R^{15}$ is independently H, $C_1$ to $C_{10}$ alkyl, Cl, or F; sulphonic acids or derivatives thereof of formula $CH_2=CHSO_2OM$ wherein M is Na, K, Li, $N(R^{16})_4$ where each R is independently H or C1 to C10 alkyl, COZ, ON, $N(R^{16})_2$ or $SO_2OZ$ and 2 is H, Li, Na, K or $N(R^{16})_4$; acrylamide or derivatives thereof of formula $CH_2=CHCON(R^{16})_2$ and methacrylamide or derivative thereof of formula $CH_2=C(CH_3)CON(R^{16})_2$.

The monomers may be polymerised prior to or after the polymerisation of the monomers as defined in part (I) of the invention.

The polymerisation reaction may be reactive in a number of different solvents, such as hydrophobic or hydrophilic solvents. These include water, propionitrile, hexane, heptane, dimethoxyethane, diethoxyethane tetrahydrofuran, ethylacetate, diethylether, N,N-dimethylformamide, anisole, acetonitrile, diphenylether, methylisobutyrate, butan-2-one, toluene and xylene.

The reaction temperature may be carried out from −20 to greater than 200° C., especially +5 to 130° C. WO 97/47661, for example, shows examples of living radical polymerisation and the typical conditions that may be used.

Preferably, the ratio of organodiimine:transition metal is 0.01 to 1000, preferably 0.1 to 10, and transition metal ion (as MY):initiator is 0.0001 to 1000, preferably 0.1 to 10, where the degree of polymerisation is controlled by the ratio of monomer to initiator. All ratios are given as weight : weight. Preferably the components are the catalyst of formula: $[ML_m]^{n+}A^{n-}$ (defined above) are at a ratio of catalyst: initiator of 3:1 to 1:100.

Preferably, the amount of diimine metal used in the system is between 100:1 and 1:1, preferably 5:1 to 1:1, more preferably 3:1 to 1:1, by weight.

Preferably the concentration of monomer in a solvent used is 100%-1%, preferably 100%-5%, vol.:vol.

Preferred ratios of initiator to catalyst or 1:100-100:1, typically 1:1.

Preferred ratios of monomer:initiator are 1:1 to 10,000:1, especially 5:1 to 100:1.

The reaction may be undertaken under an inert atmosphere such as nitrogen or argon, and may be carried out in suspension, emulsion, mini-emulsion or in a dispersion.

Preferably, the catalyst is a supported catalyst, that is at least a part of the catalyst is attached to a support. Such supported catalysts are shown in, for example, WO 99/28352.

The support may be inorganic, such as silica, especially silica gel. Alternatively, the support may be organic, especially an organic polymer, such as a cross-linked organic polymer, including poly (styrene-w-dinylbertzone). The support may be in the form of beads. The advantage of using a supported catalyst is that it allows the catalyst to be removed from the system and recycled/reused.

The comb polymer may incorporate a fluorescently-labelled monomer. For example, the method may additionally comprise a step of copolymerising or block polymerising with at least one fluorescently-labelled monomer capable of undergoing addition polymerisation. This can be carried out simply by using a monomer which has a fluorescent moiety, such as fluorescein, or coumarin, attached to an olefinically unsaturated moiety. The olefinically unsaturated moiety may be selected from those unsaturated moieties defined above.

Preferably, the fluorescent label is coumarin, especially coumarin 343. Coumarin is particularly advantageous because it allows the comb polymer to be used to attach to proteins and the attachment of the proteins to be visualised using a confocal microscope. This allows, for example, the detection of individual proteins or indeed the visualisation of whole bacterial or other cells. Indeed, initial results have indicated that bacterial cells can be readily visualised, using a comb polymer according to the invention, to attach to *E. coli* and *Streptomyces* cells.

A further aspect of the invention provides initiator compounds capable of being used in a living radical polymerisation reaction comprising a moiety which, when attached to a polymer, is capable of binding to a protein or polypeptide. Initiators for use in a living radical polymerisation reaction having the following formulae are also provided:

A-S—C(O)—R, A-S—C(S)—O—R, R—S—C(O)-A, R—S—C(S)O-A, where R is $C_1$ to $C_{20}$ substituted or non-substituted, straight chain, branched chain, cyclic, heterocyclic or aromatic alkyl;

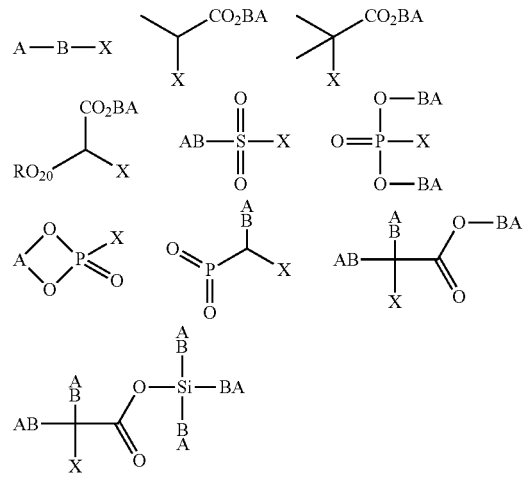

where: X=a halide, especially Cl or Br,
A=a moiety which, when attached to the comb polymer, is capable of binding to a protein or polypeptide,
B is a linker and may or may not be present.

Preferably, A is selected from succinimidyl succinate, N-hydroxy succimimide, succinimidyl propionate, succinimidyl batanoate, propionaldehyde, acetaldehyde, tresylate, triazine, vinyl sulfone, benzotriazole carbonate, maleimide, pyridyl sulfide, iodoacetamide and succinimidyl carbonate.

Preferably, the linker is selected from a $C_1$ to $C_{20}$ substituted or non-substituted, straight chain, branched Chain cyclic, heterocyclic or aromatic alkyl group; —$(CH_2Z)_a$CH$_2$—, —CH$_2$ZCH$_2$—, —$(CH_2CH_2Z)_n$—R, —$(CH_2CH(CH_3Z)_n$—R, —$(CH_2)_b$—C(O)—NH—$(CH_2)_c$—, —$(CH_2)_a$—NH—C(O)—$(CH_2)_y$—, —N(R)$_2$—; —S—; —N—R; or —O—R; where R=$C_1$ to $C_{20}$ substituted or non-substituted, straight chain, branched chain cyclic, heterocyclic or aromatic alkyl, Z is O or S, and n, a, b and c are independently selectable integers between 1 and 10, Preferably the moiety capable of reacting with a protein or polypeptide has a formula:

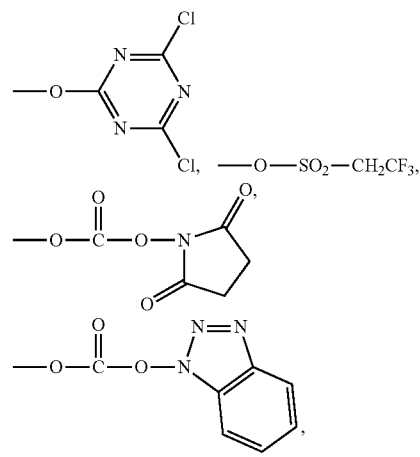

-continued
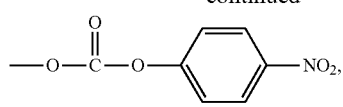
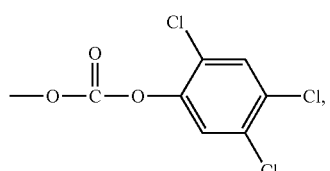
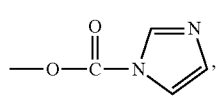
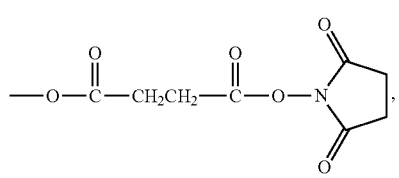
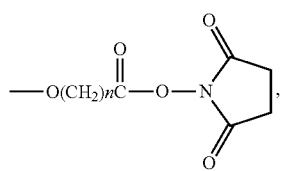
where n=integer of 0 to 10
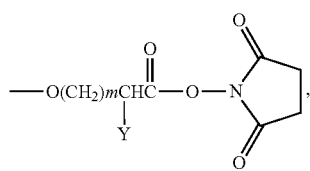
where m=integer of 0 to 10, Y is an aliphatic or aromatic moiety
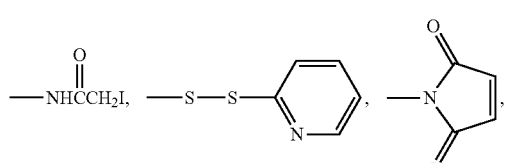
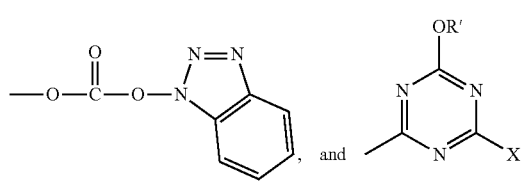
where R' is H, methyl, ethyl, propyl or butyl, X is a halide, especially Cl or Br.
Preferably the initiator has a formula of:
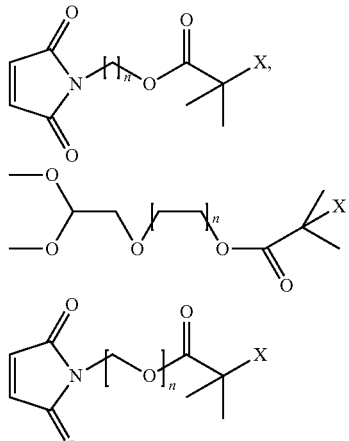
where n is an integer of 0 to 10, and X is a halide, especially Cl or Br.
The initiator especially has the formula:
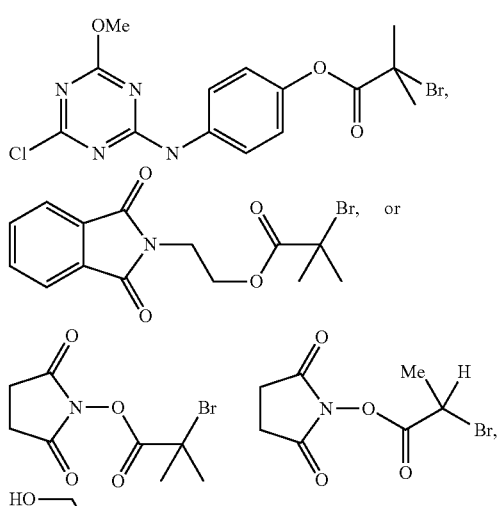
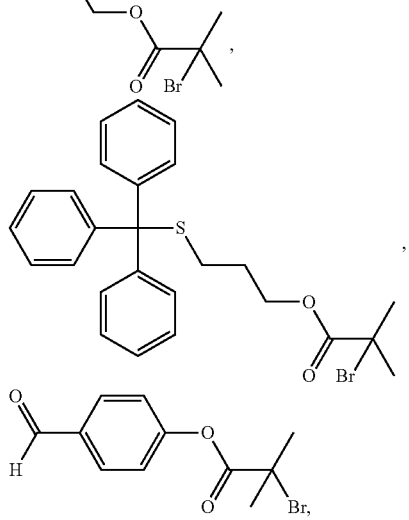

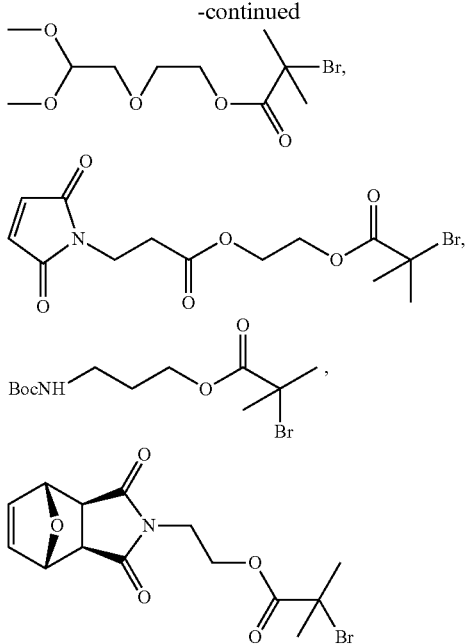

The terminal amine group may be protected by any suitable protecting group, such as BOC. Deprotection is achieved by addition of acid, such as trifluoroacetic acid. Alternatively a furan intermediate may be produced which can then be converted to maleimide.

Under normal conditions, the aldehyde-based initiators will tend to react non selectively with proteins, i.e, they will react substantially equally with both terminal nitrogen atoms and, for example, a lysine $NH_2$ group, if the reaction conditions are not controlled. However, under the right reaction pKa for the particular aldehyde chosen, the aldehyde can be controlled to specifically target the terminal nitrogen. A further aspect of the invention provides comb polymers capable of binding protein or polypeptide obtainable by a method of the invention.

A further aspect provides a comb polymer having a general formula:

$$A\text{-}(D)_d\text{-}(E)_e\text{-}(F)_f$$

where: A may or may not be present, and where present is a moiety capable of binding to a protein or a polypeptide, D, where present, is obtainable by additional polymerisation of one or more olefinically unsaturated monomers which are not as defined in E, E is obtainable by additional polymerisation of a plurality of monomers which are linear, branched, or star-shaped, substituted or non-substituted, and have an olefinically unsaturated moiety, F, where present, is obtainable by additional polymerisation of one or more olefinically unsaturated monomers which are not as defined in E, d and f are an integer between 0 and 500, especially 0 to 300 or 0 to 100, e is an integer of 0 to 1000, especially 0 to 10, 50, 100, 200, 300, 400, 500, 600, 700, 800 or 900 and wherein when A is present, at least one of D, F and F is present.

Preferred monomers used to obtain E are poly (alkylene glycol) or polytetrahydrofuran.

This includes both functionalised comb polymer and non-functionalised comb polymer, where the moiety capable of attaching to a protein or polypeptide may be attached later by other chemistry.

Preferably the comb polymer has an average total, molecular weight of 2,000-80,000, especially 20,000-40,000.

Examples of preferred comb polymers, obtainable according to the process of the invention, are

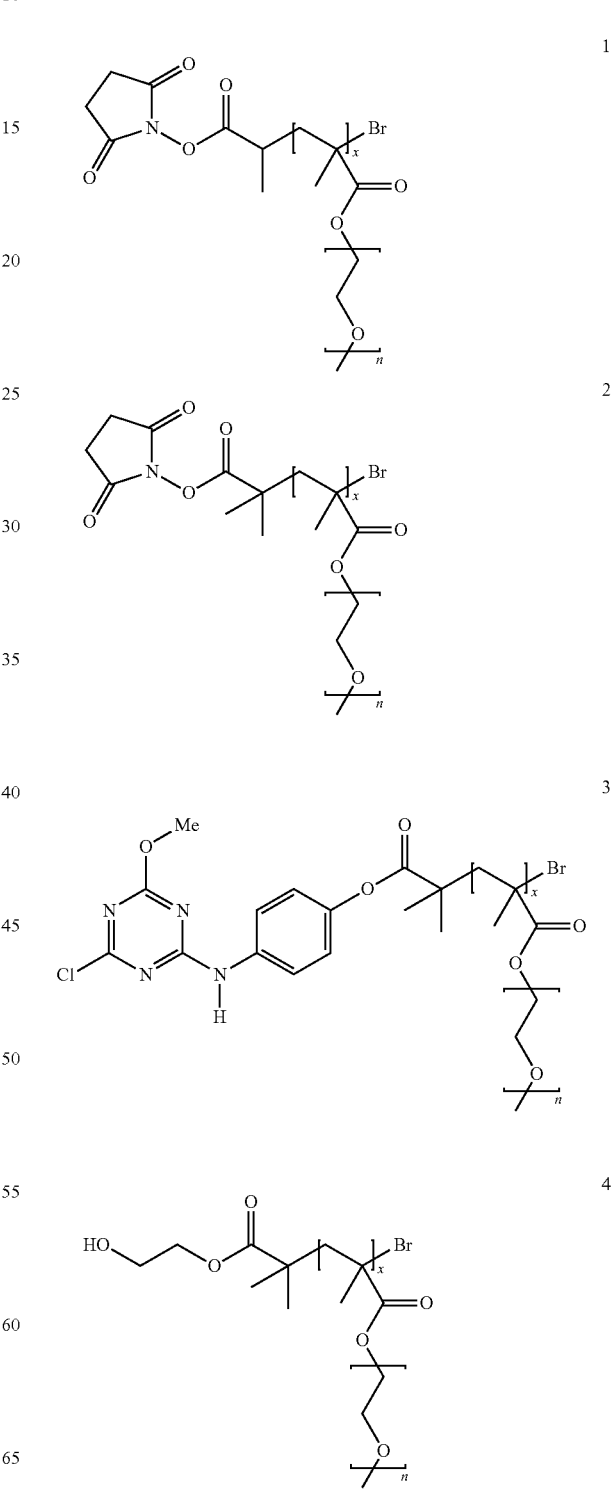

5

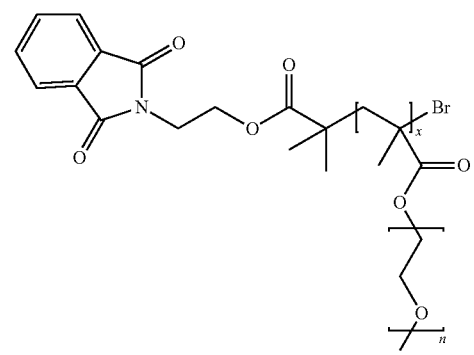

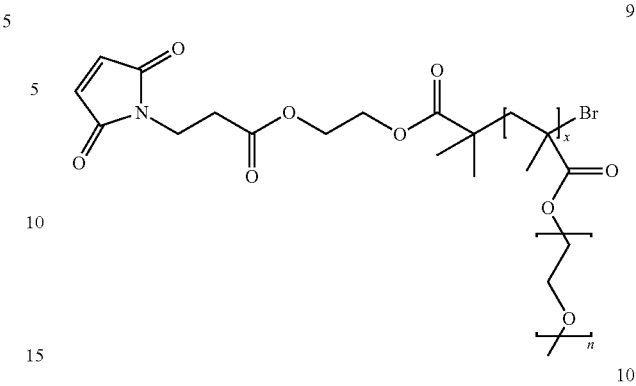

6

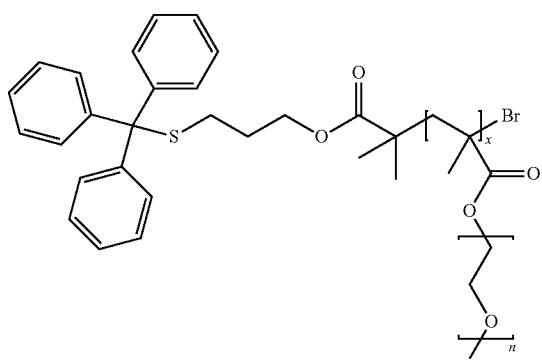

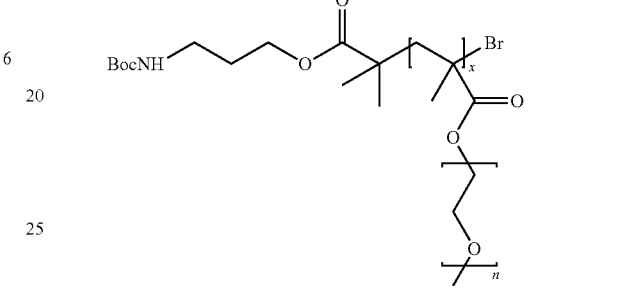

7

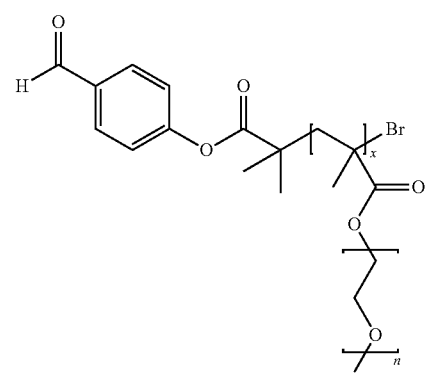

8

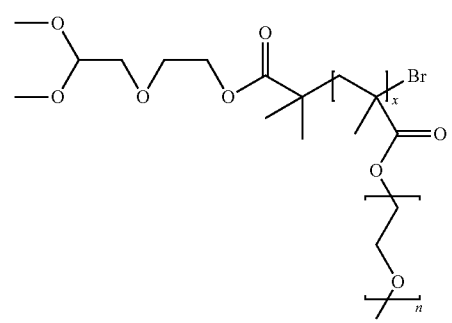

These polymers can be used either directly to react with useful biomolecules or converted simply into new macromolecules that will react with useful biomolecules.

The comb polymer may be fluorescently labelled, especially with a coumarin. A still further aspect of the invention provides a method of attaching a polymer to a compound comprising reacting a comb polymer according to the invention with said compound. The compound may be a protein or polypeptide or may indeed be any compound having a suitable free thiol or free amine group, depending on the initiator used. Such compounds include amines, such as benzylamines and ethylenediamine, amino acids and carbohydrates such as sugars.

Preferably such compounds are biologically-active compounds, such as drugs. The combination of such compounds in combination with a pharmaceutically acceptable carrier are also provided. The compounds may include cancer chemotherapeutic agents, antibiotics, anti-fungal and/or immunosuppressants.

For example, FIGS. 23 and 24 show HPLC traces and SDS-PAGE for the reaction of lysozyme with a polymer prepared according to the invention. These figures clearly illustrate the progress of the reaction as the polymer selectively conjugates to only one of lysozymes seven amino groups.

A still further aspect of the invention provides a method of fluorescently labelling a compound, virus, microorganism or cell comprising the step of reacting the compound, virus, microorganism or cell with a fluorescently labelled comb polymer according to the invention. The use of a comb polymer as a fluorescent label is also provided.

The fluorescently labelled comb polymer may be used to attach antibodies which in turn may be used to selectively bind to pre-defined antigens. This allows the selective labelling of the compounds to take place.

Methods of producing such antibodies are well-known in the art and indeed monoclonal antibodies may be produced by the well-known Kohler-Milstein method.

Previously, when polymers have been used to bind to proteins, they have had to be of a low molecular weight, as a polymer with a molecular weight of e.g. 20,000 could not be excreted from the body by the liver. To combat this problem, four polymers of approximately 5,000 molecular weight each were bound to the protein, and eventually excreted without problem. An advantage that is provided by the comb polymers of the invention is that they can possess molecular weights of 20,000 and still be bound to the proteins without the problems of excretion found with conventional polymers. This is due to an ester linkage which is found in each "finger" of the comb polymer. Preliminary results show that this ester linkage is readily hydrolysed by enzymes, causing the fingers to gradually break off the main polymer backbone. This enables a 20,000 molecular weight polymer to become smaller over time until it reaches a molecular weight which enables it to be excreted by the liver. Conventional chain polymers cannot offer this advantage but remain in the bloodstream without being excreted.

Initial results indicate that the comb polymers of the invention are stable over weeks in at serum, but slowly break down in the manner detailed above.

The invention will now be described by way of example only with reference to the following examples:

Figure 3:
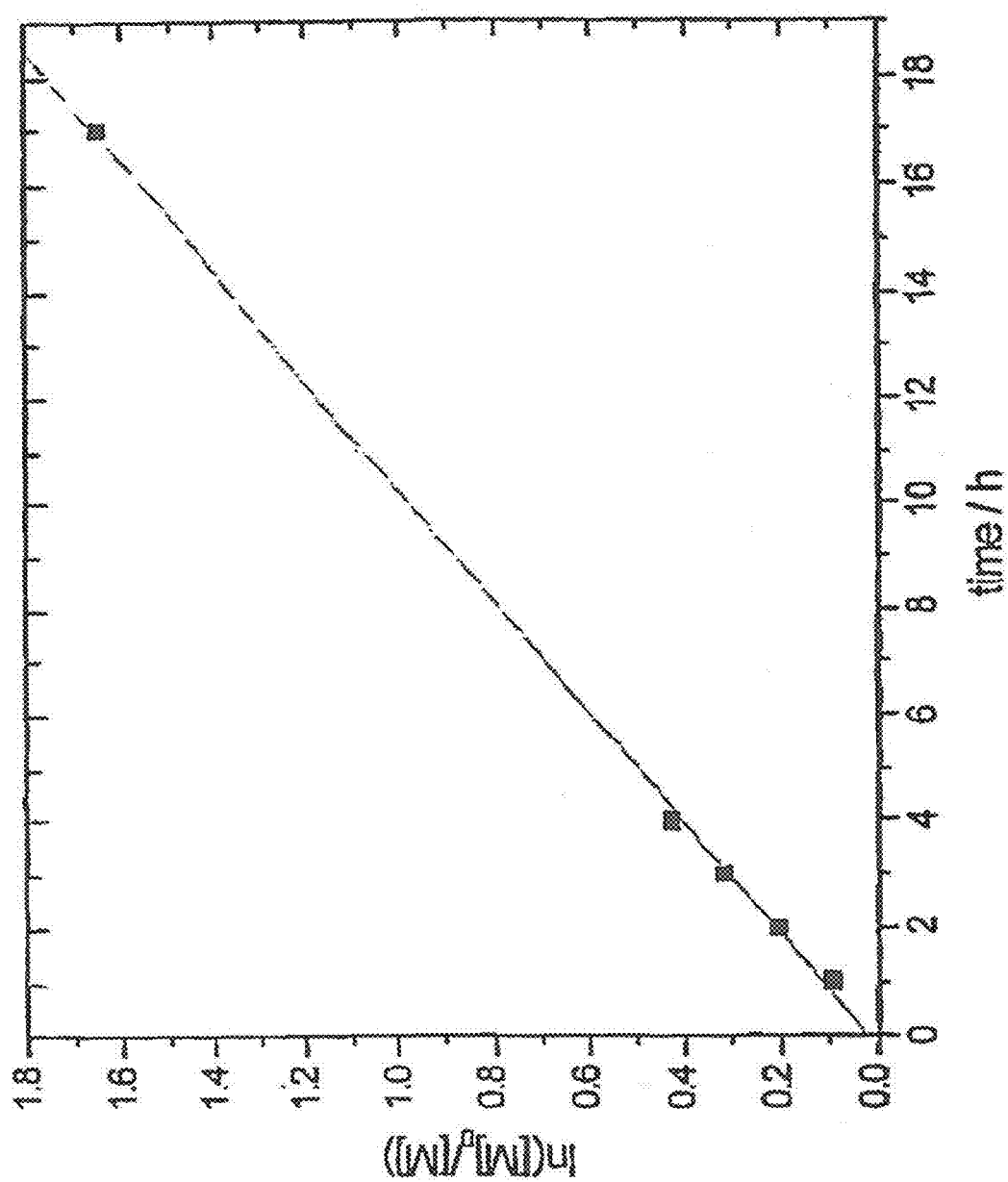

FIG. 3. First order kinetic plot for the LRP of PEGMA initiated by NHS—Br, $[PEGMA]_o/[CuBr]_o/[NHSBr]_o/[L]_o=10/1/1/2.1$ in toluene (33% v/v) at 30° C.

Figure 4:
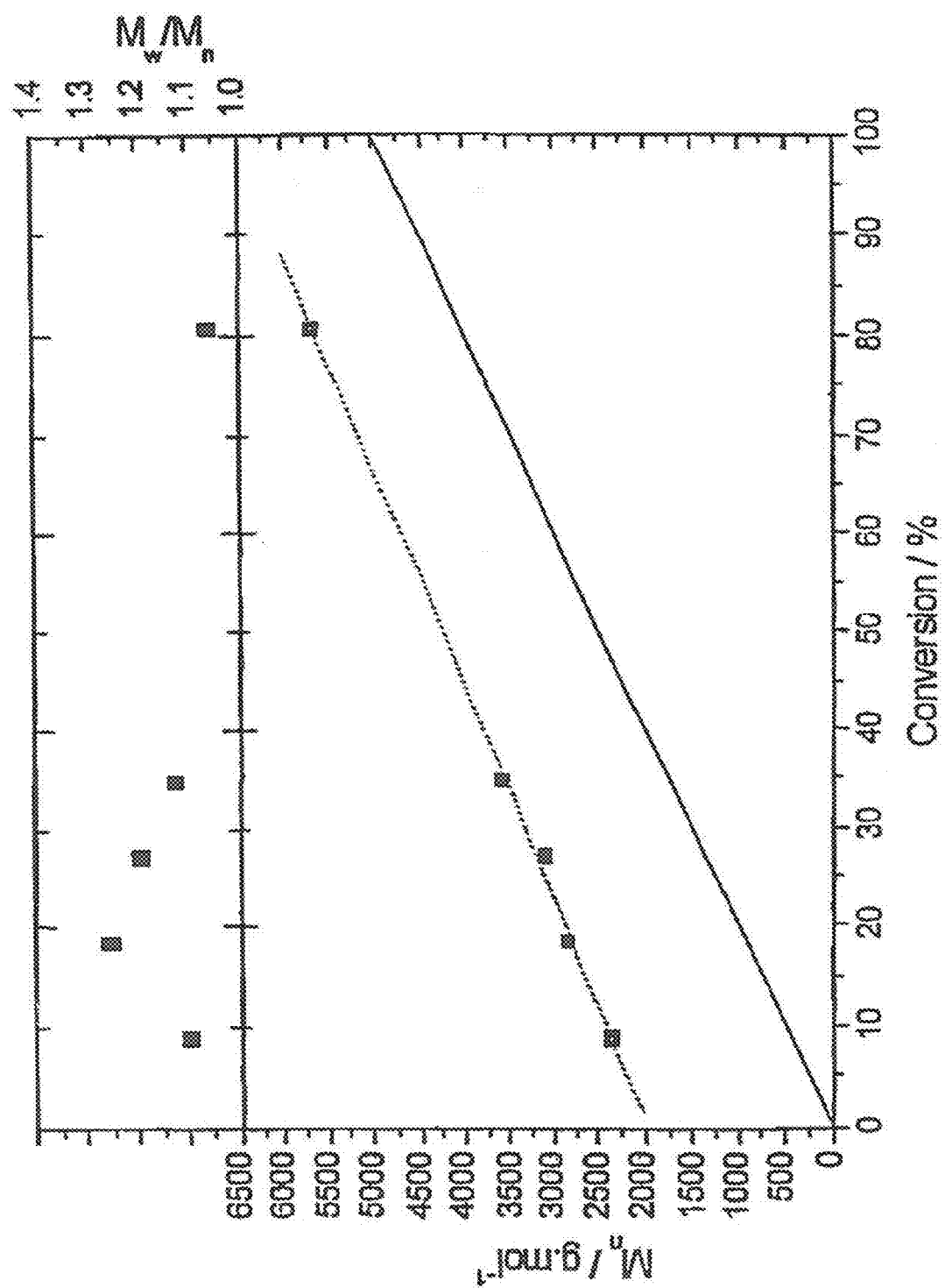

FIG. 4. Evolution of the molecular weight distribution and polydispersity for the LRP of PEGMA initiated by NHS—Br, $[PEGMA]_o/[CuBr]_o/[NHSBr]_o/[L]_o=10/1/1/2.1$ in toluene (33% v/v) at 30° C.

Figure 5:
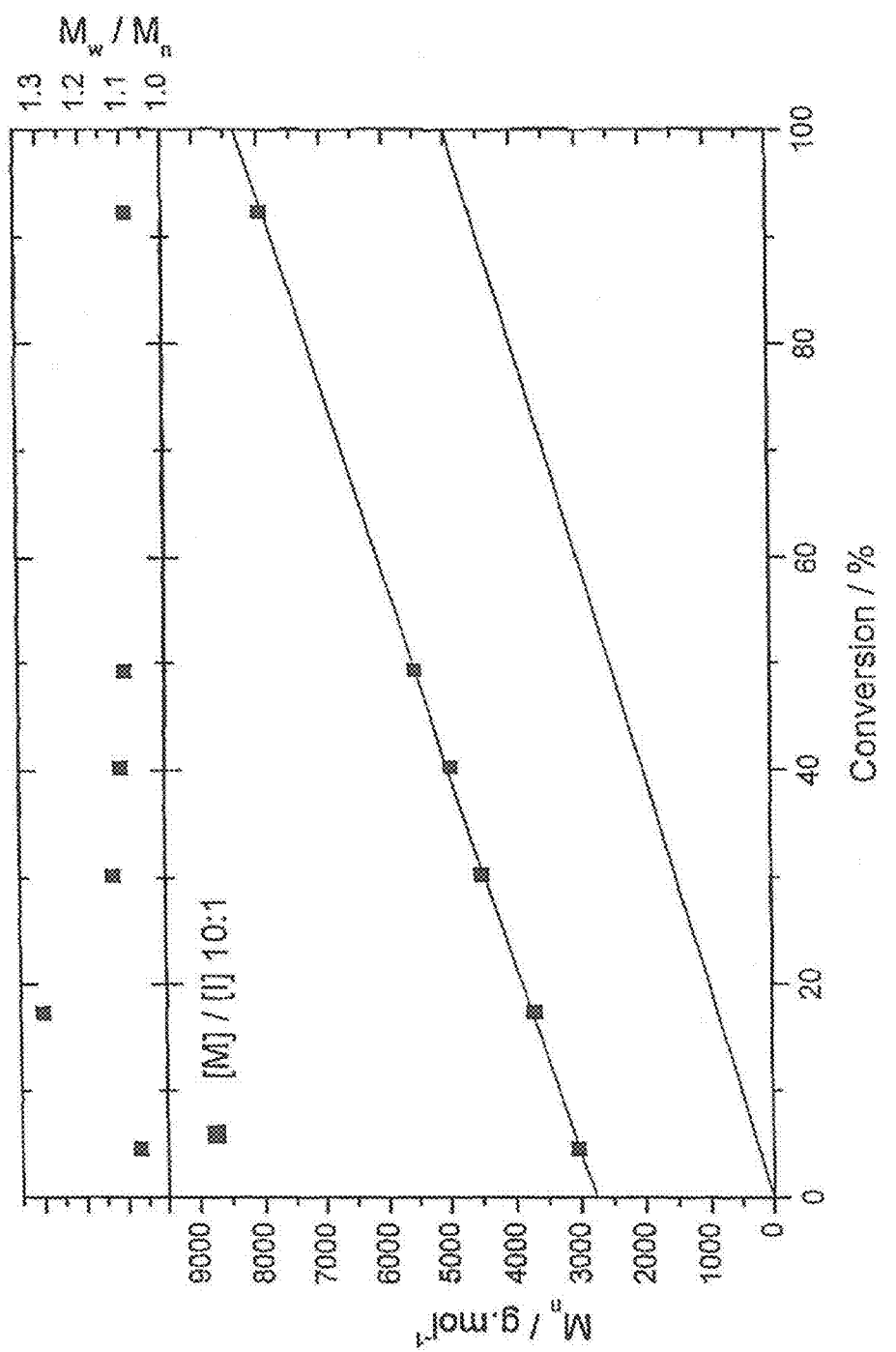

FIG. 5. Evolution of the molecular weight distribution and polydispeersity for the LRP of MPEG(395)MA initiated using initiator 8, $[MPEG(395)MA]_o[CuBr]_o/[NHSBr]_o=10/1/1/2$ in tuluene (50% v/v) at 30° C.

Figure 6:
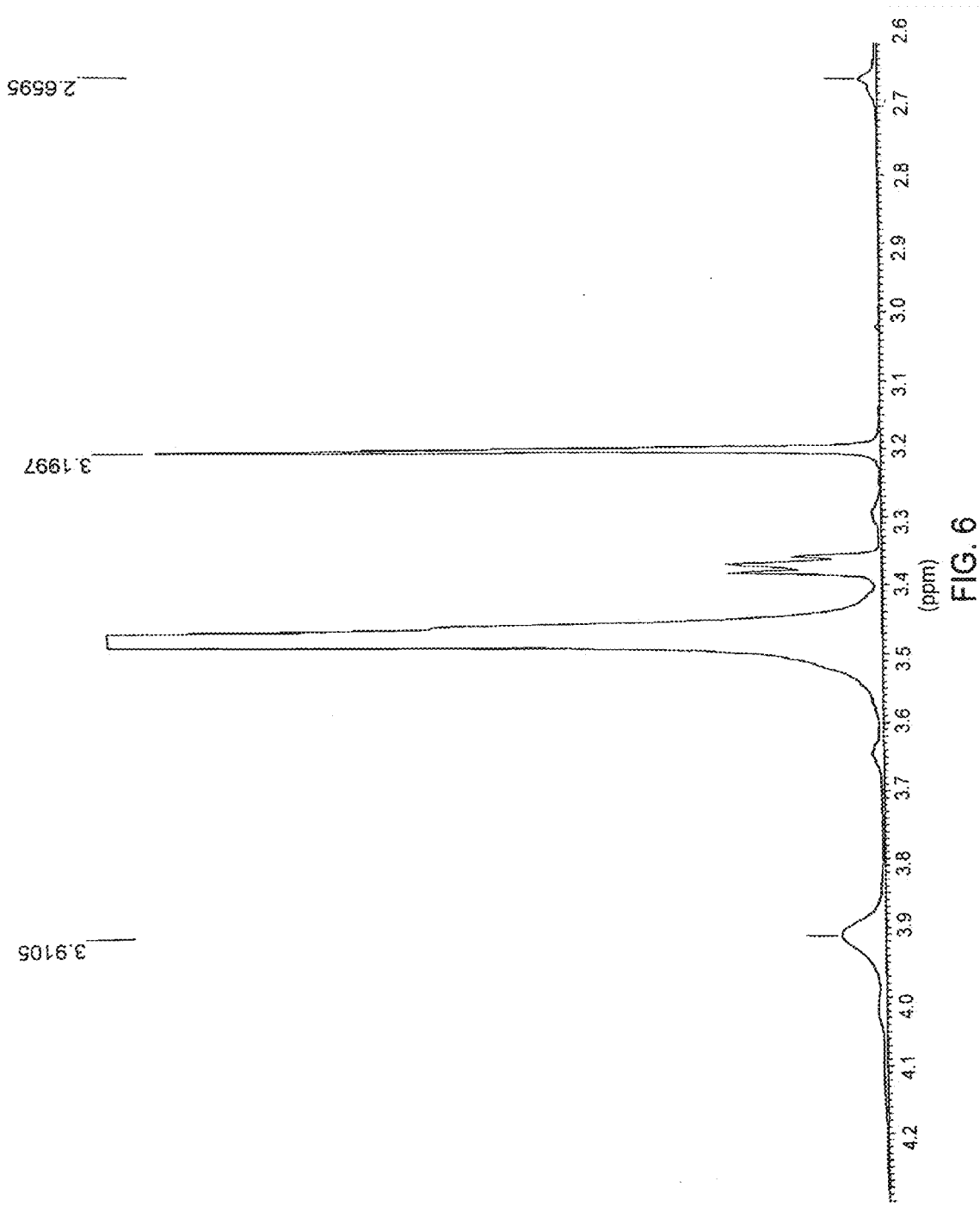

FIG. 6. Selected region (2.7-4.3 ppm) of the $^1H$ NMR spectrum of a NHS ester functionalised poly(MPEG(395) MA) prepared from initiator 8 ($M_n=6400$ g·mol$^{-1}$, $M_w/M_n=1.09$).

Figure 7:
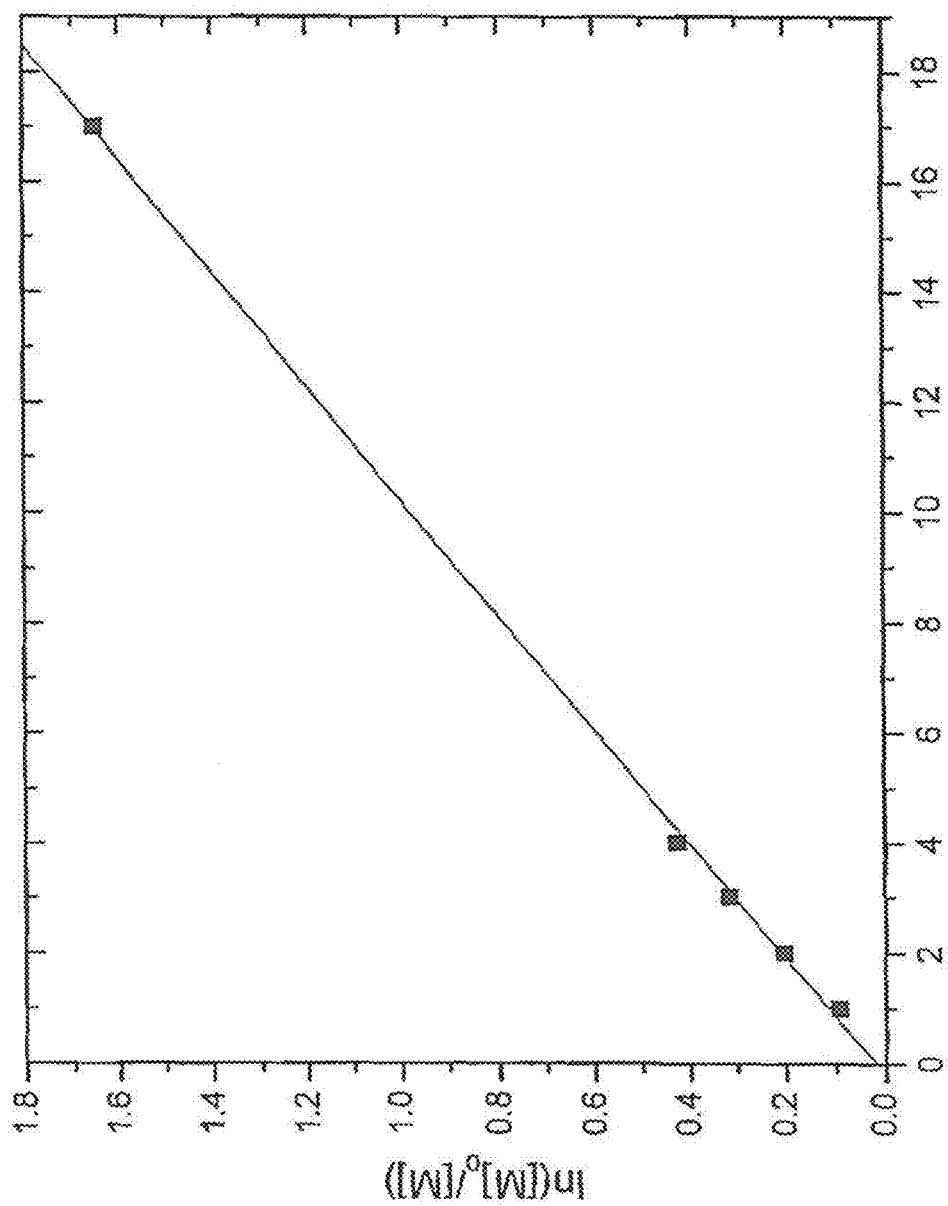

FIG. 7. First order kinetic plot for the LRP of MPEG(395) MA using initiator 7, $[MPEG(395)MA]_o/[CuBr]_o/[NHSBr]_o/[Propyl Ligand]_o=10/1/1/2$ ub toluene (50% v/v) at 30° C.

Figure 8:
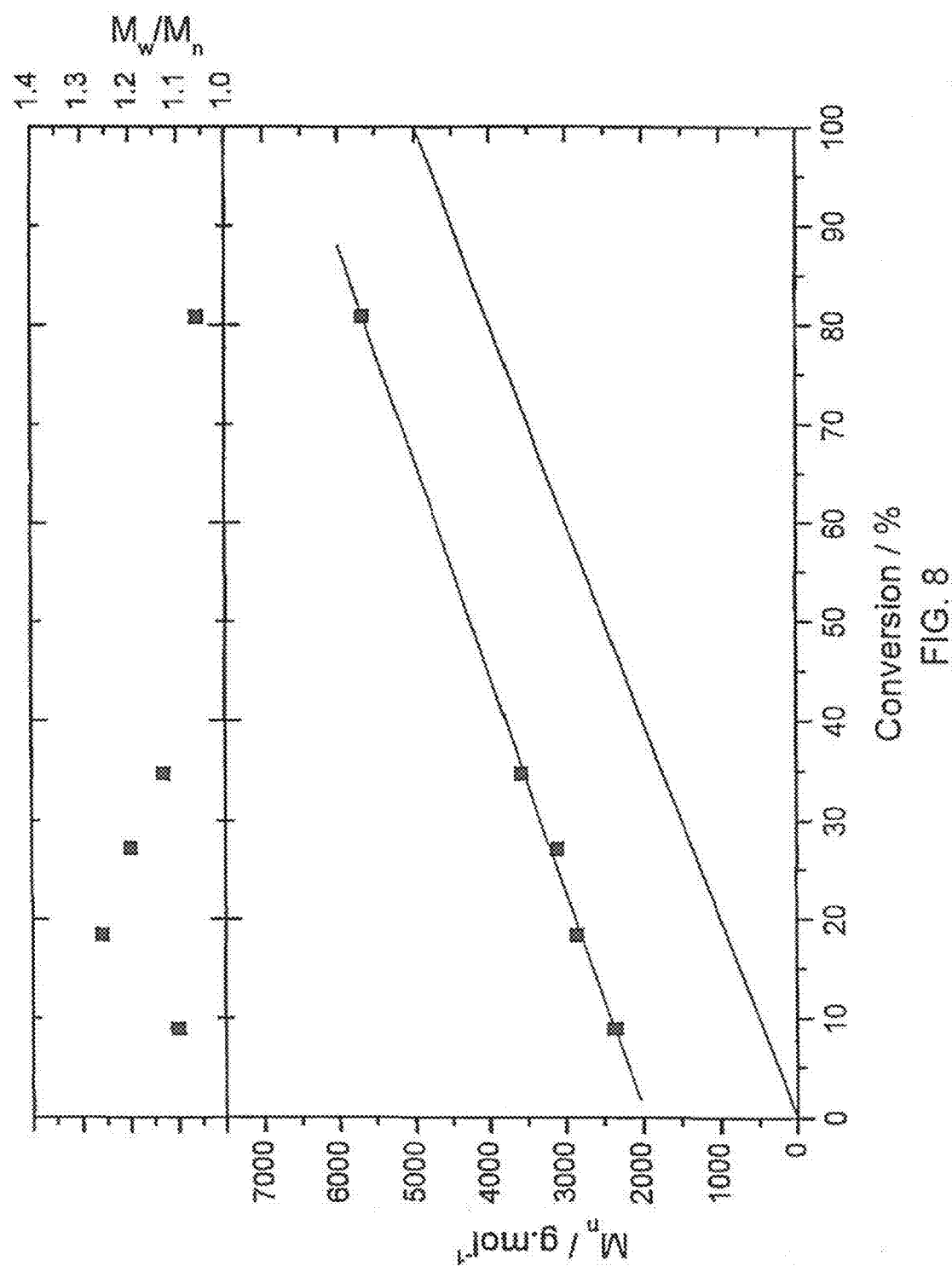

FIG. 8. Evolution of the molecular weight distribution and polydispersity for the LRP of MPEG(395)MA using initiator 7, $[MPEG(395)MA]_o/[CuBr]_o/[NHSBr]_o/[Propyl Ligand]_o=10/1/1/2$ in toluene at 30° C.

Figure 9:
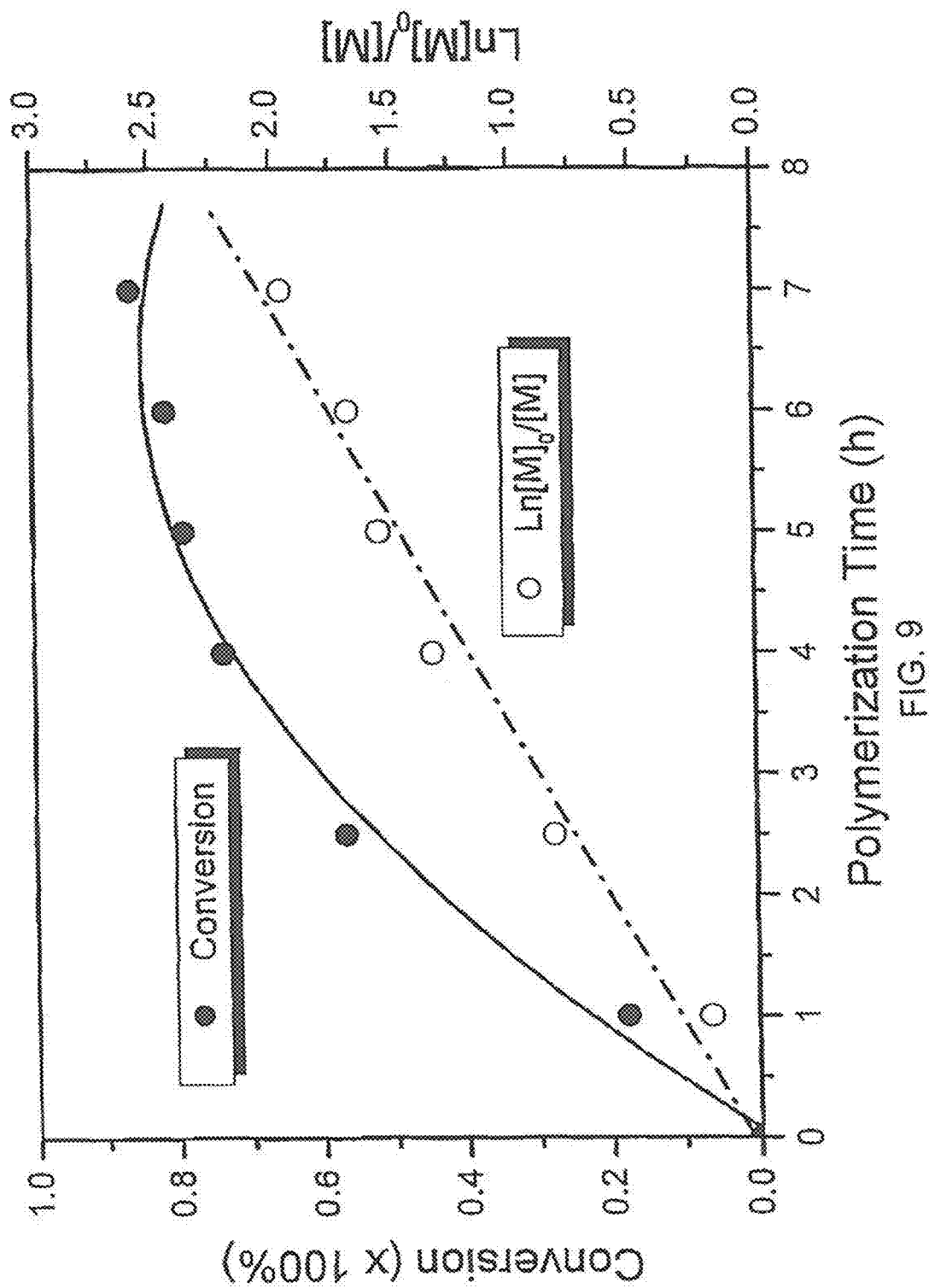

FIG. 9. Rate plot for TMM-LRP of MPEG(1000)MA initiator 12, [monomer]:[initiator]:[CuCl]:[L]=5:1:2:2, T=70° C.

Figure 10:
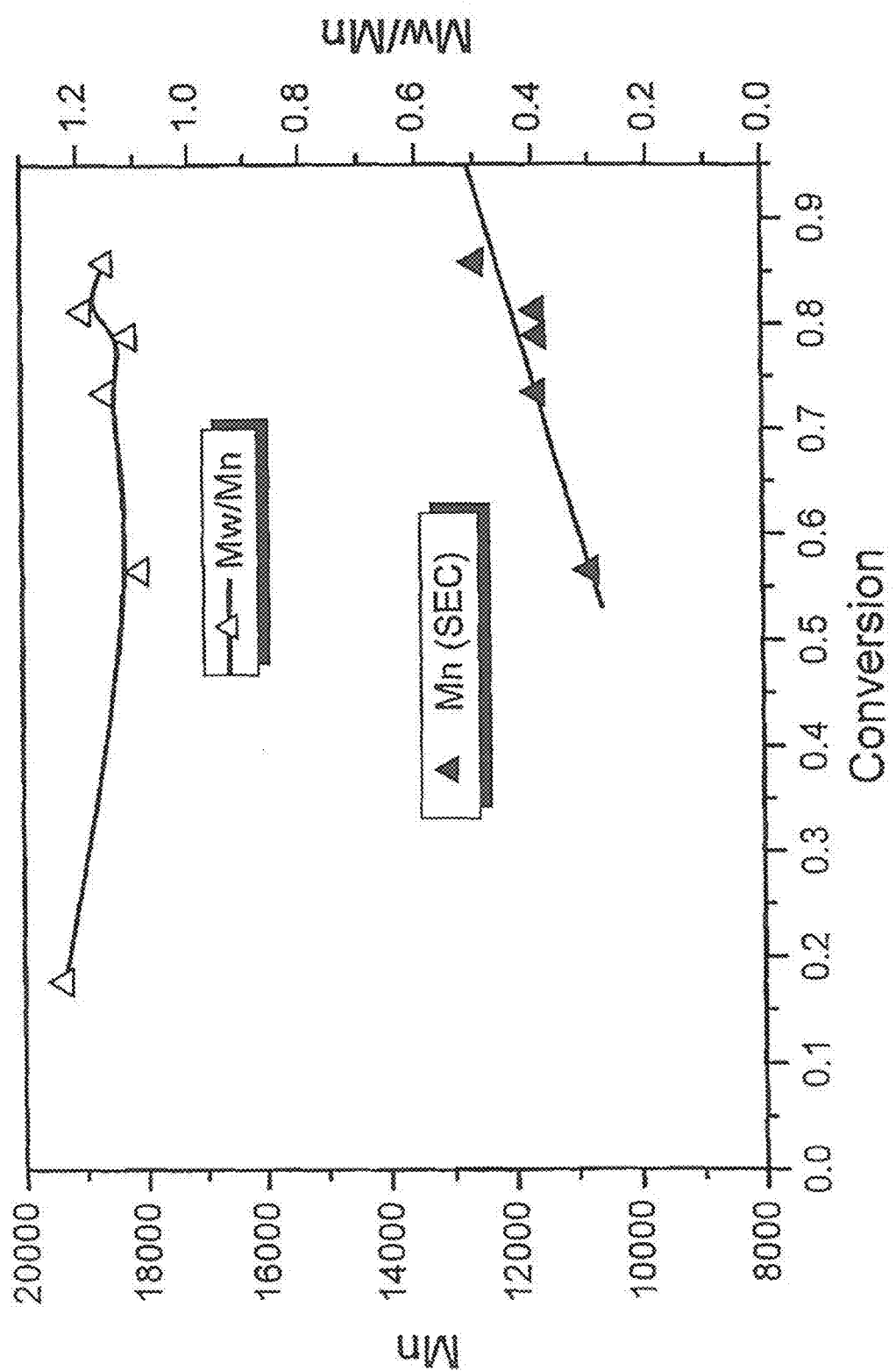

FIG. 10. Dependence of $M_n$ on conversion for MPEG (1000)MA initiator 12, [monomer]:[initiator]:[CuCl]:[L]=5:1:1:2, T 70° C.

Figure 11:
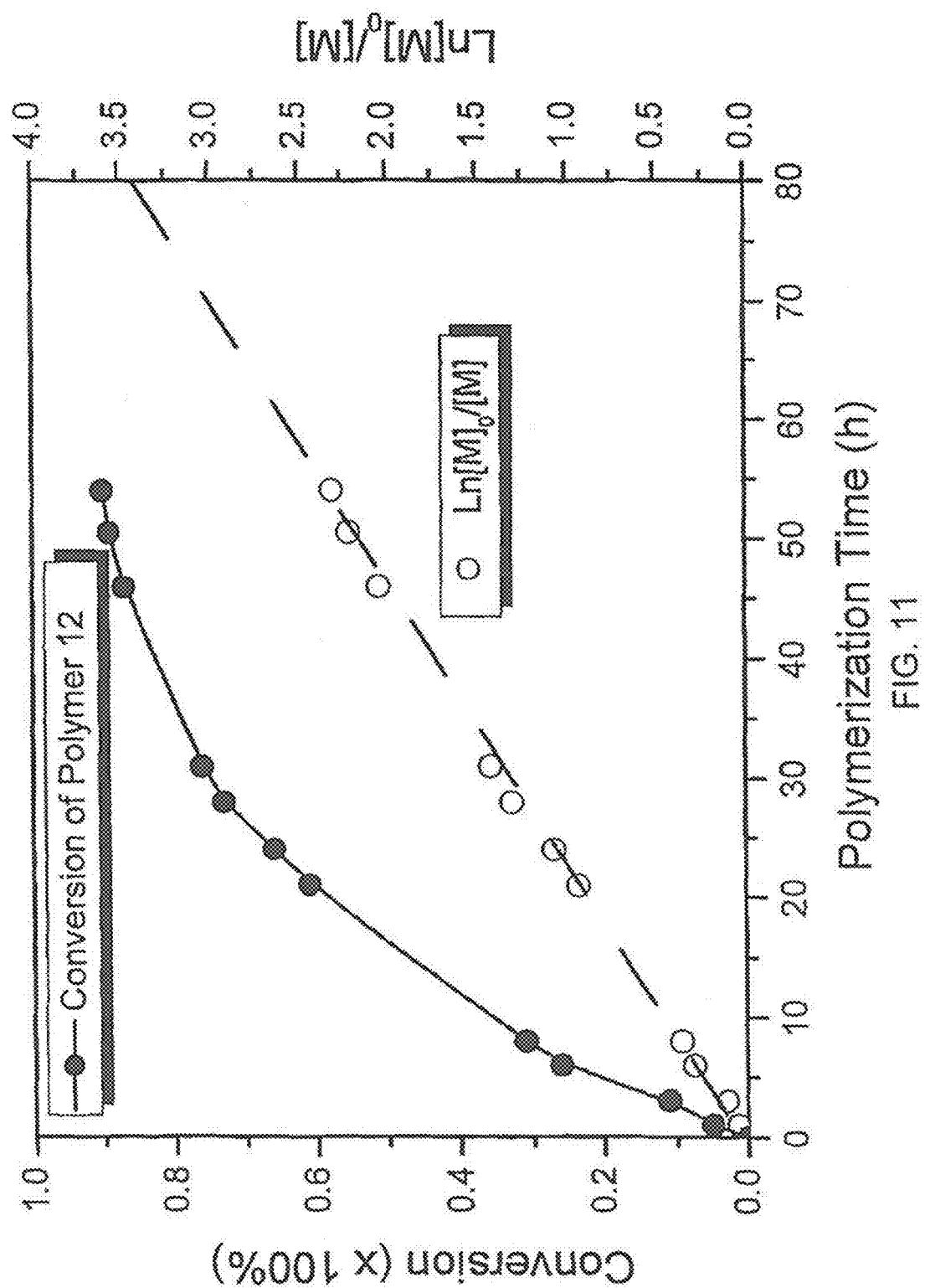

FIG. 11. Rate plot thr TMM-LRP of MPEG(1000)MA initiator 12, [monomer]:[initiator]:[CuBr]:[L]=20:1:1:2, T=50° C.

Figure 12:
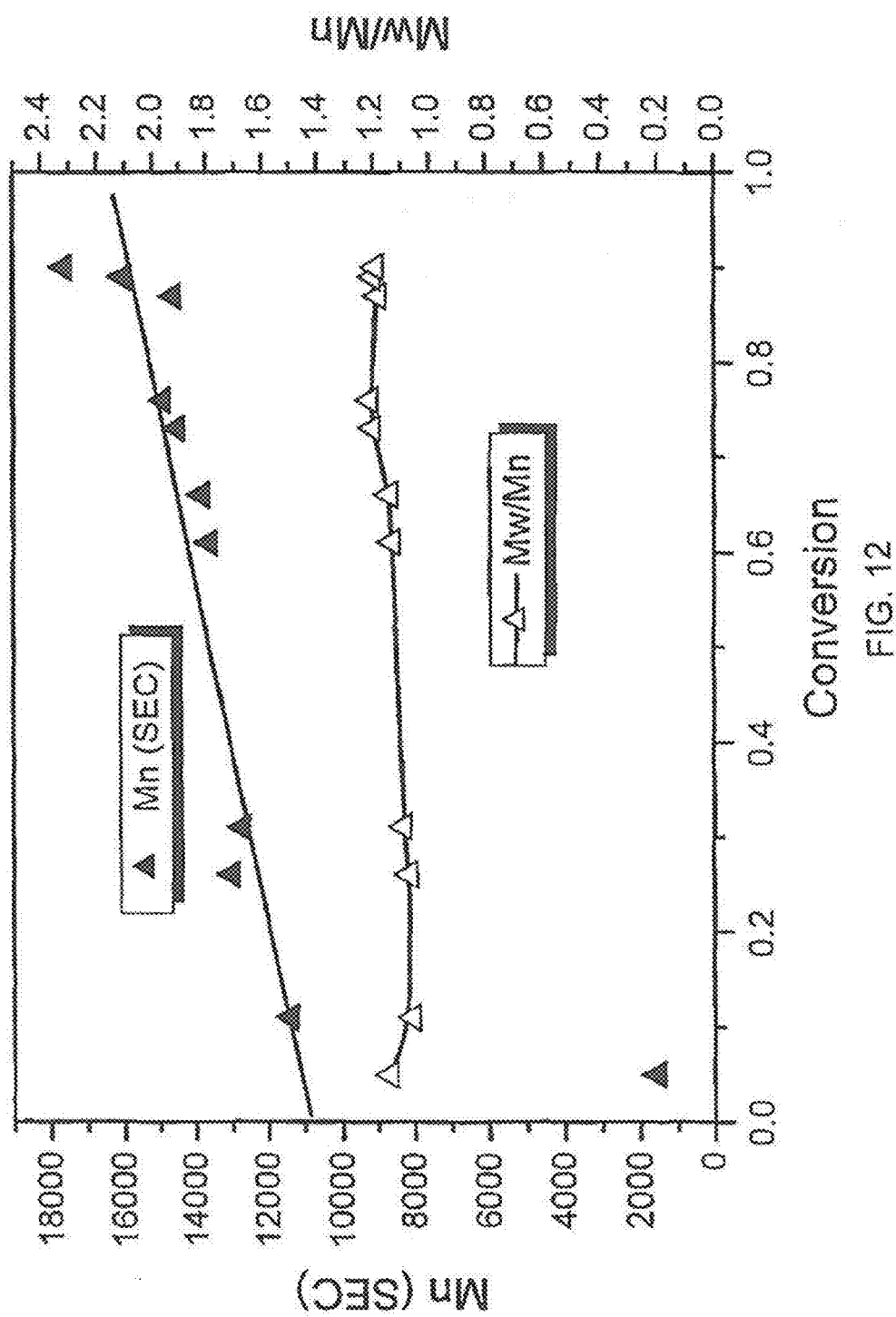

FIG. 12. Dependence of $M_n$ on conversion for TMM-LRP of MPEG(1000)MA initiator 12, [monomer]:[initiator]:[CuBr]:[L]=20:1:1:2, T=50° C.

Figure 13:
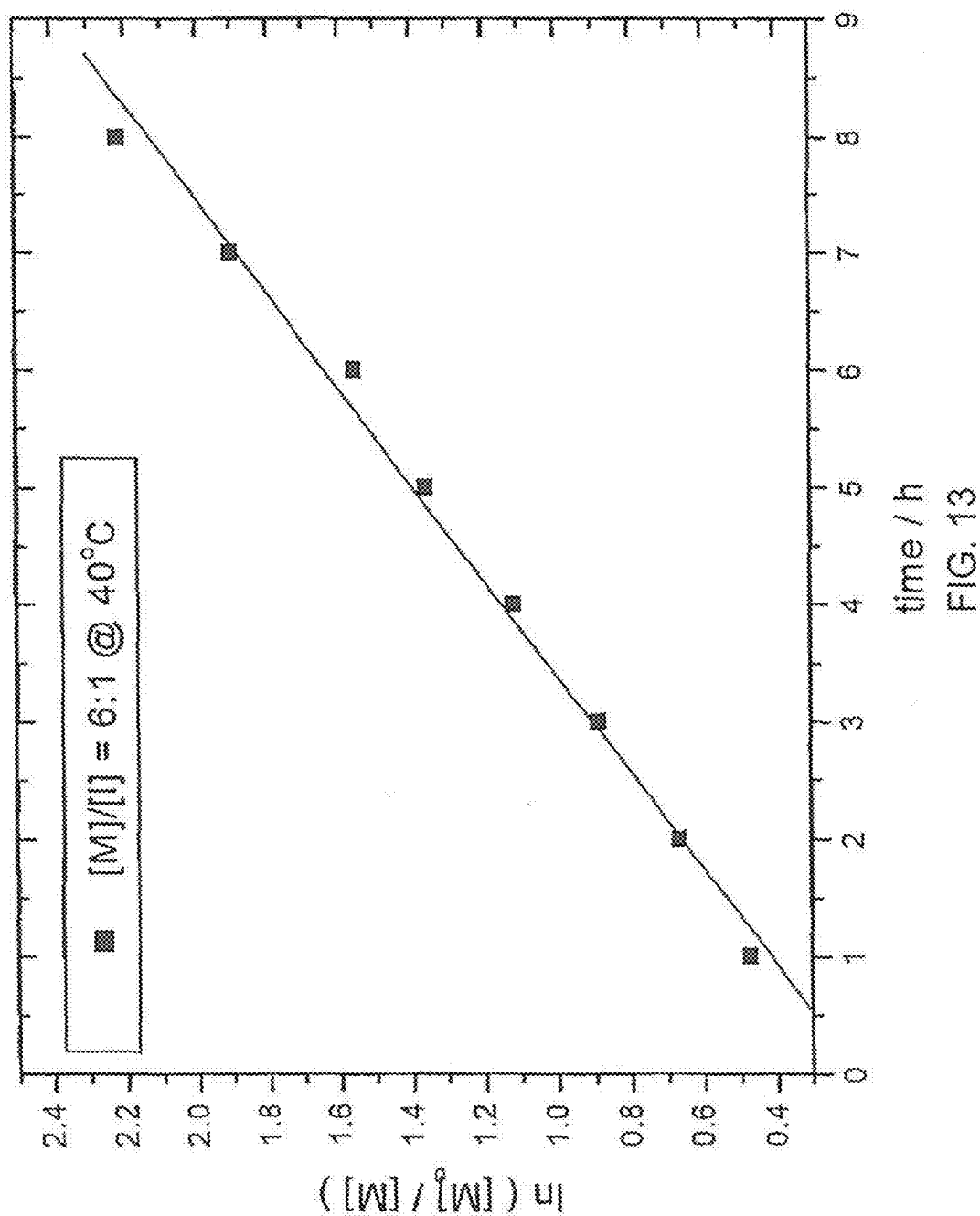

FIG. 13. Rate plot for TMM-LRP of MPEG(395)MA using initiator 14, [monomer]:[initiator]:[CuBr]:[L]=6:1:1:2.

Figure 14:
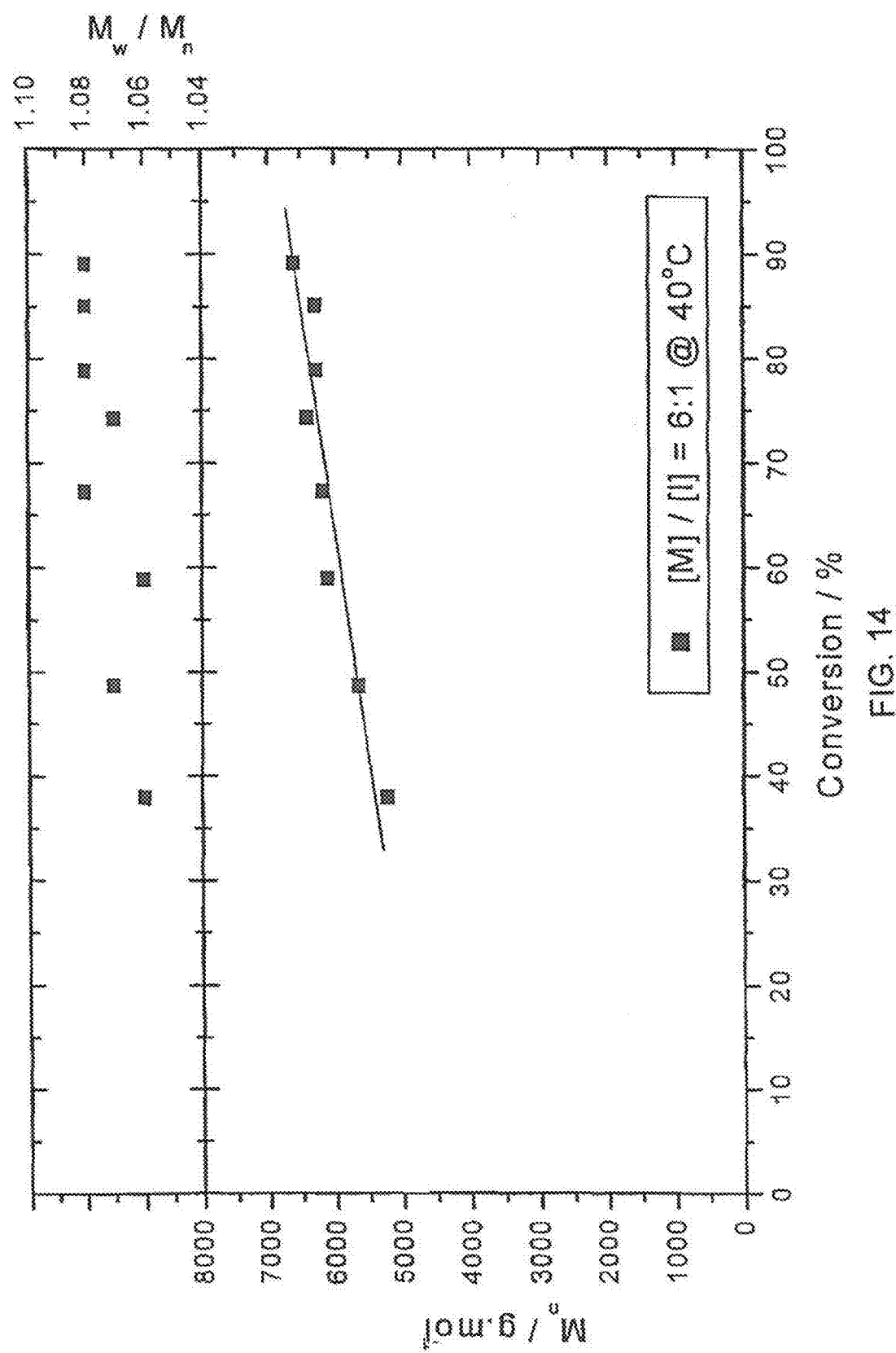

FIG. 14. Dependence of $M_n$ on conversion for TMM-LRP of MPEG(395)MA using initiator 14, [monomer]:[initiator]:[CuBr]:[L]=6:1:1:2.

Figure 15:
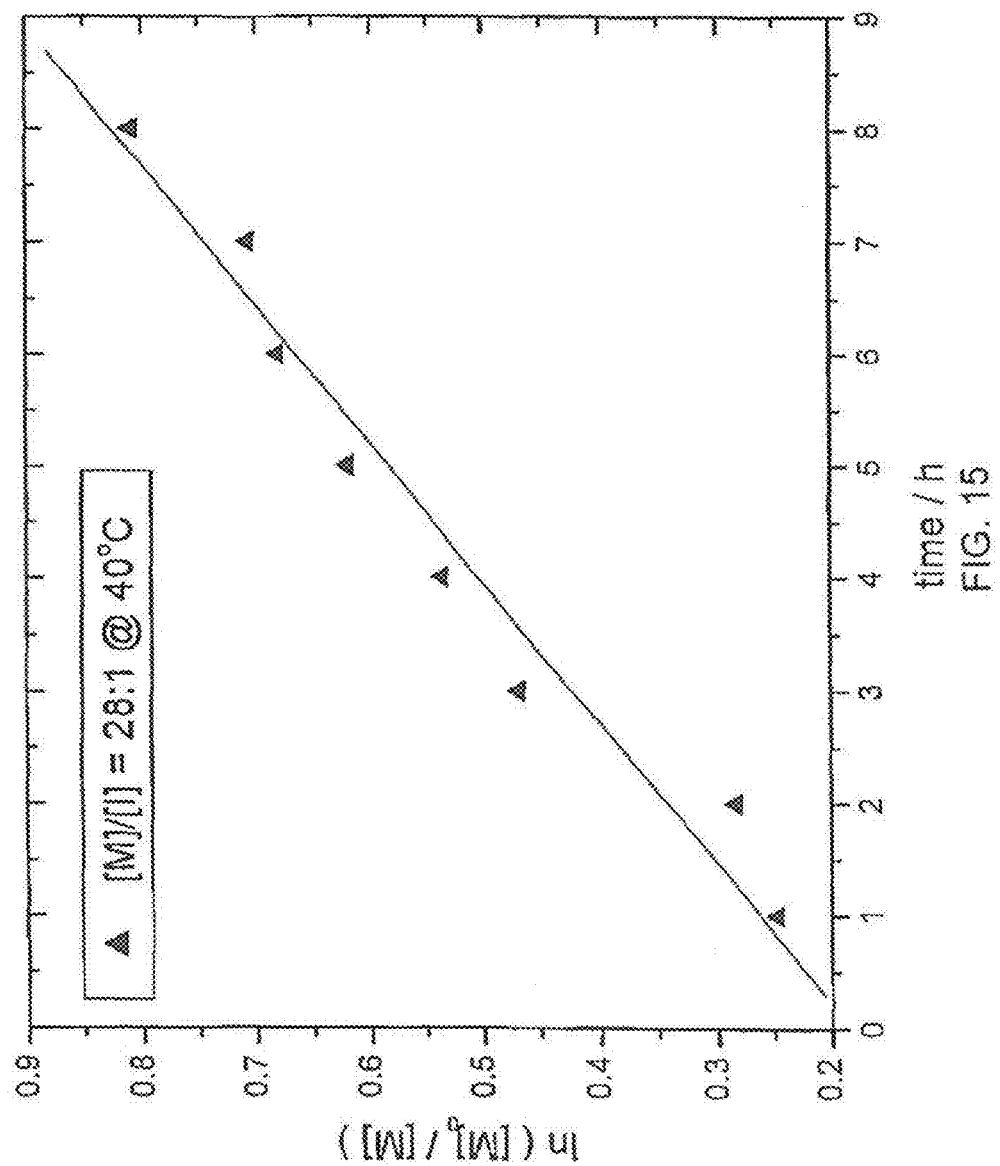
Figure 16:
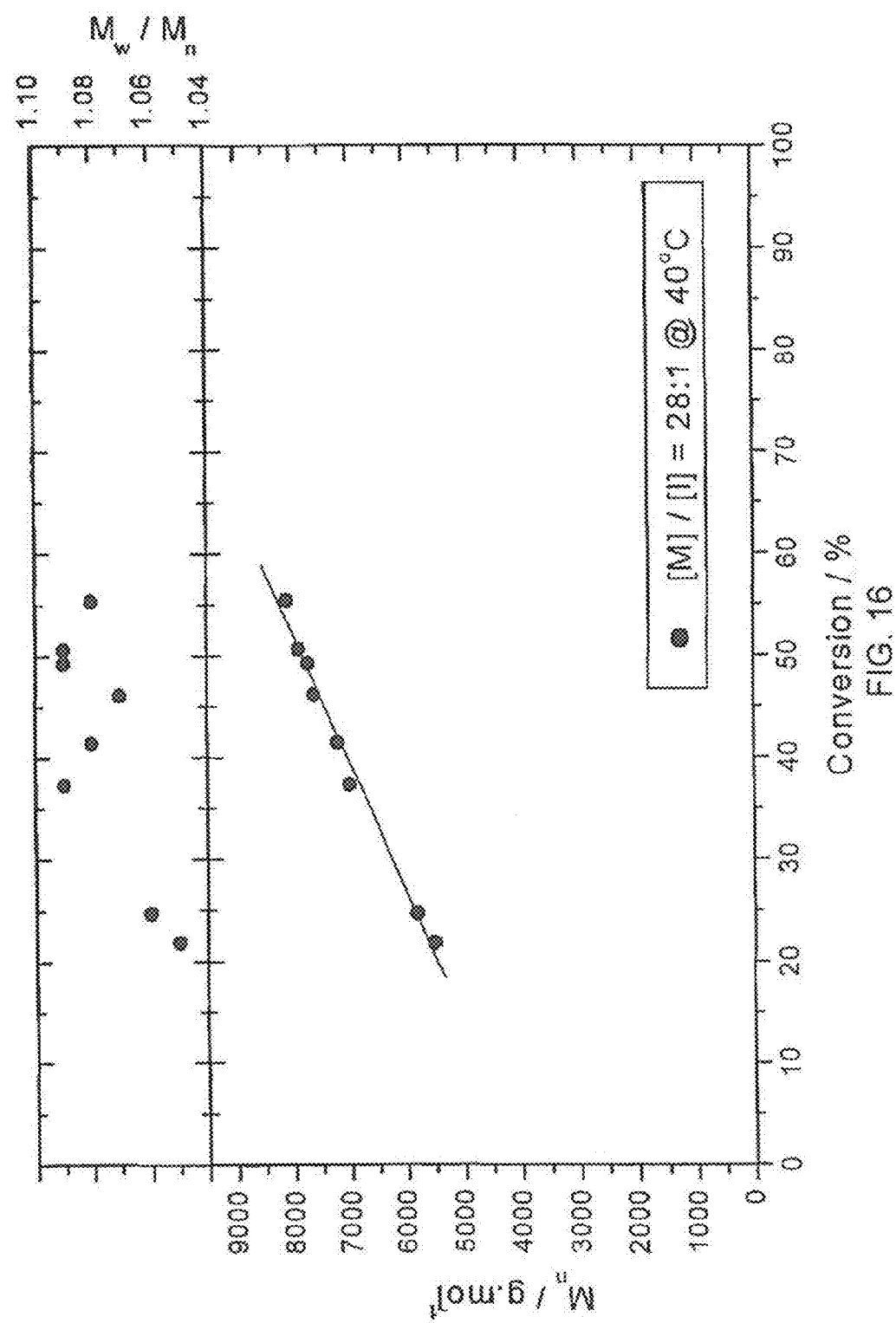

FIG. 15. Rate plot for TMM-LRP of MPEG(395)MA using initiator 14, [monomer]:[initiator]:[CuBr]:[L]=28:1:1:2, T 40° C.

FIG. 14. Dependence of $M_n$ on conversion for TMM-LRP of MPEG(395)MA, using initiator 14, [monomer]:[initiator]:[CuBr]:[L]=6:1:1:2, T=40° C.

Figure 17:
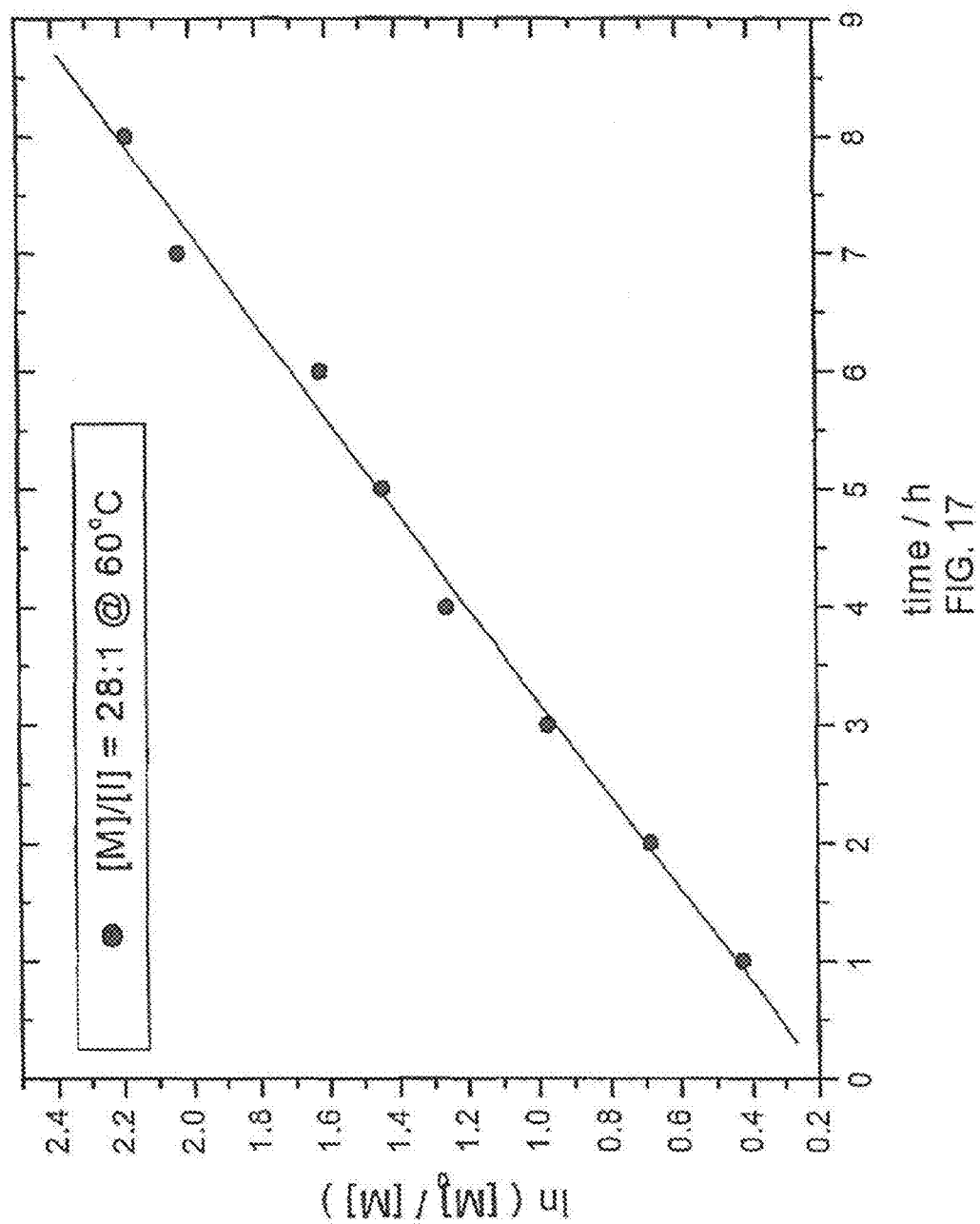

FIG. 17. Rate plot for TMM-LRP of MPEG(395)MA using initiator 14, [monomer]:[initiator]:[CuBr]: [L]=28:1:1:2, T=60° C.

Figure 18:
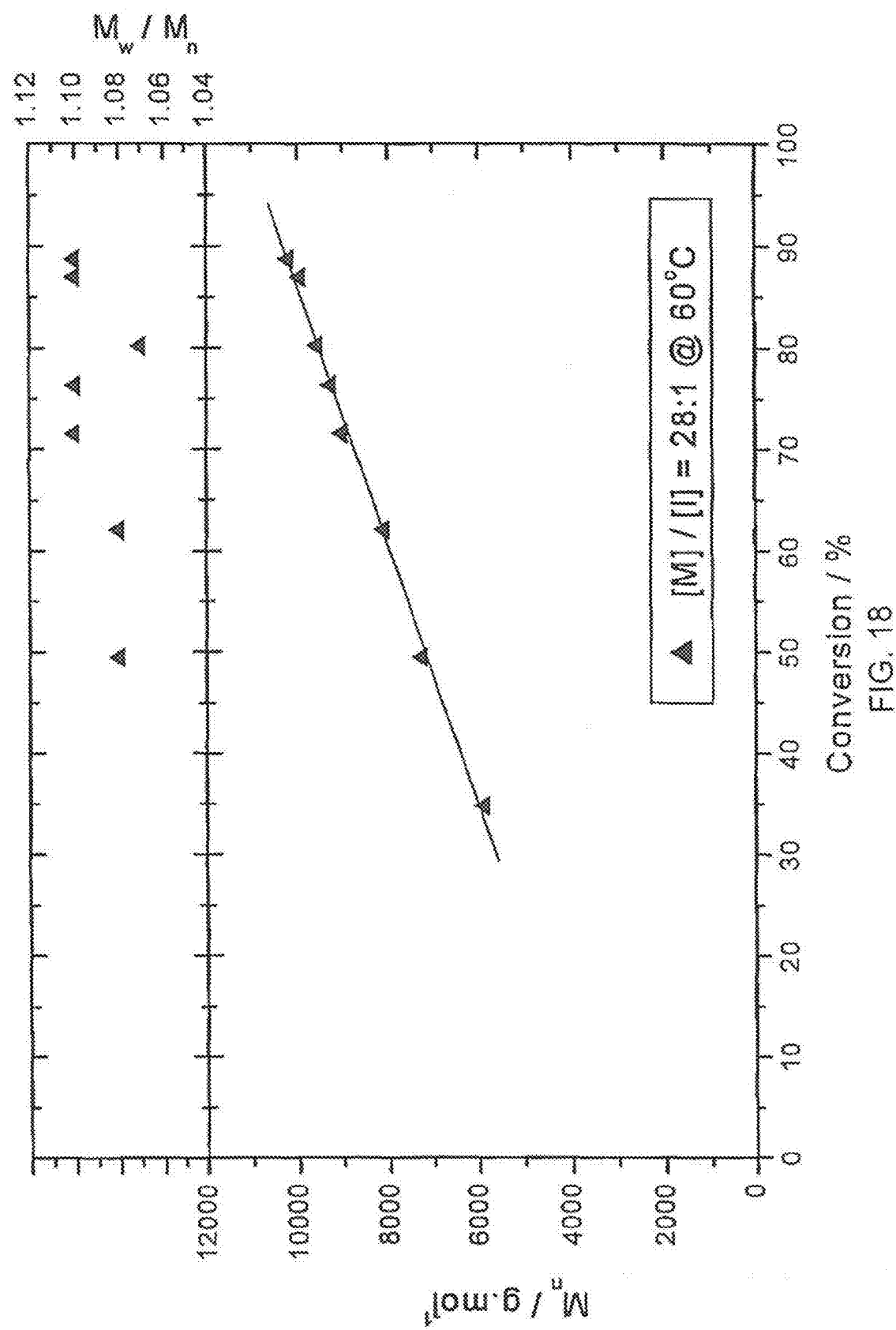

FIG. 18. Dependence of $M_n$ on conversion for TMM-LRP of MPEG(395)MA using initiator 14, [monomer]:[initiator]=6:1:1:2, T=60° C.

Figure 19:
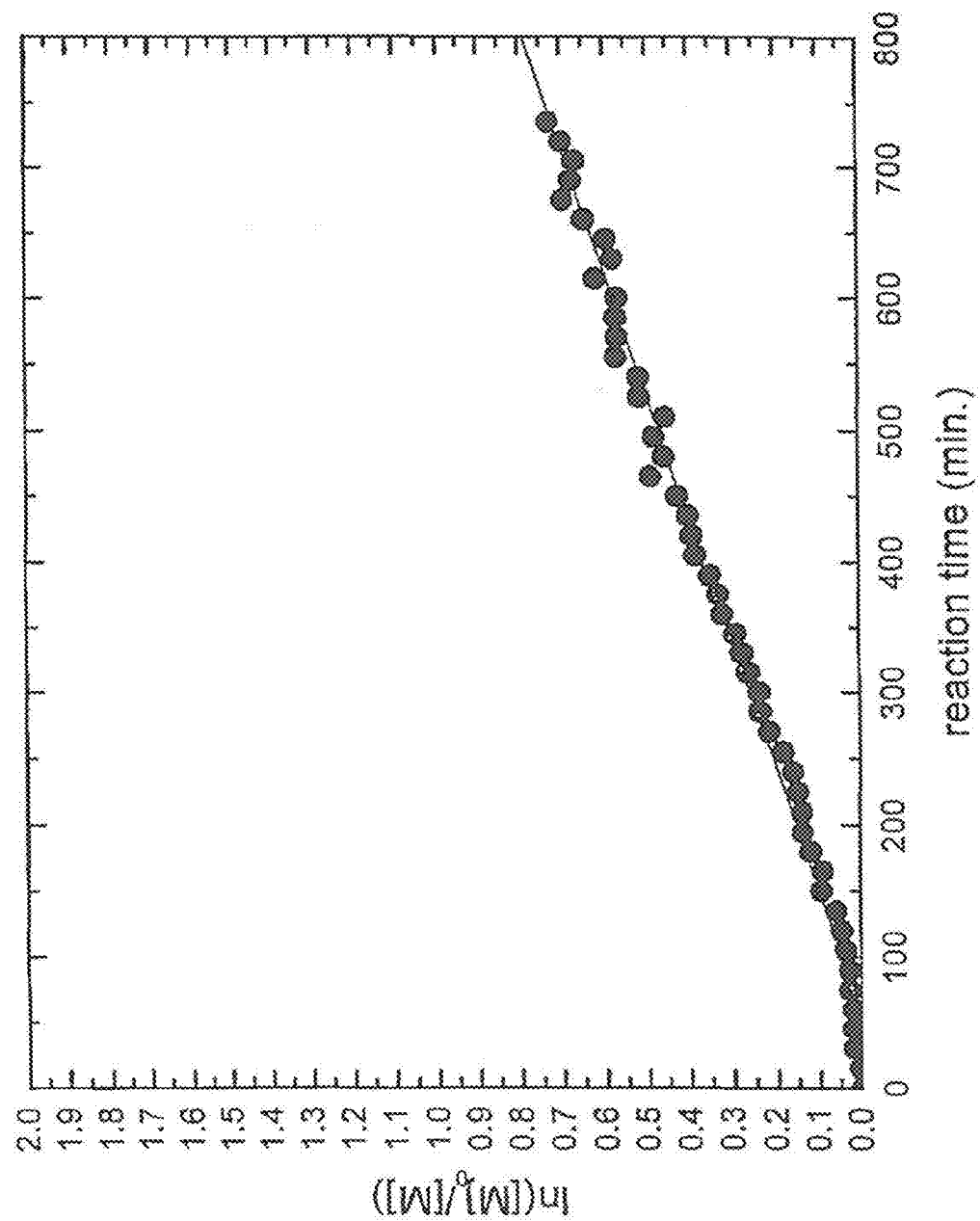

FIG. 19. Online $^1H$ NMR experiment: Rate plot for TMM-LRP of NWEG (395)MA using initiator 14, [monomer]: [initiator]:[CuBr]:[L]=10:1:1:2. T=40° C.

Figure 20:
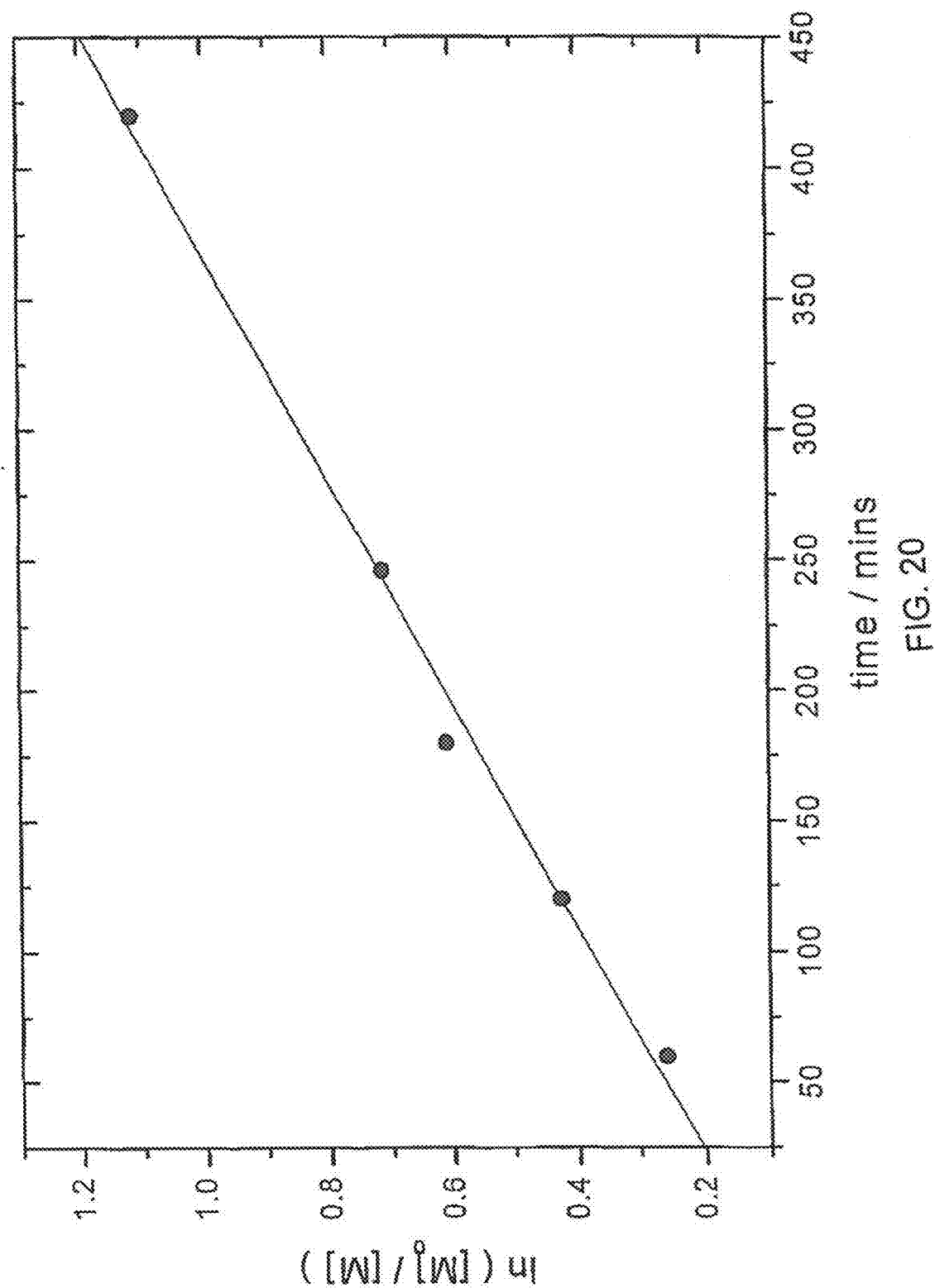

FIG. 20. Rate plot for TMM-LRP of MPEG(395)MA using initiator 15, [monomer]:[initiator]:[CuBr]:[L]=8:1:1:2. T=30° C.

Figure 21:
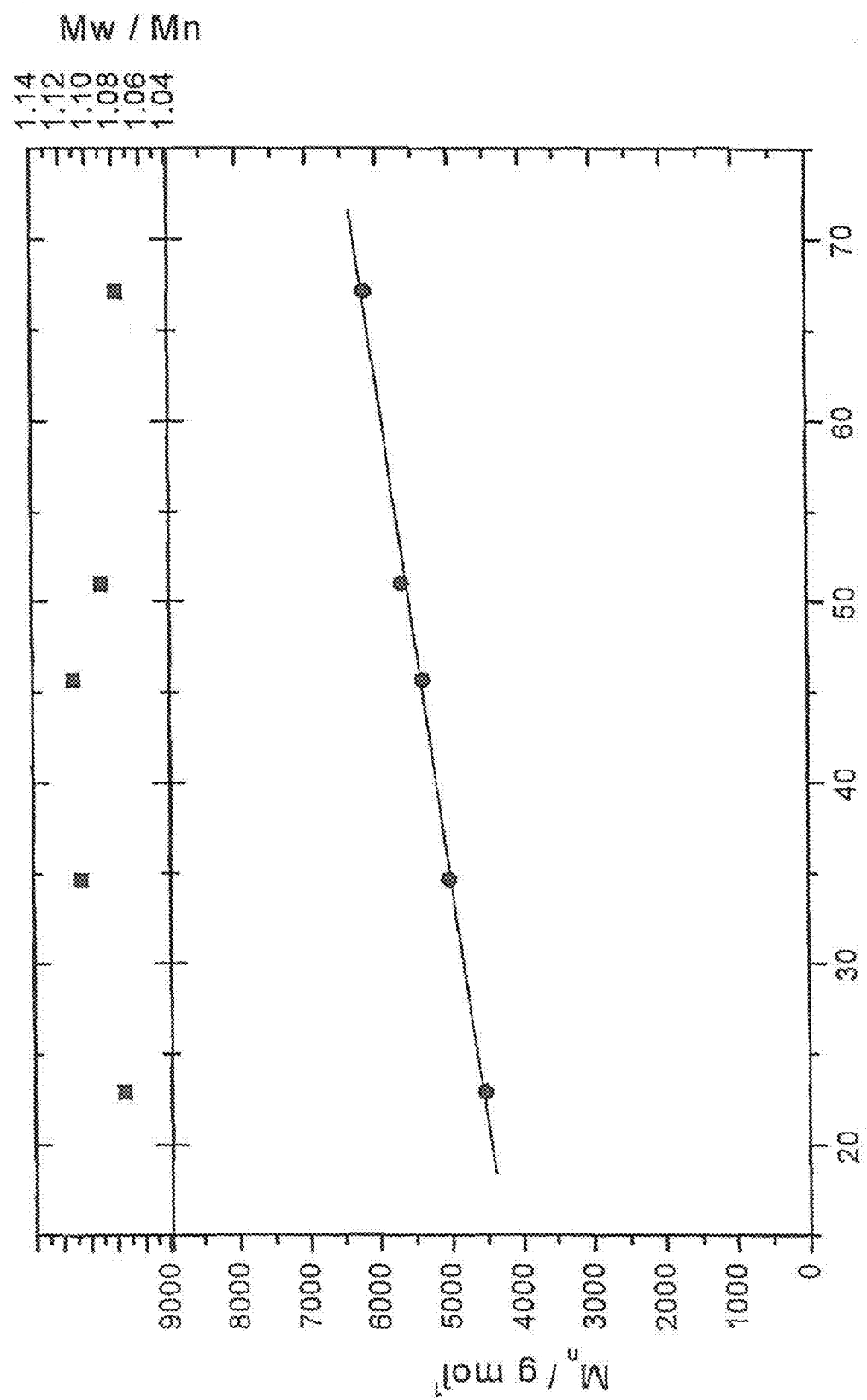

FIG. 21. Dependence of $M_n$ on conversion for TMM-LRP of MPEG(395)MA using initiator 15, [monomer]:[initiator]:[CuBr]:[L]=8:1:1:2, T=30° C.

Figure 22:
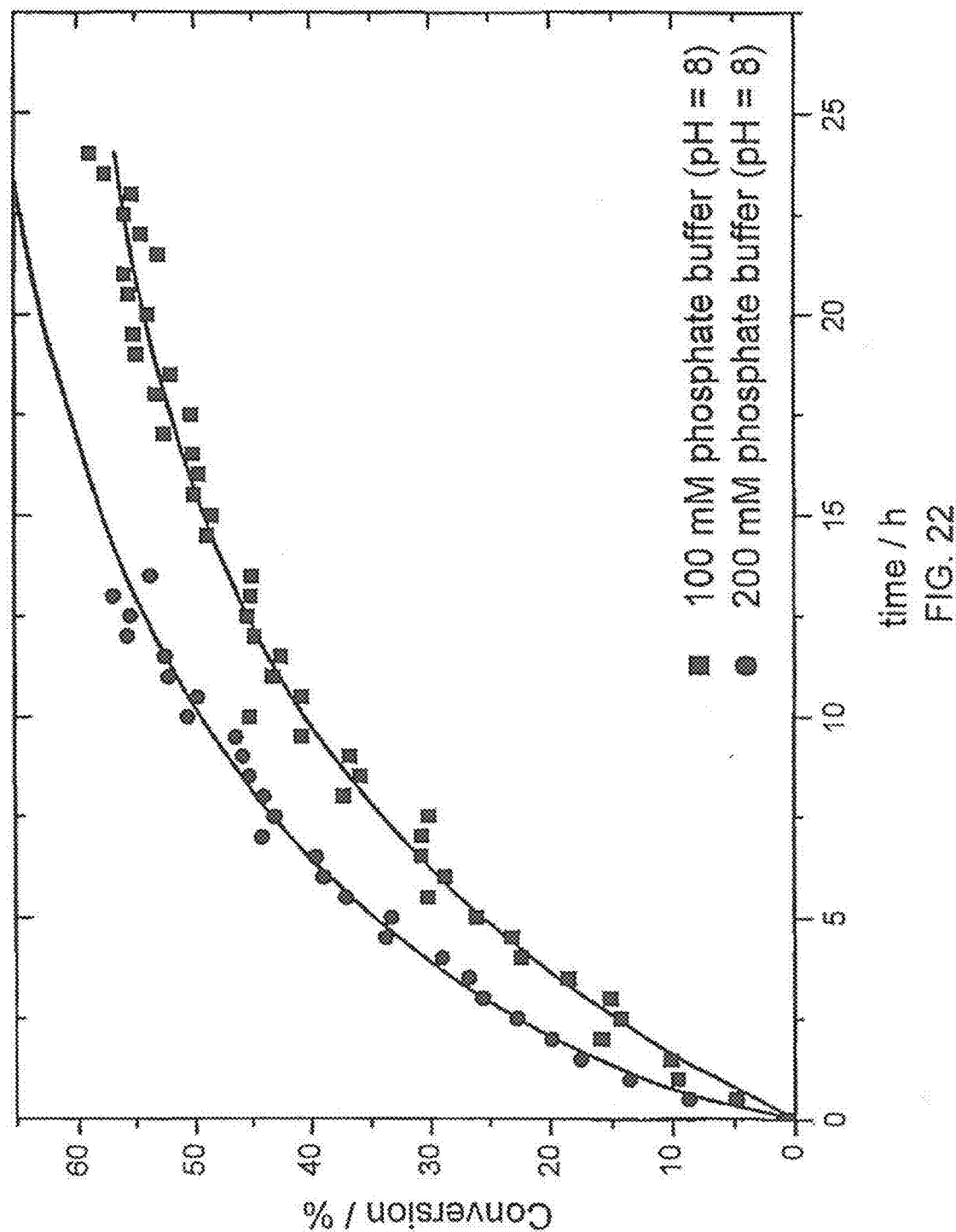

FIG. 22. Kinetic plot for the hydrolysis of N-succinimidyl terminated poly(MPEG(395)MA initiated by 8 in different buffers.

Figure 23:
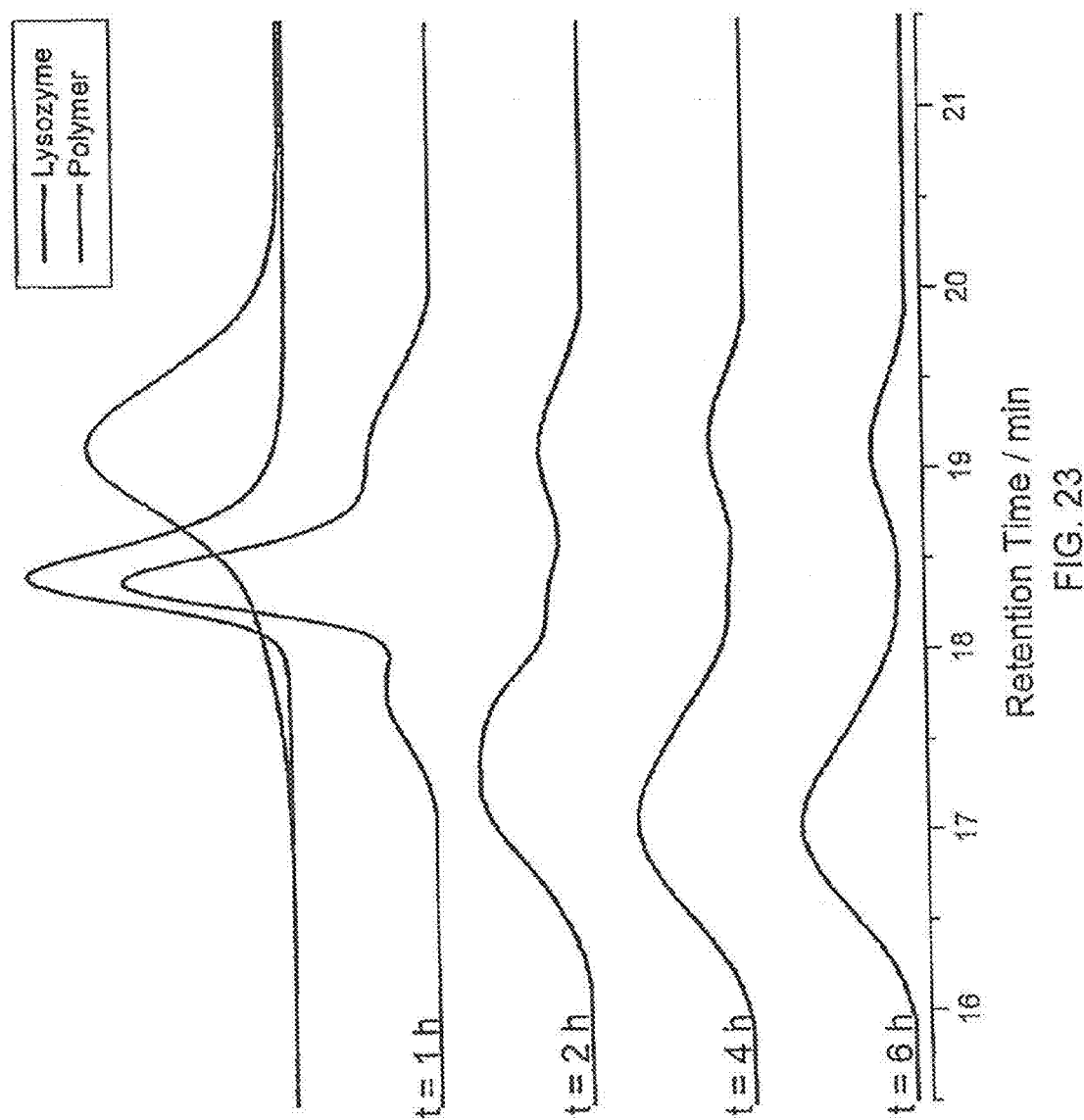

FIG. 23. HPLC traces for the reaction of succinimide terminated poly(MPEG(395)MA) prepared from initiator 8 ($M_n=6400$ g·mol$^{-1}$, $M_w/M_n=1.11$) with Lysozyme ([polymer]/[lysozyme] 20:1).

Figure 24:
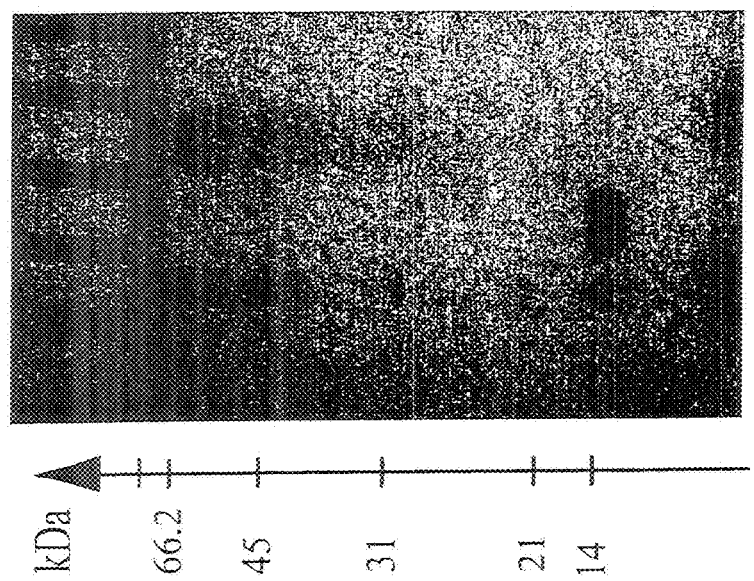

FIG. 24. SDS-PAGE for the conjugation of lysozyme with succinimide terminated poly(MPEG(395)MA) prepared from initiator 8 ($M_n=6400$ g·mol$^{-1}$, $M_w/M_n=1.11$) (20 equivalents).

Figure 25:
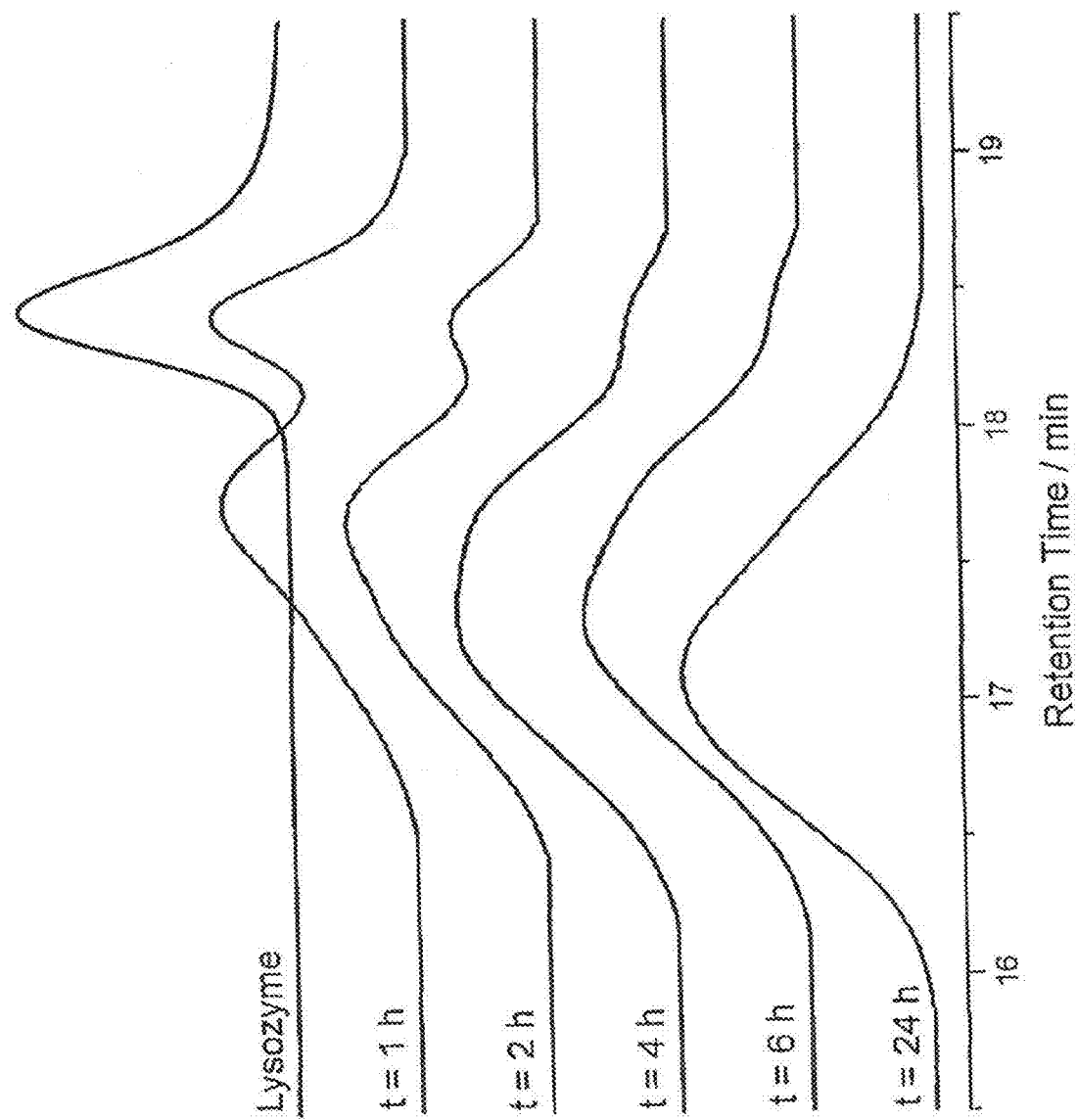

FIG. 25. HPLC traces for the reaction of succinimide terminated poly(MPEG(395)MA) prepared from initiator 8 ($M_n=6400$ g·mol$^{-1}$, $M_w/M_n=1.11$) with Lysozyme ([polymer]/[lysozyme] 5:1).

Figure 26:
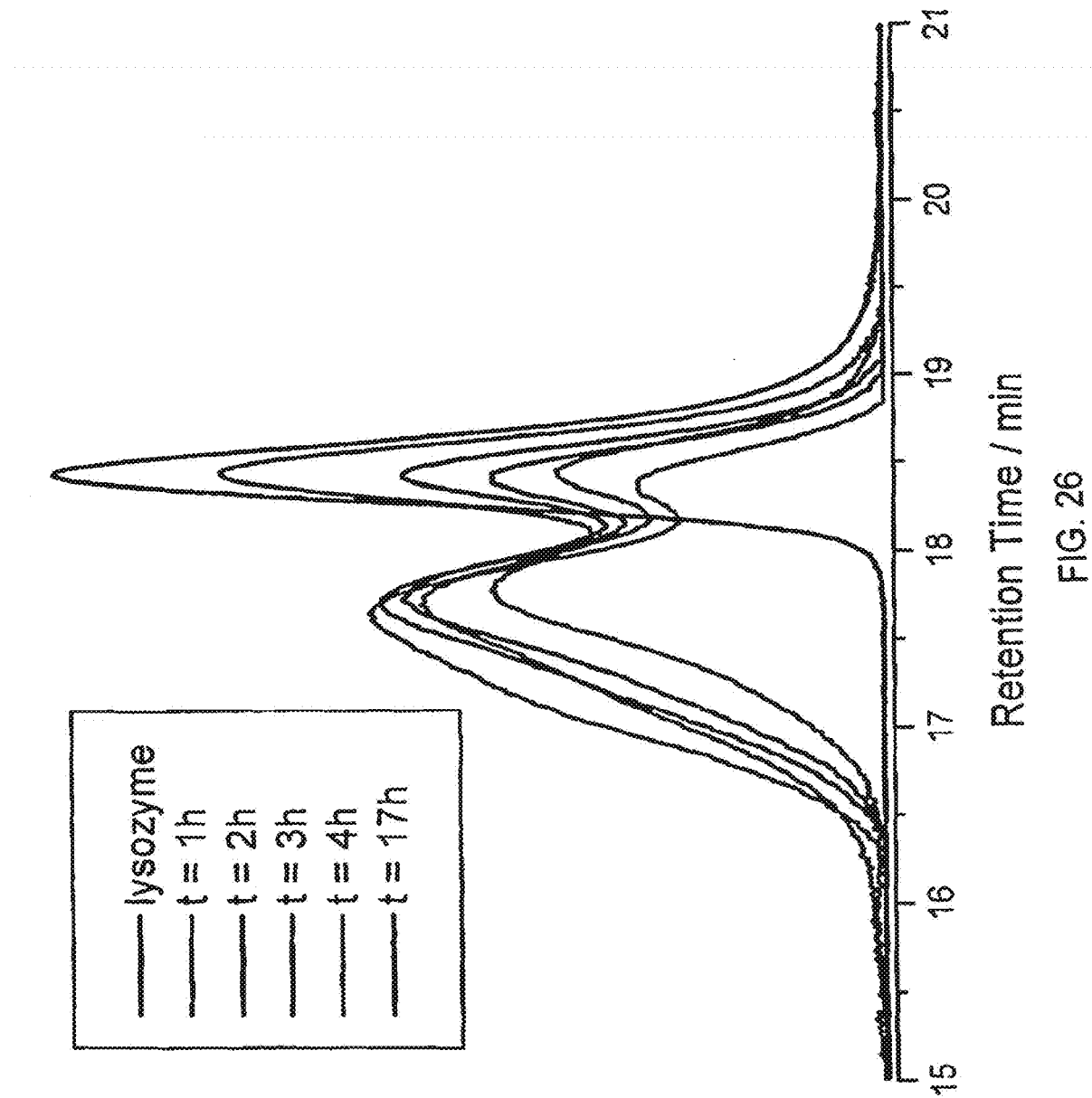

FIG. 26. HPLC traces for the reaction of succinimide terminated poly(MPEG(395)MA) prepared from initiator 8 ($M_n=6400$ g·mol$^{-1}$, $M_w/M_n=1.11$) with Lysozyme ([polymer]/[lysozyme] 2:1).

Figure 27:
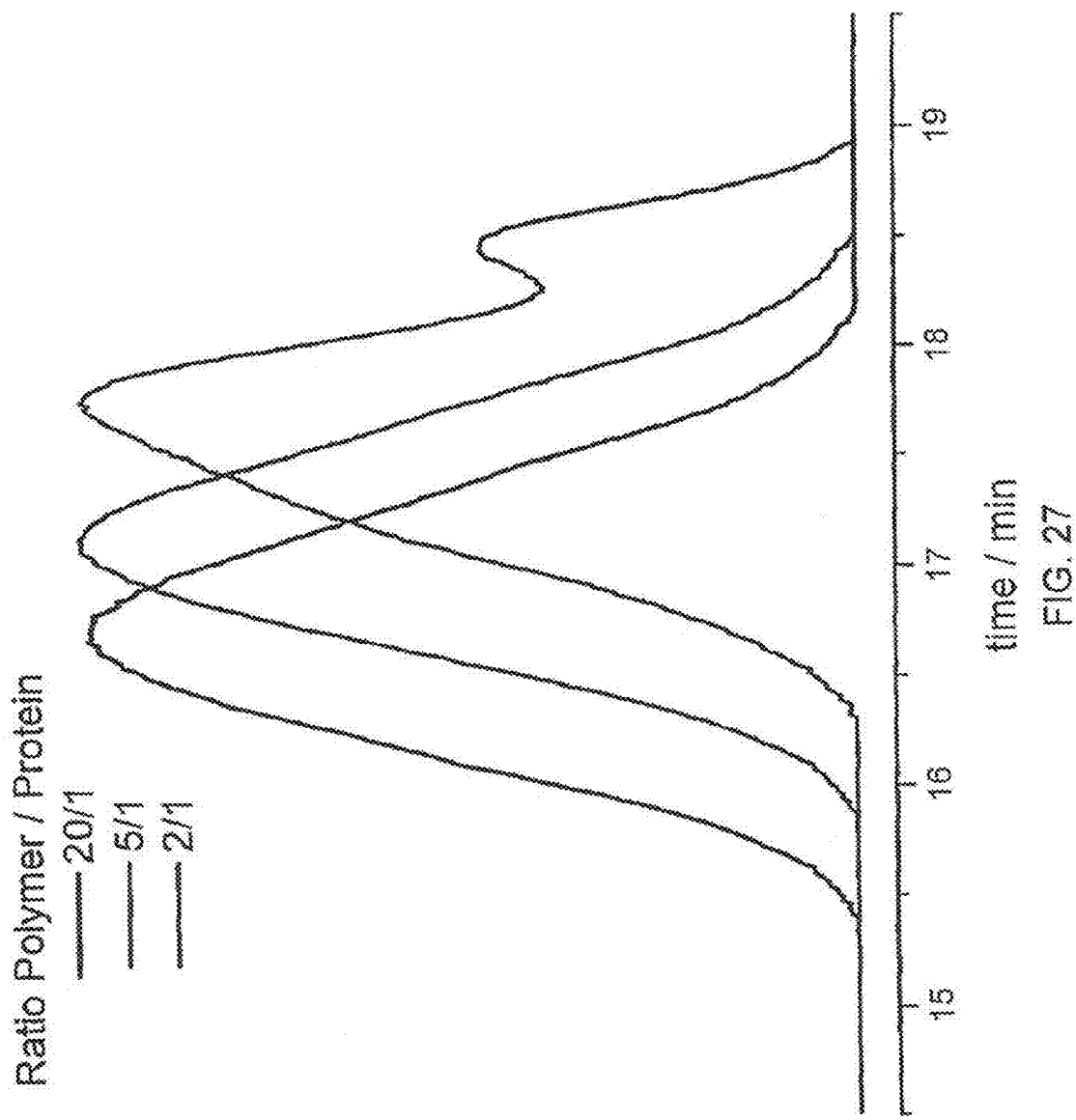

FIG. 27. Comparison of the HPLC traces of various conjugates of lysozyme obtained with different ratios of polymer/lysozyme using succinimide terminated poly(MPEG(395) MA) prepared from initiator 8.

Figure 28:
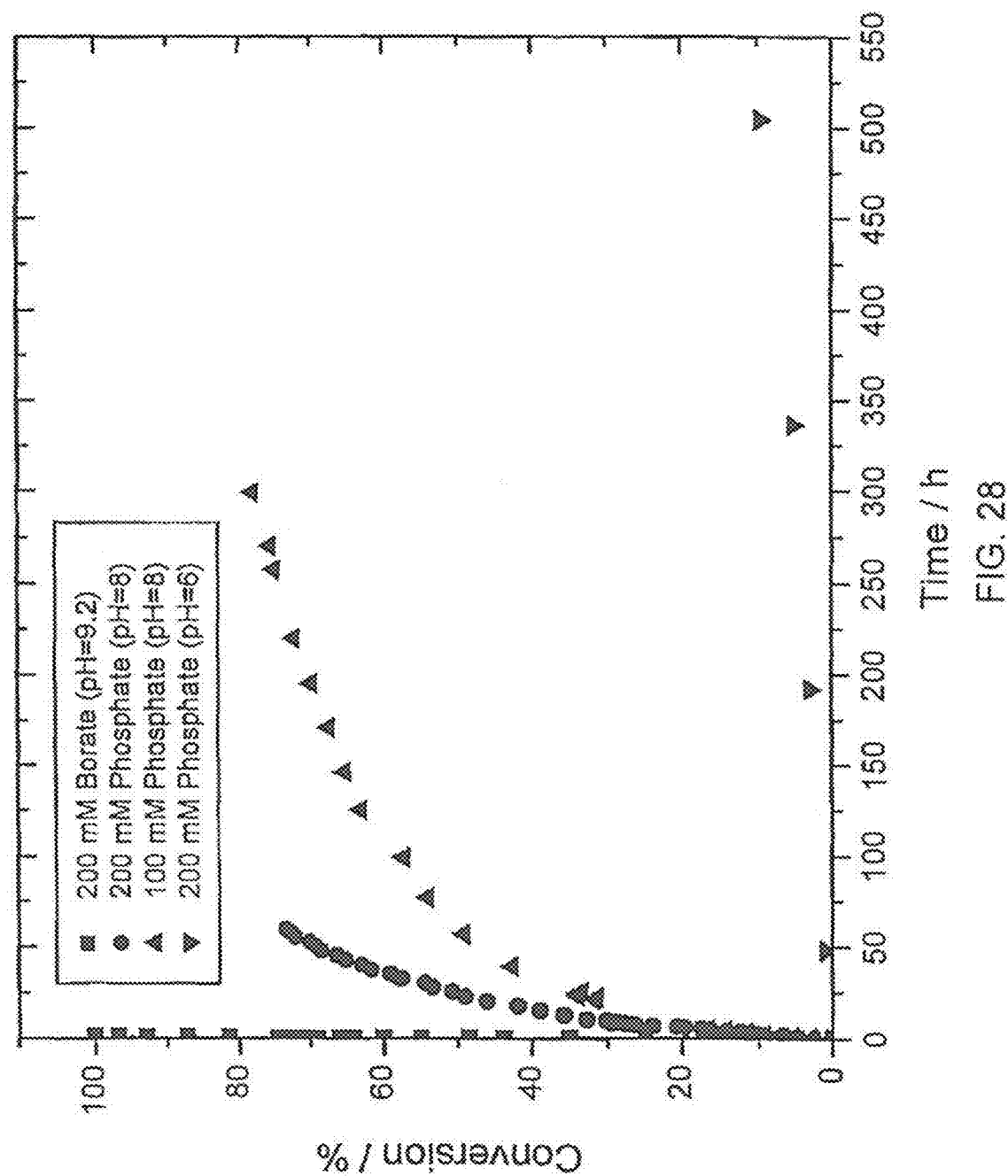

FIG. 28. Kinetic plot for the hydrolysis of the succinimide end group of poly(MPEG(395)MA) polymer initiated by 7 in different buffers.

Figure 29:
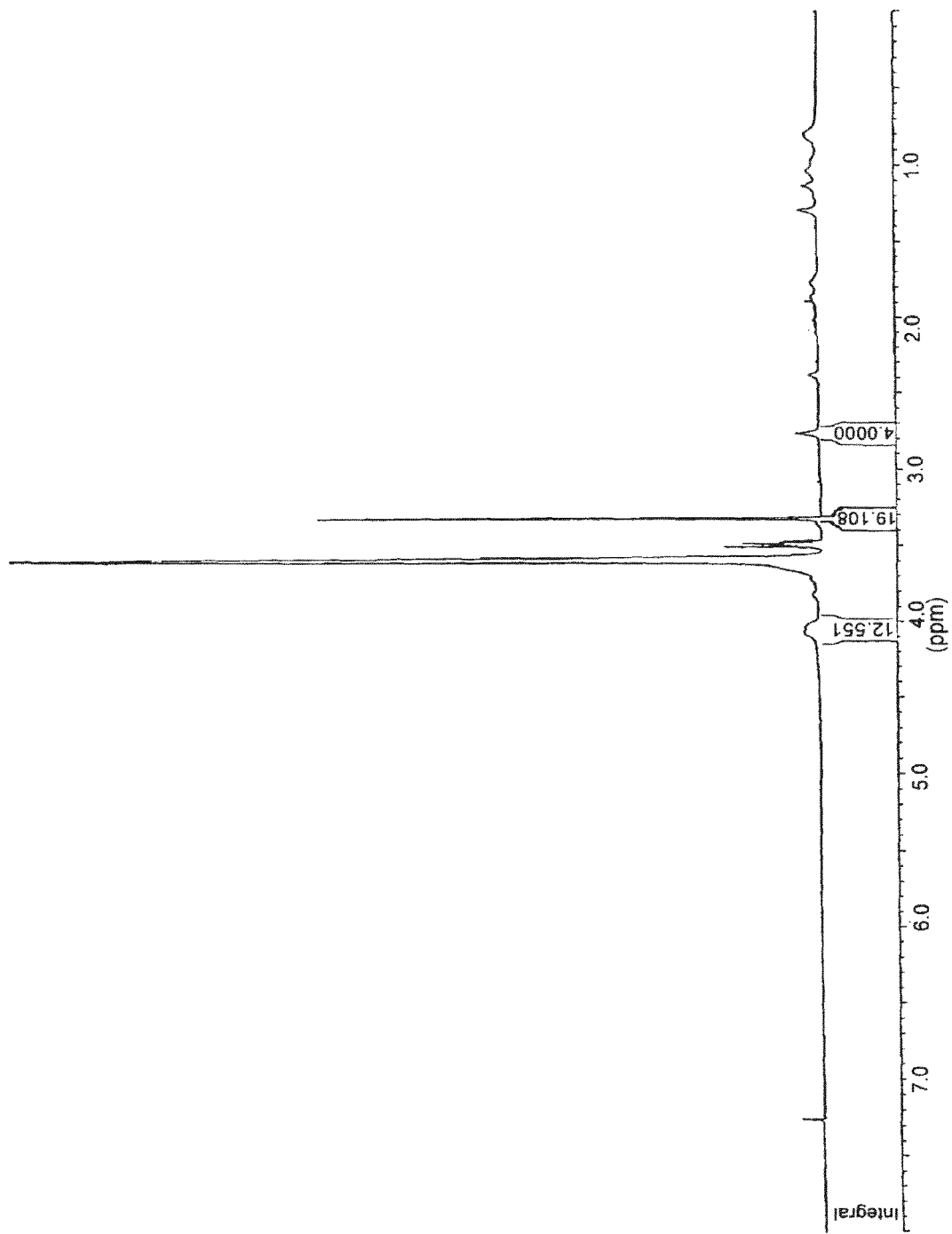

FIG. 29. $^1H$ NMR spectrum of a NHS eater functionalised (initiator 7) poly(MPEG(395)MA) ($M_n$, 2700 g·mol$^{-1}$, $M_w/M_n=1.12$).

Figure 30:
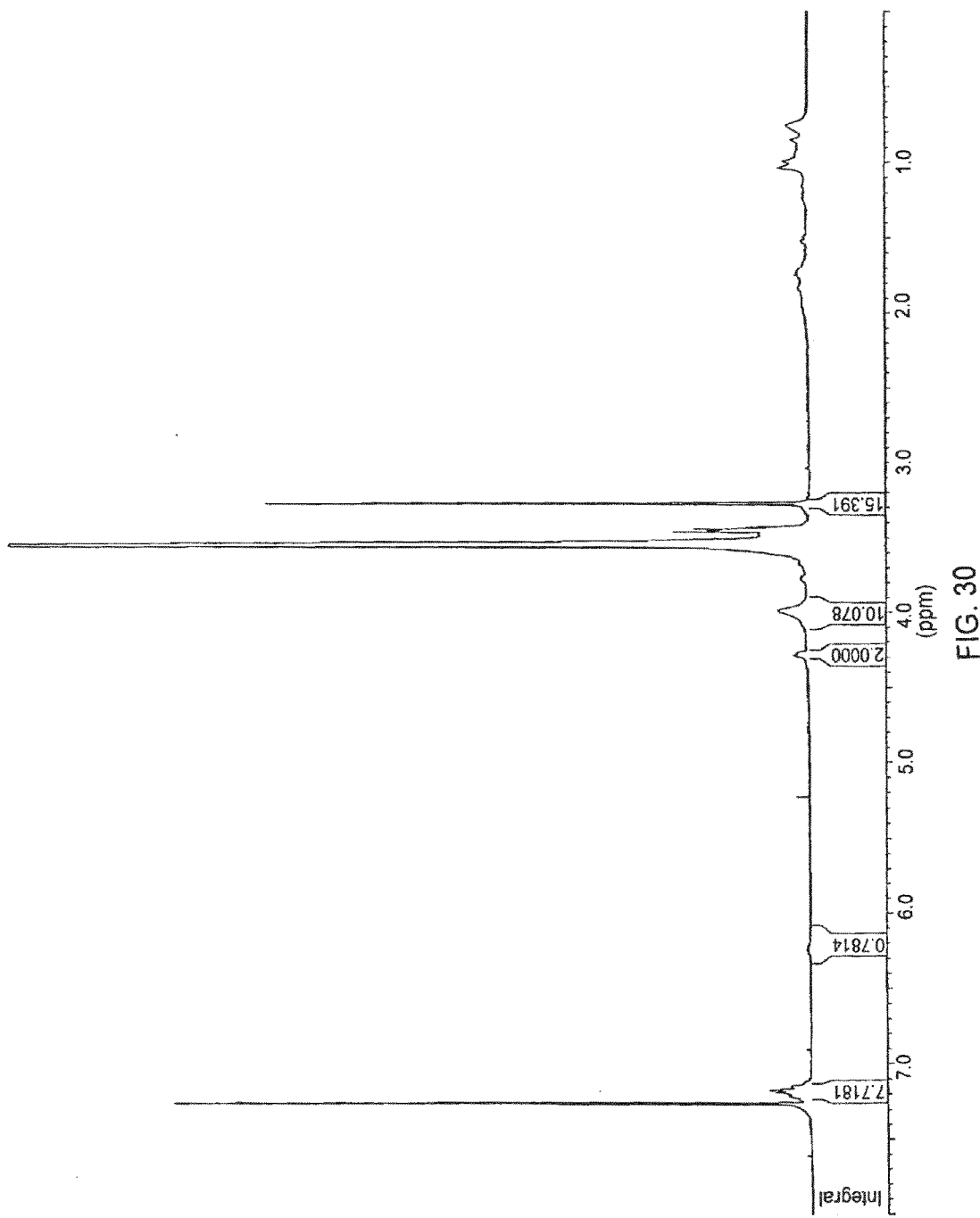

FIG. 30. $^1$H NMR spectrum of a N-benzylamide functionalised poly(MPEG(395)MA) ($M_n$=2880 g·mol$^{-1}$, $M_w/M_n$=1.15).

Figure 31:
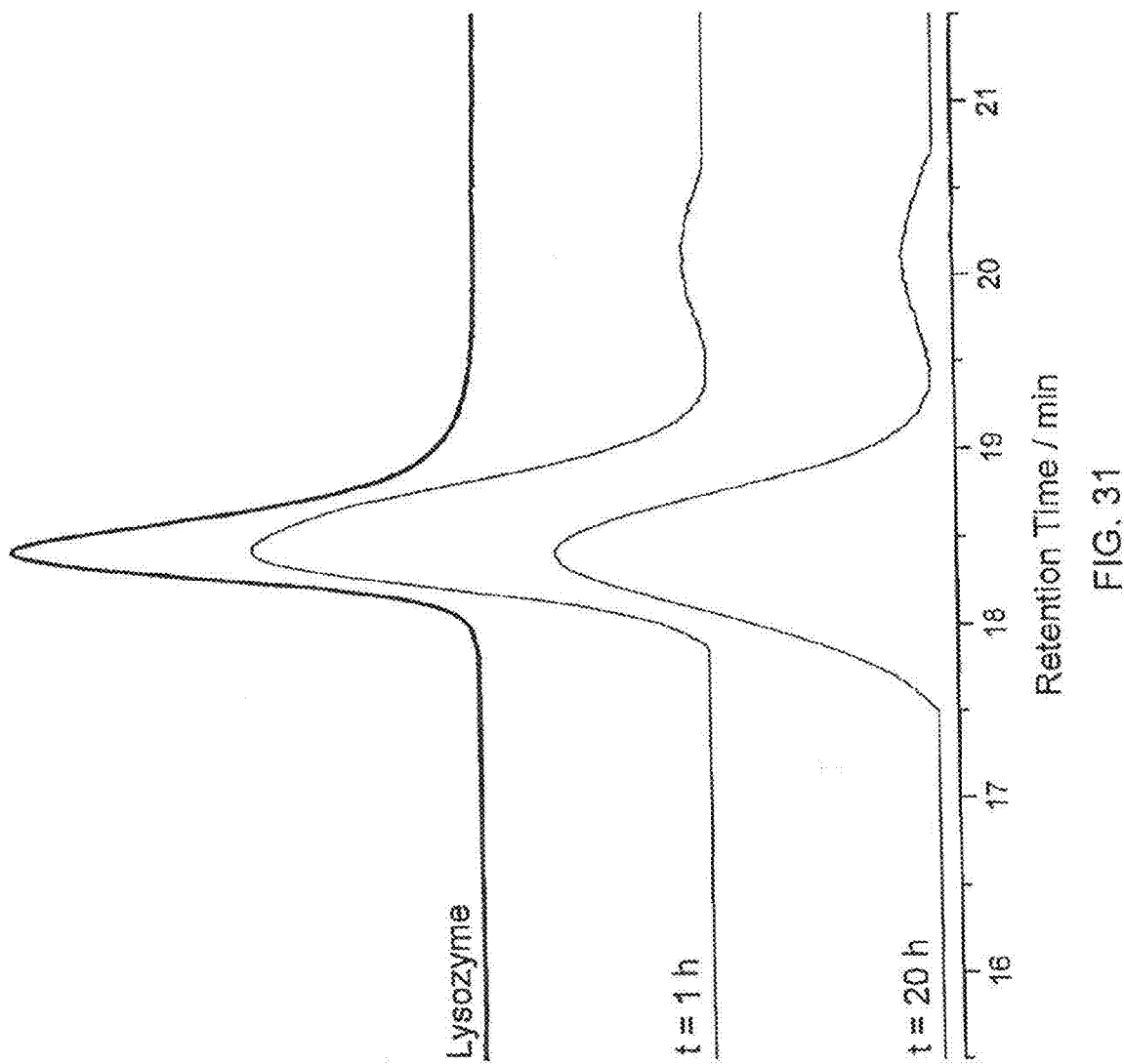

FIG. 31. HPLC traces for the reaction of poly(MPEG(395)MA) prepared from initiator 7 ($M_n$=2700 g·mol$^{-1}$, $M_w/M_n$=1.12) with lysozyme ([polymer]/[lysozyme] 30:1).

FIG. 32. SDS-PAGE for the conjugation of poly(MPEG (395)MA) prepared from initiator 7 with lysozyme at different reaction time and different ratio polymer/protein (a) 5/1, (b) 10/1 and (c) 30/1.

Figure 33:
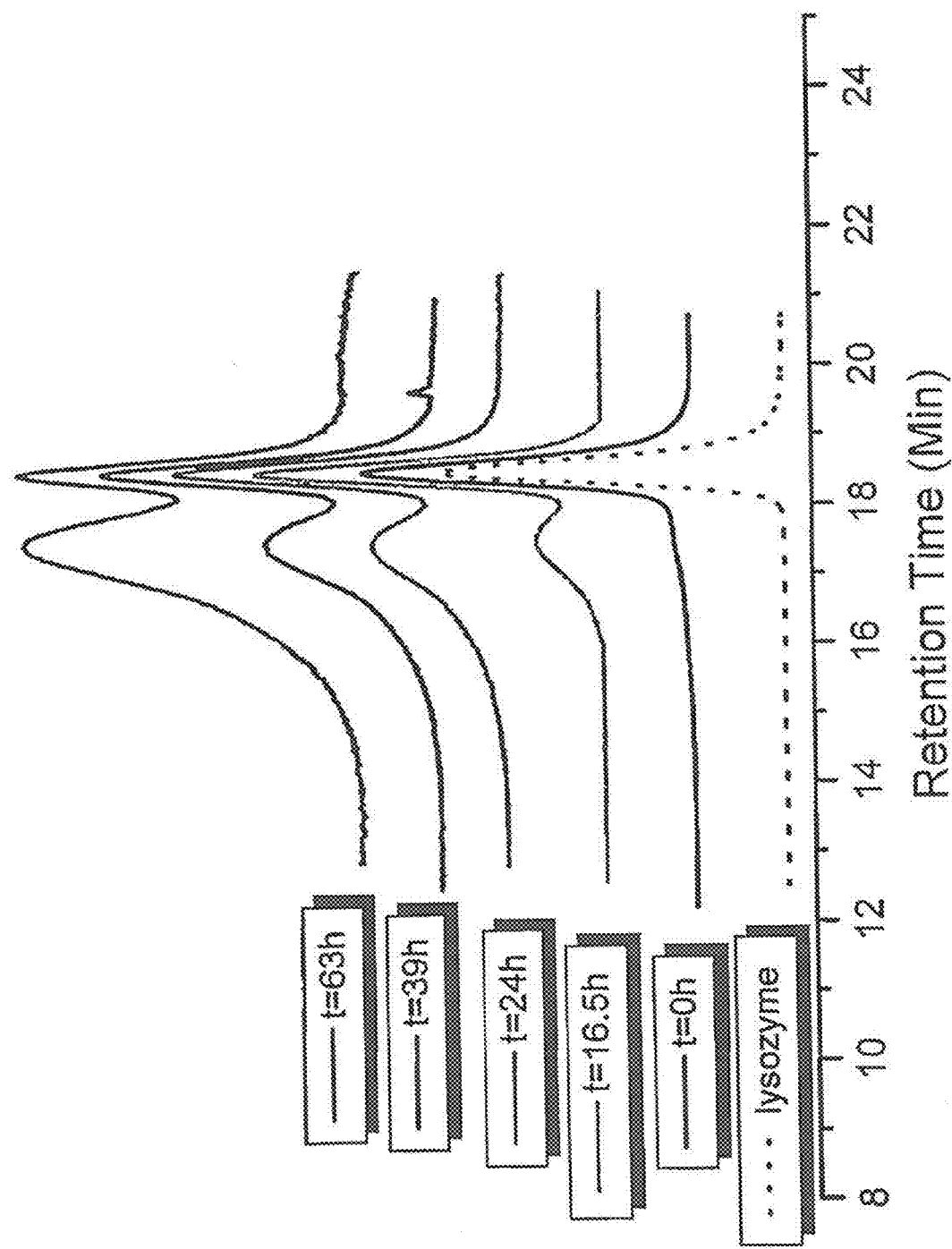

FIG. 33. SEC-HPLC chromatography of the conjugation reaction of Lysozyme with the aldehyde-terminated polymer ($M_n$~22,000 PDI 1.09).

Figure 34:
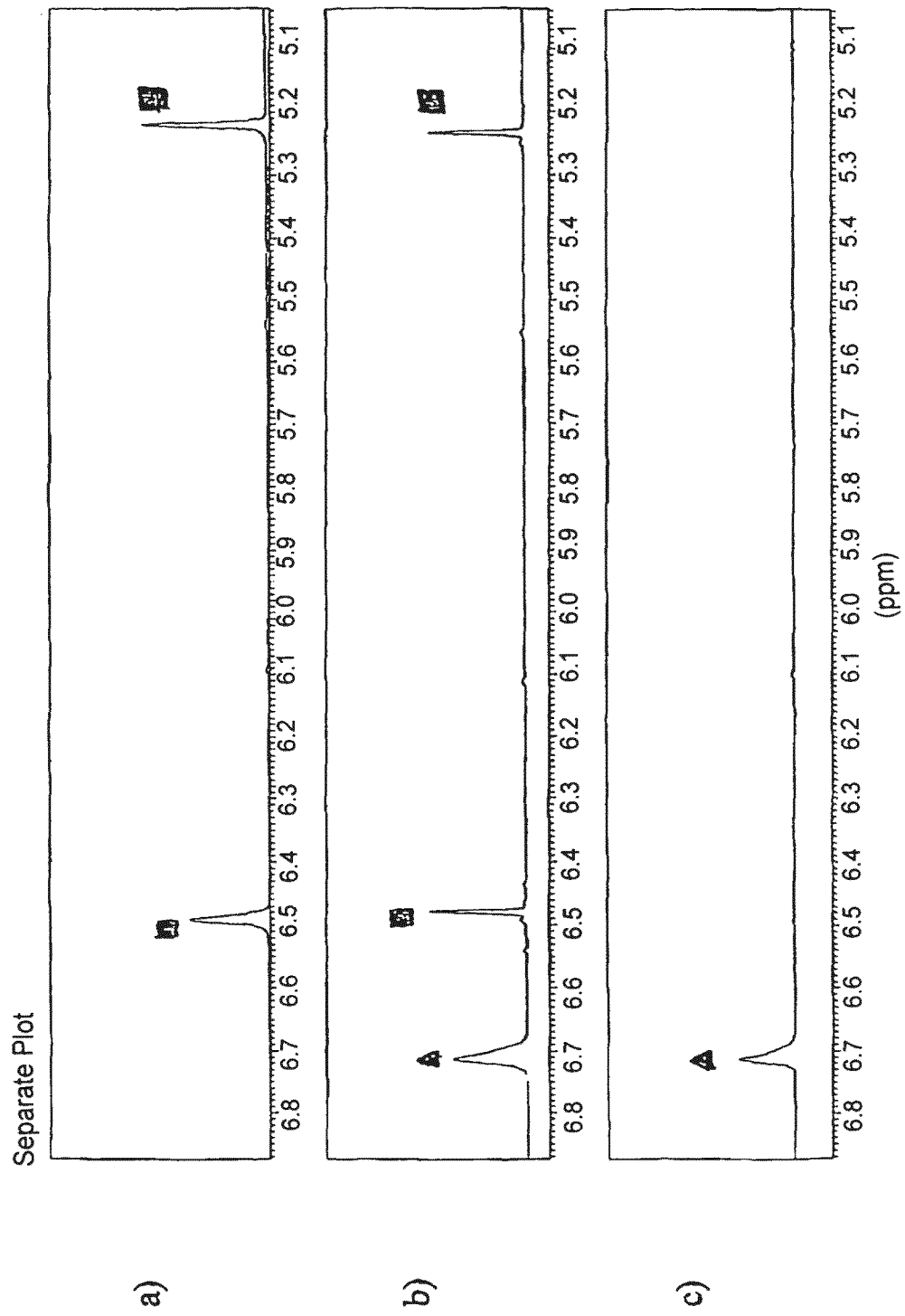

FIG. 34. Retro-Diels-Alder reaction: (●="initiator" and ▲=maleimido signals) a) t=0; b) t=3.5 h; c) t=7 h.

Synthesis Of N-[2-(2'-Bromo-2'-Methylpropionyloxy)-Ethyl]Phthalimide, 6.

N-(2-hydroxyethyl)phthalimide (Aldrich, 99%) (19.12 g, 0.1 mol) was dissolved in anhydrous THF (350 mL) with triethylamine (28.1 mL, 0.2 mot) under nitrogen in a 500 mL round-bottomed flask equipped with a magnetic stirrer. The flask was cooled to 0° C. with an ice bath before the dropwise addition of 2-bromoisobutyryl bromide (13.9 mL, 0.11 mol). The mixture was stirred for 45 minutes and allowed to reach room temperature. Subsequently the reaction mixture was poured into an excess of cold water and extracted with diethyl ether (3×50 mL). The organic layer was washed with a saturated aqueous solution of $Na_2CO_3$ (3×50 mL), acidified water (pH=4.5, 3×50 mL), and again the saturated aqueous solution of $Na_2CO_3$ (3×50 mL). The organic layer was dried over anhydrous $MgSO_4$ and filtered. Finally the solvent was removed under reduced pressure by using the rotary evaporator in order to isolate the title compound (30.6 g, yield 90%) as a yellowish solid.

m.p. 63-65° C., IR (solid, ATR cell) ν (cm$^{-1}$) 1774 ($C_{cycl}$=O), 1705 (C=O); $^1$H NMR (CDCl$_3$, 298 K, 300 MHz) δ 1.81 (s, 6H, C(CH$_3$)$_2$Br), 3.95 (t, 2H, J=5.3 Hz, CH$_2$N), 4.35 (t, 2H, J=5.4 Hz, CH$_2$O), 7.67 (m, 2H, CH Ar), 7.78 (m, 2H, CH Ar). $^{13}$C NMR (CDCl$_3$, 298 K, 75 MHz) δ 31.00 (2C, C(CH$_3$)$_2$Br), 37.12 (1C, CH$_2$N), 55.92 (1C, C(CH$_3$)$_2$Br) 63.42 (1C, CH$_2$O), 123.78 (2C, CH Ar), 132.35 (1C, C Ar), 133.54 (2C, CH Ar), 168.40 (2C, $C_{cycl}$=O), 171.87 (1C, C=O).

Synthesis Of N-(2-Bromo-2-Methylpropionyloxy)Succinimide, 7

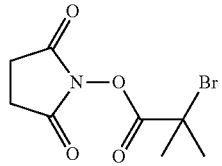

This was prepared from N-hydroxysuccinimide (NHS) using a similar procedure to that given above for the synthesis of compound 6. The solvent used in this case was anhydrous dichloromethane as NHS is insoluble in THF. The title compound was obtained in 85% yield as a white solid.

m.p. 72-74° C.; IR (solid, ATR cell) ν (cm$^{-1}$) 1772 ($C_{cycl}$=O), 1728 (C=O); $^1$H NMR (CDCl$_3$, 298 K, 300 MHz) δ 2.08 (s, 6H, C(CH$_3$)$_2$Br), 2.87 (a, 4H, CH$_2$). $^{13}$C NMR (CDCl$_3$, 298 K 75 MHz) δ 26.03 (2C, CH), 31.09 (2C, C(CH$_3$)$_2$Br), 51.60 (1C, C(CH$_3$)$_2$Br), 167.89 (1C, C=O) 169.02 (2C, $C_{cycl}$=O), MS (+EI), (m/z) 266, 265, 156, 151, 149, 123, 121, 116, 115, 91, 87, 70, 69. Anal, Calcd for C$_8$H$_{10}$NO$_4$Br: C=36.39; H=3.82; N=5.30, Br=30.26. Found: C=36.35; H=3.82; N=5.03; Br=30.17.

4-[(4-Chloro-6-Methoxy-1,3,5-Triazin-2-11)Amino] Phenol, 4

A solution of 2,4-dichloro-6-methoxy-1,3,5-triazine[29] (9.00 g, 50.0 mmol) in 100 mL of acetone was cooled to 0° C. and, under stirring, solid 4-aminophenol (5.46 g, 50.0 mmol was added in small portions over ea. 2 min. The white suspension was then left to warm to ambient temperature and stirred for further 1 h, whilst being neutralized with a 2 M aqueous solution of $Na_2CO_3$. The mixture was then poured into 500 mL of ice/water and the resulting white precipitate was filtered and dried, to give 9.60 g (38.0 mmol, yield 76%) of 4-[(4-chloro-6-methoxy-1,3,5-triazin-2-yl)amino]phenol that can be used for the next step without further purifications. An analytical sample was obtained by flash chromatography (CC, SiO$_2$, petroleum ether/Et$_2$O 1:1, R$_f$=0.14). The NMR analysis (d$_6$-DMSO) revealed the presence, in solution, of 2 rotational isomers (molar ratio 7:3).

m.p. 172° C. dec.; IR ν$_{(NH)}$ 3476 cm$^{-1}$. ν$_{(OH)}$ 3269 cm$^{-1}$.

Major isomer $^1$H NMR (d$_6$-DMSO, 298K, 300 MHz) δ 3.94 (s, 3H, OCH$_3$); 6.79 (d, J=8.8 Hz, 2H, CH Ar), 7.48 (d, J=8.8 Hz, 2H, CH Ar), 9.40 (s, 1H, OH), 10.46 (s, 1H, NH); $^{13}$C{$^1$H}NMR (d$_6$-DMSO, 298K, 75 MHz) δ 55.52 (1C, OCH$_3$); 115.46 (2C, CH Ar), 123.91 (2C, CH Ar), 129.49 (1C, C Ar), 154.44 (1C, C Ar), 164.81 (1C, C Ar), 169.57 (1C, C Ar), 171.23 (1C, C Ar).

Minor isomer $^1$H NMR (d$_6$-DMSO, 298K, 300 MHz) δ 3.96 (s, 3H, OCH$_3$); 6.79 (d, J=8.9 Hz, 2H, CH Ar), 7.39 (d, J=8.9 Hz, 2H, CH Ar), 9.42 (bs, 1H, OH), 10.10.32 (s, 1H, NH); $^{13}$C{$^1$H} NMR (d$_6$-DMSO, 298 K, 75 MHz) δ 55.10 (1C, OCH$_3$); 115.46 (2C, CH Ar), 123.03 (2C, CH Ar), 129.26 (1C, C Ar), 154.76 (1C, C Ar), 165.20 (1C, C Ar), 170.48 (1C, C Ar), 170.64 (1C, C Ar); Anal. Calcd for C$_{10}$H$_9$CN$_4$O$_2$: C$^{=47.54}$, H=3.59, N=22.18, Cl=14.03. Found: C=47.57, H=3.55, N=22.10, Cl=14.8.

14-[(4-Chloro-6-Methoxy-1,3,5-Triazin-2-Yl) Amino]Phenyl 2-Bromo-2-Methylpropionate, 5

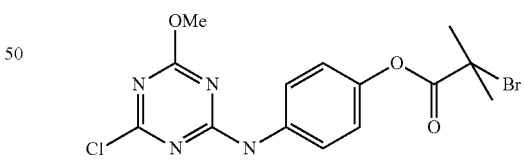

A solution of 2-bromoisobutyryl bromide (1.0 mL, 7.90 mmol) in 20 mL of THF was added dropwise to a solution of 4-[(4-chloro-6-methoxy-1,3,5-triazin-2-yl)amino]phenol (1.9 g, 7.52 mmol) and triethylamine in 100 mL of THF, at −10° C. During the addition (ca. 15 min) precipitation of triethylammonium bromide was observed. The reaction was monitored by TLC (SiO$_2$, petroleum ether/Et$_2$O 1:1, 4-[(4-chloro-6-methoxy-1,3,5-triazin-2-yl)amino]phenol (starting material) R$_f$=0.14; 4-[(4-chloro-6-methoxy-1,3,5-triazin-2-yl)amino]phenyl 2-bromo-2-methylpropionate (final product) R$_f$=0.26). After 1.5 h the white suspension was poured into a conical flask containing 150 mL of Et$_2$O and the ammonium salt removed by filtration on a sintered glass frit. The solvent was then evaporated at reduced pressure to give a white crude residue that was suspended in 10 mL of pentane and filtered. We obtained 2.56 g (6.37 mmol, yield 85%) of 4-[(4-chloro-6-methoxy-1,3,5-triazin-2-yl)amino]phenyl 2-bromo-2-methylpropionate as a white solid. The $^1$H NMR analysis (d$_6$-DMSO) revealed the presence, in solution, of 2 rotational isomers (molar ratio 7:3).

m.p. 107-108° C.; IR $v_{(NH)}$ 3365 cm$^{-1}$. $v_{(C=O)}$ 1747 cm$^{-1}$.

Major isomer: $^1$H NMR (d$_6$-DMSO, 298 K, 400 MHz) δ 2.05 (s, 6H, C(CH$_3$)$_2$Br), 3.96 (s, 3H, OCH$_3$), 7.17 (d, J=8.9 Hz, 2H, CH Ar), 7.77 (d, J=8.9 Hz, 2H, CH Ar), 10.78 (s, 1H, NH); $^{13}$C{$^1$H} NMR (d$_6$-DMSO, 298 K, 100.6 MHz) δ 30.42 (2C, CH$_3$), 55.75 (bs, 1C, OCH$_3$), 57.29 (1C, C(CH$_3$)$_2$Br), 121.96 (2C, CH Ar), 122.12 (2C, CH Ar), 136.29 (1C, C Ar), 146.61 (bs, 1C, C Ar), 165.10 (bs, 1C, C Ar), 169.89 (bs, 1C, C Ar), 170.16 (1C, C=O), 171.33 (bs, 1C, C Ar).

Minor isomer: $^1$H NMR (d$_6$-DMSO, 298 K, 400 MHz) δ 2.05 (s, 6H, C(CH$_3$)$_2$Br), 3.96 (s, 3H, OCH$_3$), 7.17 (d, J=8.9 Hz, 2H, CH Ar), 7.69 (d, J=8.9 Hz, 2H, CH Ar), 10.66 (s, 1H, NH); $^{13}$C($^1$H) NMR (d$_6$-DMSO, 298 K, 100.6 MHz) δ 30.42 (2C, CH$_3$), 55.75 (bs, 1C, OCH$_3$), 57.29 (1C, C(CH$_3$)$_2$Br), 121.96 (2C, CH Ar), 122.73 (2C, CH Ar), 136.29 (1C, C Ar), 146.61 (bs, 1C, C Ar), 165.10 (bs, 1C, C Ar), 169.89 (bs, 1C, C Ar), 170.16 (1C, C=O), 171.33 (bs, 1C, C Ar).

Typical Polymerisation of MMA.

Figure 1:
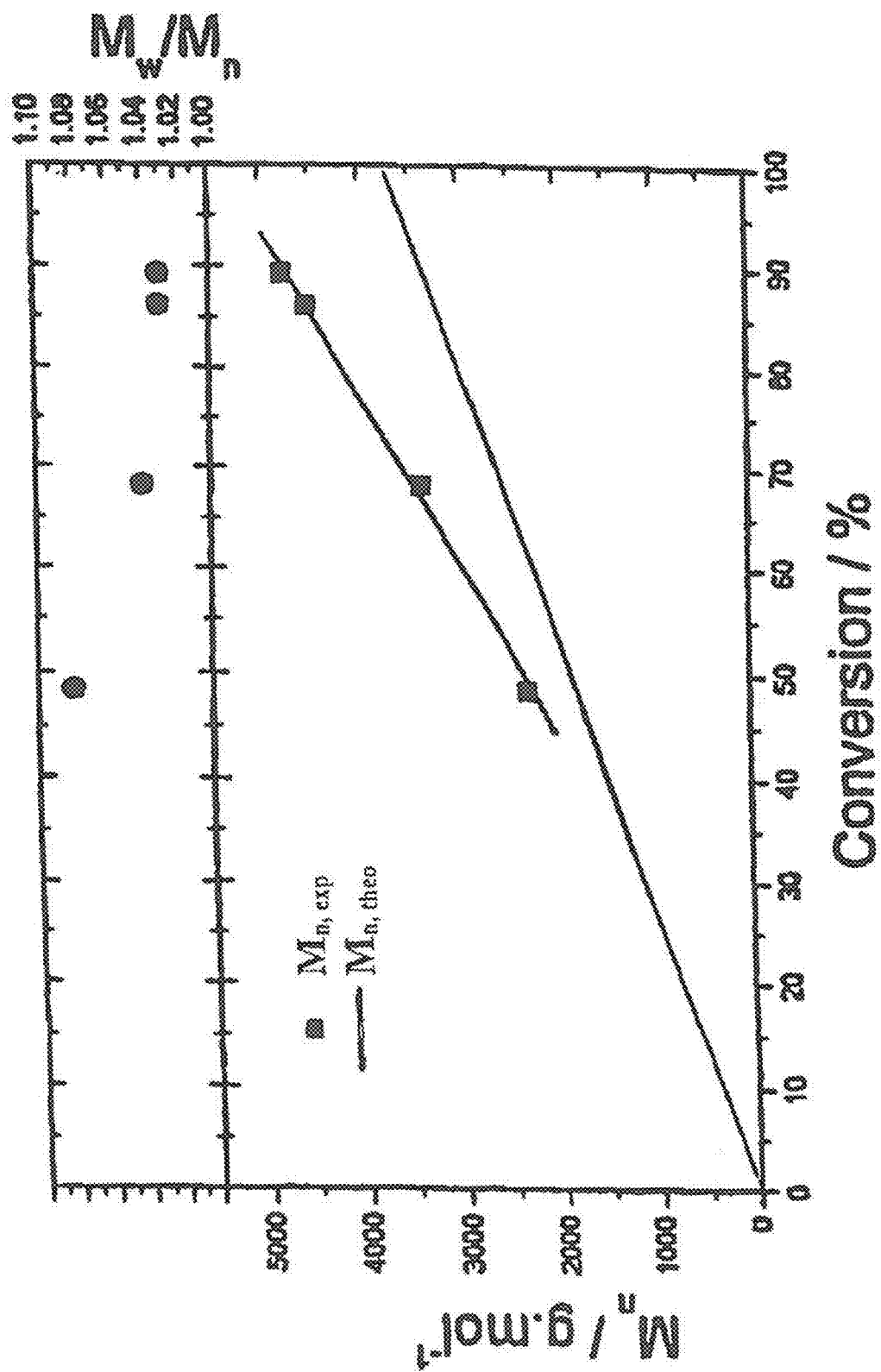
FIG. 1 shows the evolution of molecular weight distribution and polydispersity for the LRP (living radical polymerisation) of methyl methacrylate initiated by a N-hydroxysuccinimide (NHS) initiator.

CuBr (0.134 g, 0.934 mmol) was placed in an oven-dried Schlenk tube. The tube was fitted with a rubber septum, evacuated and flushed with dry N$_2$ three times. Methyl methacrylate (10 mL, 93.4 mmol) and xylene (20 mL) were transferred to the tube via degassed syringe. The mixture was stirred rapidly under nitrogen and N-(n-propyl)-2-pyridyl-methanimine (NMPI) (0.408 g, 1.86 mmol) was added which imparted a deep red/brown colour to the solution. Appropriate initiator (0.934 mmol) was added and the resulting solution was degassed by three freeze-pump-thaw cycles. The resulting mixture was placed in a thermostatically controlled oil bath at 90° C. Samples were taken periodically for conversion and molecular weight analysis. Conversion was measured by gravimetry by drying to constant weight in a vacuum oven at 70° C. The catalyst was removed from the samples by passing through a column of activated basic alumina prior to SEC. (see FIG. 1).

Typical Polymerisation of Styrene.

CuBr (0.055 g, 0.38 mmol) was placed in an oven dried Schlenk tube. The tube was fitted with a rubber septum, evacuated and flushed three times with dry N$_2$. Styrene (10 mL, 96 mmol) was transferred, to the tube via degassed syringe. The mixture was stirred rapidly under nitrogen and 4,4'-di(5-nonyl)-2,2'-bipyridyl (dNbpy) (0.314 g, 0.768 mmol) was added, imparting a deep red/brown colour to the solution. Initiator 7 (0.035 g, 0.048 mmol, 0.192 mmol of initiating sites) was added and the resulting solution was degassed by three freeze-pump-thaw cycles. The resulting mixture was placed in a thermostatically controlled oil bath 110° C. for 4.5 hours. The catalyst was removed from the samples by passing through a column of activated basic alumina prior to SEC.

Kinetic Studies for Initiators 6 and 1%

Samples were removed periodically using degassed syringes and quenched in liquid nitrogen for conversion and molecular weight analysis. Conversion was determined by NMR on a Bruker DPX 300. For Living Radical Polymerisation initiated by 6, samples were passed over a basic alumina column and then filtered in a syringe equipped with a 0.22 μm hydrophobic filter prior to molecular weight studies. In the ease of LRP initiated by 7, molecular weight was determined by diluting the sample with THF and letting it settle overnight to precipitate the catalyst residues. The upper liquid was then filtered with a 0.22 μm hydrophobic filter. This method was chosen for N-hydroxysuccinimide-functionalised polymers as these polymers could not be passed over basic alumina.

Synthesis of a N-Benzylamide Functionalised Poly(MMA)

Figure 2:
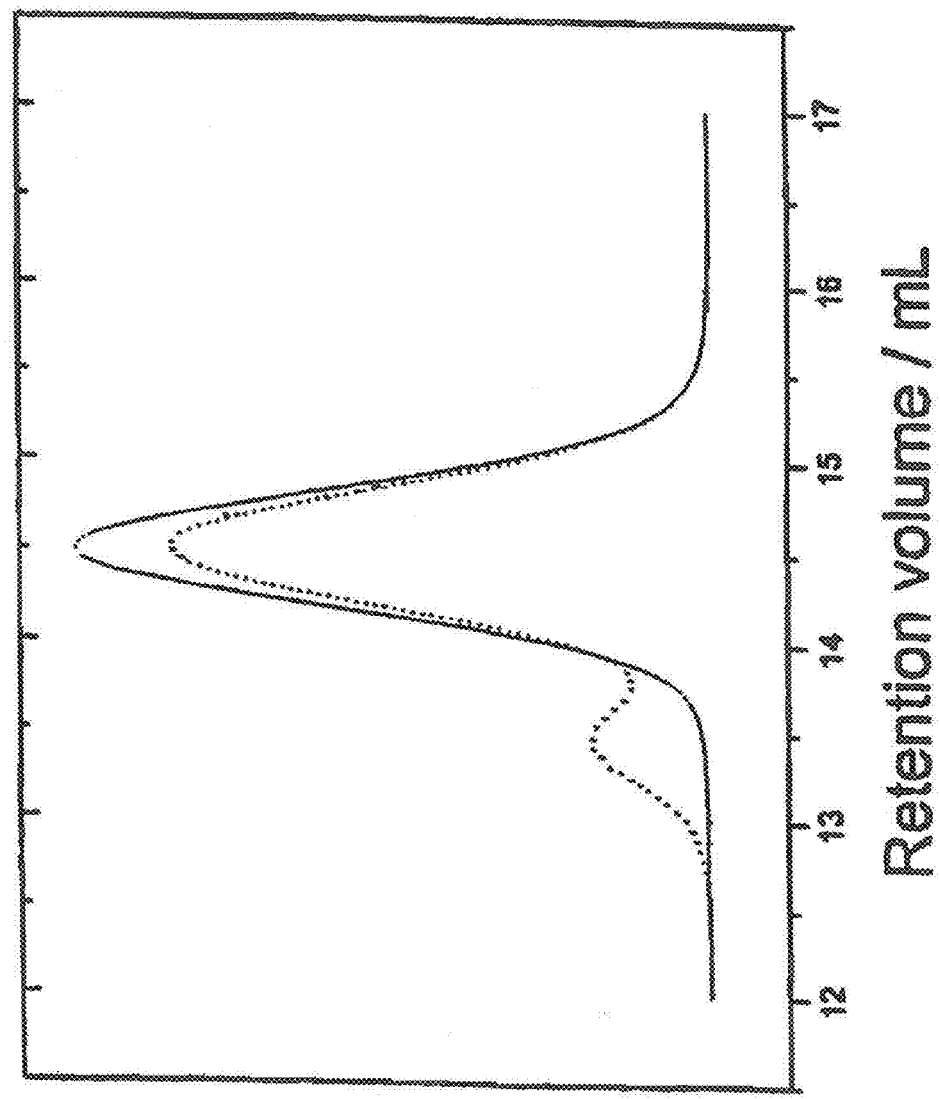
FIG. 2 shows SEC curves for NHS functionalised poly (MMA), solid curve, and the produce (N-benzylamide functionalised poly (MMA), dashed curve).

Benzylamine was added to a solution of N-hydroxysuccinimide terminated poly(methyl methacrylate) in anhydrous THF. N-hydroxysuccinimide-terminated poly(methyl methacrylate) ($M_n$=3200 g mol$^{-1}$, PDI=1.06) (1.00 g, 0.313 mmol) and three equivalents of benzylamine (0,100 mL, 0,938 mmol) were dissolved in 10 mL of dry THF in a dry Schlenk and stirred at 50° C. for 3 days under nitrogen. After reaction, the polymer was precipitated in cold petroleum ether (see FIG. 2).

This shows that N-benzylamide functional groups may be added and can be used to reach with free amide groups of the sort found in proteins.

TABLE 1

Polymerisation of MMA in Xylene Solution (33% v/v) at 90° C.

| Initiator | [MMA]/ Cu(I)Br] [Cu(II)/ Br$_2$]/[NMPI]/ [Initiator] | Time Min | $M_n$ G mol$^{-1}$ | PDi | Conv % | Kp[Pol*]$^a$ * 10$^4$ s$^{-1}$ |
|---|---|---|---|---|---|---|
| 5 | 100/1/0/2/1$^c$ | 480 | 8200 | 1.14 | 66 | |
| 6 | 100/1/0/1/2.1 | 600 | 8900 (9000$^b$) | 1.20 | 75 | 0.047 |
| 7 | 37/1/0/1/2.1 | 138 | 5800 (5800$^b$) | 1.05 | 89 | 0.32 |
| 7 | 60/0.95/0.05/ 1/2.1 | 2880 | 3200 (3100$^b$) | 1.04 | 37 | 0.22 |
| EiBr | 100/1/0/2/1$^d$ | 2880 | 2500 (2400$^b$) | 1.16 | 71 | |

$^a$k$_p$[Pol*] = rate constant of propagation x [active propagating polymer chains] from first order kinetic plot.
$^b$determined by the $^1$H NMR peak intensity ratio on a Bruker DPX 300 MHz
$^c$N-(n-octyl)-2-pyridylmethanimine used as the ligand
$^d$10 mole % HEMA/90 mole % MMA Scheme Coupling of a N-hydroxysuccinimide terminated poly(MMA) with benzylamine.

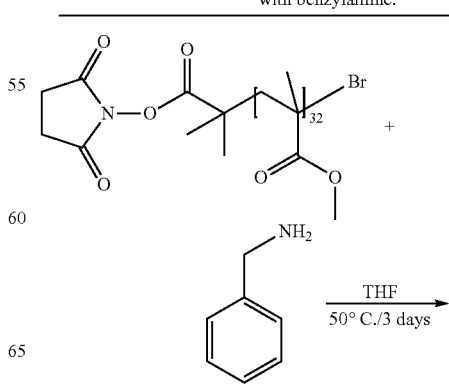

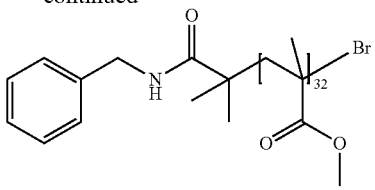

(7)

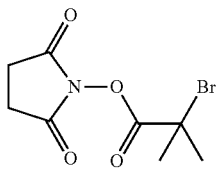

N-Hydroxysuccinimide Initiator (7) (NHS—Br)

Reagents.

Poly(ethylene glycol) methyl ether methacrylate ($M_n$=ca 475, Aldrich, 99%) and anhydrous toluene was degassed by bubbling with dry nitrogen for 30 minutes before use. The ligand N-(n-propyl)-2-pyridylmethanimine was prepared as described previously[1]. Copper(I) bromide (Avocado, 98%) was purified as necessary by a method based on that of Keller and Wyooft[2]. Other reagents were all commercial products and used without further purification.

Typical Procedure.

Polymerizations were carried out at 30° C. mediated by copper(I) bromide/N-(n-propyl)-2-pyridylmethanimine. A typical polymerization recipe is based on 33% v/v monomer in toluene. The ratio of initiator/Cu(I)Br/ligand is 1/1/2.1 on a molar basis. A dry Schlenk tube was charged with Cu(I)Br (0.3099 g, 2.16×10$^{-3}$ mol), NHS—Br (7) (0.5704 g, 2.16×10$^{-3}$ mol) and a magnetic bar prior to being deoxygenated by cycling between nitrogen and vacuum three times. To the flask was then added PEGMA (10 ml, 2.27×10$^{-2}$ mol) and toluene (20 ml). The mixture was immediately subjected to three freeze-pump-thaw degassing cycles. Finally N-(n-propyl)-2-pyridylmethanimine (0.707 ml, 4.54×10$^{-3}$ mol) was added and the flask was placed in an oil bath thermostatted at 30° C.

Kinetic Studies.

Samples were removed periodically using degassed syringes and quenched in liquid nitrogen for conversion and molecular weight analysis. Conversion was determined by NMR on a Brüker DPX 300 MHz. Molecular weight was determined by diluting the sample with toluene and allowing it to settle down overnight to remove the copper complexes. The upper liquid was then filtered with a 0.22 μm hydrophobic filter. This method was chosen because of the difficulty encountered to pass the polymer over a basic alumina column. Number average molecular weights ($M_n$) were determined by Size Exclusion Chromatography (SEC) in a system fitted with a 5 mm guard column, two Polymer Labs mixed E columns, a differential refractive index detector, and an auto sampler. The system was elided with THP at a rate of 1 mL/min. Toluene was used as the flow marker.

Purification.

N-hydroxysuccinimide functionalised poly(PEGMA) were purified by two consecutive purifications from a Toluene solution in diethyl ether.

TABLE 1

Kinetic data for the polymerisation of PEGMA initiated by NHS-Br in toluene solution (33% v/v) at 30° C. ([PEGMA]$_0$/[CuBr]$_0$/[NHSBr]$_0$/[L]$_0$ = 10/1/1/2.1).

| Time (h) | Conversion (%) | $M_{n,exp}$ (g, mol$^{-1}$) | $M_w/M_n$ [a] | $M_{n,theo}$ [b] (g, mol$^{-1}$) |
|---|---|---|---|---|
| 1 | 8.9 | 2350 | 1.10 | 450 |
| 2 | 18.4 | 2860 | 1.26 | 920 |
| 3 | 27.1 | 3100 | 1.20 | 1360 |
| 4 | 34.7 | 3600 | 1.13 | 1730 |
| 17 | 80.8 | 5670 | 1.06 | 4040 |

[a] determined by SEC analysis calibrated with Poly(MMA) standards - THF.
[b] $M_{n,theo}$ = ([M]$_0$/[I]$_0$ × M.W.$_{MMA}$ × Conv.)/100.

TABLE 2

Characterisation of Poly(PEGMA) prepared by LRP

| | Kp[Pol*] [a] (h$^{-1}$) | $M_{n,exp}$ [b] (g, mol$^{-1}$) | $M_w/M_n$ | $M_{n,theo}$ [b] (g, mol$^{-1}$) |
|---|---|---|---|---|
| NHS-Poly(PEGMA) | 0.096 | 6200 | 1.05 | 4040 |

[a] Kp[Pol*] = rate constant of propagation.
[b] determined by SEC calibrated with Poly(MMA) standards - THF (stabilised with topanol).
[b] $M_{n,theo}$ = ([M]$_0$/[I]$_0$ × M.W.$_{MMA}$ × Conv.)/100.

References (a) D. M. Haddletori, M. C. Crossman, B. H. Dana, D, J. Duncalf, A. M. Henning, D. Kukulj and A. J. Shooter, *Macromolecules*, 1999, 32, 2110.

(b) R. N. Keller and W. D. Wycoff, *Inorg. Synth.*, 1947, 2, 1.

Polymerisation of Methoxypolyethyleneglycol Methacrylate (2080) Using the Initiator Thrived from N-Hydroxy Succinimide

[PEG]/[I]/[Cu]/[L]=19.2/1/1/2 in 80% Toluene Solution (AJ U2-27a)@30° C.

N-hydroxy succinimide initiator, (0.05 g, 0,189 mmol), Cu(I)Br (0.027 g, 0.189 mmol, 1 eq) and methoxypolyethyleneglycol methacrylate (PEG) (average molecular weight=2080, 7.55 g, 3.63 mmol), and a magnetic follower were placed in an oven dried Schlenk tube. The Schlenk tube was evacuated and flushed with dry nitrogen three times. Deoxygenated toluene (28 mL) was added to the Schlenk tube. The resulting solution was deoxygenated via three freeze pump thaw cycles and then degassed N-ethyl-2-pyridylimethanimine (0.05 g, 0.38 mmol) was added. The reaction was placed in a thermostatically controlled oil bath at 30° C. (t=0) and samples were removed periodically for conversion and molecular weight analysis. Conversion was followed by $^1$H NMR spectrometry and molecular weight analysis by SEC.

The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). This procedure was repeated three times.

TABLE 1

Data for the polymerization of methoxypolyethyleneglycol methacrylate (2080) with an initiator derived from N-hydroxy succinimide at 30° C. in 80% toluene solution.

| Sample Time/minutes | Conversion[a]/% | Mn[b] | PDi[b] |
|---|---|---|---|
| 89 | 4 | 3380 | 1.04 |
| 291 | 9 | 9820 | 1.09 |
| 901 | 17 | 10030 | 1.07 |
| 1369 | 23 | 11080 | 1.07 |
| 2760 | 26 | 12610 | 1.07 |
| 3965 | 28 | 14830 | 1.04 |

[a]Conversion was determined using 1H NMR.
[b]Molecular mass determined by SEC using PMMA standards.

Bisomer S20W (50% aqueous solution of methoxypolyethyleneglycol methacrylate) was freeze dried prior to use to remove all water.
[PEG]/[I]/[Cu]/[L]=19.2/1/1/2 in 80% Toluene Solution (AJ U2-27b) @50° C.

N-hydroxy succinimide initiator, (0.05 g, 0.189 mmol), Cu(I)Br (0.027 g, 0.189 mmol, 1 eq) and methoxypolyethyleneglyeol methacrylate (PEG) (average molecular weight=2080, 7.55 g, 3.63 mmol), and a magnetic follower were placed in an oven dried Schlenk tube. The Schlenk tube was evacuated and flushed with thy nitrogen three times. Deoxygenated toluene (28 mL) was added to the Schlenk tube. The resulting solution was deoxygenated via three freeze pump thaw cycles and then degassed N-ethyl-2-pyridylmethanimine (0.05 g, 0.38 mmol) was added. The reaction was placed in a thermostatically controlled oil bath at 50° C. (t=0) and samples were removed periodically for conversion and molecular weight analysis. Conversion was followed by ¹H NMR spectrometry and molecular weight analysis by SEC.

The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). This procedure was repeated three times.

TABLE 2

Data for the polymerization of methoxypolyethyleneglycol methacrylate (2080) with an initiator derived from N-hydroxy succinimide at 50° C. in 80% toluene solution.

| Sample Time/minutes | Conversion[a]/% | Mn[b] | PDi[b] |
|---|---|---|---|
| 86 | 7 | 8700 | 1.06 |
| 289 | 12 | 10920 | 1.07 |
| 899 | 24 | 14450 | 1.05 |
| 1367 | 33 | 15810 | 1.04 |
| 2758 | 45 | 20220 | 1.07 |
| 3962 | 53 | 23180 | 1.07 |

[a]Conversion was determined using 1H NMR.
[b]Molecular mass determined by SEC using PMMA standards.

Bisomer S20W (50% aqueous solution of methoxypolyethyleneglycol methacrylate) was freeze dried prior to use to remove all water.
[PEG]/[I]/[Cu]/[L]=19.2/1/1/2 in 80% Toluene Solution (AJ U2-27c)@90° C.

N-hydroxy succinimide initiator, (0.05 g, 0.189 mmol), Cu(I)Br (0.027 g, 0.189 mmol, 1 eq) and methoxypolyethyleneglycol methactylate (PEG) (average molecular weight=2080, 7.55 g, 3.63 mmol), and a magnetic follower were placed in an oven dried Schlenk tube. The Schlenk tube was evacuated and flushed with dry nitrogen three times. Deoxygenated toluene (2 mL) was added to the Schlenk tube. The resulting solution was deoxygenated via three freeze pump thaw cycles and then degassed N-ethyl-2-pyridylmethanimine (0.05 g, 0.38 mmol) was added. The reaction was placed in a thermostatically controlled oil bath at 90° C. (t=0) and samples were removed periodically for conversion and molecular weight analysis. Conversion was followed by ¹H NMR spectrometry and molecular weight analysis by SEC.

The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). This procedure was repeated three times.

TABLE 3

Data for the polymerization of methoxypolyethyleneglycol methacrylate (2080) with an initiator derived from N-hydroxy succinimide at 90° C. in 80% toluene solution.

| Sample Time/minutes | Conversion[a]/% | Mn[b] | PDi[b] |
|---|---|---|---|
| 86 | 18 | 11100 | 1.08 |
| 289 | 26 | 14870 | 1.08 |
| 899 | 31 | 17900 | 1.08 |
| 1367 | 35 | 18110 | 1.09 |
| 2758 | 38 | 18110 | 1.09 |
| 3962 | 39 | 18240 | 1.08 |

[a]Conversion was determined using 1H NMR.
[b]Molecular mass determined by SEC using PMMA standards.

Bisomer S20W (50% aqueous solution of methoxypolyethyleneglyeol methacrylate) was freeze dried prior to use to remove all water.
[PEG]/[I]/[Cu]/[L]=23.9/1/1/2 in 66% Toluene Solution (AJ U2-11) @90° C.

N-hydroxy succinimide initiator, (23 g, 9.47 mmol), Cu(I)Br (1.35 g, 9.47 mmol, 1 eq) and methoxypoiyethyleneglycol methacrylate (PEG) (average molecular weight=628, 142.0 g, 0.226 mol), and a magnetic follower were placed in an oven dried Schlenk tube. The Schlenk tube was evacuated and flushed with dry nitrogen three times. Deoxygenated toluene (261 mL) was added to the Schlenk tube. The resulting solution was deoxygenated via three freeze pump thaw cycles and then degassed N-propyl-2-pyridylmethanimine: (2.80 g, 0.019 mol) was added. The reaction was placed in a thermostatically controlled oil bath at 90° C. (t=0) and samples were removed periodically for conversion and molecular weight analysis. Conversion was followed by ¹H NMR spectrometry and molecular weight analysis by SEC.

The polymer was purified by the dropwise addition of the reaction solution to a vigorously stirred solution of diethyl ether (1000 mL). The resulting oil was washed with diethyl ether (3×1000 mL) and then dried in vacuo.

TABLE 4

Data for the polymerization of methoxypolyethyleneglycol methacrylate (628) with an initiator derived from N-hydroxy succinimide at 90° C. in 66% toluene solution.

| Sample Time/minutes | Conversion[a]/% | Mn[b] | PDi[b] |
|---|---|---|---|
| 48 | 21 | 4449 | 1.11 |
| 132 | 40 | 7198 | 1.08 |
| 185 | 44 | 7779 | 1.07 |

TABLE 4-continued

Data for the polymerization of methoxypolyethyleneglycol methacrylate (628) with an initiator derived from N-hydroxy succinimide at 90° C. in 66% toluene solution.

| Sample Time/minutes | Conversion[a]/% | Mn[b] | PDi[b] |
|---|---|---|---|
| 245 | 46 | 8105 | 1.09 |
| 300 | 48 | 8331 | 1.09 |

[a]Conversion was determined using 1H NMR.
[b]Molecular mass determined by SEC using PMMA standards.

Bisomer MPEG550MA was used as provided.

Polymerisation of Methoxypolyethyleneglycol Methacrylate (1080) Using the N-Hydroxy Succinimide Derived Initiator

[PEG]/[I]/[Cu]/[L]=13.9/1/1/2 in 66% Toluene Solution (AJ U2-13)@90° C.

N-hydroxy succinimide initiator, (0.526 g, 1.99 mmol), Cu(I)Br (0.29 g, 2.02 mmol, 1 eq) and methoxypolyethyleneglycol methacrylate (PEG) (average molecular weight=1080, 29.62 g, 0.027 mol), and a magnetic follower were placed in an oven dried Schlenk tube. The Schlenk tube was evacuated and flushed with dry nitrogen three times. Deoxygenated toluene (60 mL) was added to the Schlenk tube. The resulting solution was deoxygenated via three freeze pump thaw cycles and then degassed N-ethyl-2-pyridylmethanimine (0.51 g, 3.96 mol) was added. The reaction was placed in a thermostatically controlled oil bath at 90° C. (t=0) and samples were removed periodically for conversion and molecular weight analysis. Conversion was followed by $^1$H NMR spectrometry and molecular weight analysis by SEC.

The polymer was purified by the dropwise addition of the reaction solution to a vigorously stirred solution of diethyl ether (1000 mL). The resulting oil was washed with diethyl ether (3×1000 mL) and then dried in vacuo.

TABLE 5

Data for the polymerization of methoxypolyethyleneglycol methacrylate (1080) with an initiator derived from N-hydroxy succinimide at 90° C. in 66% toluene solution.

| Sample Time/minutes | Conversion[a]/% | Mn[b] | PDi[b] |
|---|---|---|---|
| 1250 | 47.3 | 12180 | 1.16 |
| 2460 | 50.4 | 12460 | 1.16 |
| 3890 | 52.8 | 12540 | 1.20 |

[a]Conversion was determined using 1H NMR.
[b]Molecular mass determined by SEC using PMMA standards.

[PEG]/[I]/[Cu]/[L]=9.3/1/1/2 in 66% Toluene Solution (AJ U2-15) @90° C.

N-hydroxy succinimide initiator, (0.5 g, 1.89 mmol), Cu(I)Br (0.27 g, 1.89 mmol, 1 eq) and methoxypolyethyleneglycol methacrylate (PEG) (average molecular weight=1080, 18.90 g, 0.018 mol), and a magnetic follower were placed in an oven dried Schlenk tube. The Schlenk tube was evacuated and flushed with dry nitrogen three times. Deoxygenated toluene (35 mL) was added to the Schlenk tube. The resulting solution was deoxygenated via three freeze pump thaw cycles and then degassed ethyl-2-pyridylmethanimine (0.51 g, 3.79 mmol) was added. The reaction was placed in a thermostatically controlled of bath at 90° C. (t=0) and samples were removed periodically for conversion and molecular weight analysis. Conversion was followed by $^1$H NMR spectrometry and molecular weight analysis by SEC.

TABLE 6

Data for the polymerization of methoxypolyethyleneglycol methacrylate (1080) with an initiator derived from N-hydroxy succinimide at 90° C. in 66% toluene solution.

| Sample Time/minutes | Conversion[a]/% | Mn[b] | PDi[b] |
|---|---|---|---|
| 4160 | 88.7 | 9870 | 1.22 |

[a]Conversion was dertimined using 1H NMR.
[b]Molecular mass determined by SEC using PMMA standards.

Bisomer S10W (50% aqueous solution of methoxypolyethyleneglycol methacrylate) was freeze dried prior to use to remove all water.

Polymerisation of Methxrypolyethyleneglycol Methacrylate (628) Using the Hydroxy Succinimide Derived Initiator

[PEG]/[I]/[Cu]/[L]=6.4/1/1/2 in 66% Toluene Solution (AJ U2-31a) @30° C.

N-hydroxy succinimide initiator, (0.5 g, 1.89 mmol), Cu(I)Br (0.27 g, 1.89 mmol, 1 eq) and methoxypolyethyleneglycol methacrylate (PEG) (average molecular weight=628, 7.57 g, 0.012 mol), and a magnetic follower were placed in art oven dried Schlenk tube. The Schlenk tube was evacuated and flushed with dry nitrogen three times. Deoxygenated toluene (14 mL) was added to the Schlenk tube. The resulting solution was deoxygenated via three freeze pump thaw cycles and then degassed N-ethyl-2-pyridylmethanimine (0.51 g, 3.79 mmol) was added. The reaction was placed in a thermostatically controlled oil bath at 30° C. (r=0) and samples were removed periodically for conversion and molecular weight analysis. Conversion was followed by $^1$H NMR spectrometry and molecular weight analysis by SEC.

TABLE 7

Data for the polymerization of methoxypolyethyleneglycol methacrylate (628) with an initiator derived from N-hydroxy succinimide at 30° C. in 66% toluene solution.

| Sample Time/minutes | Conversion[a]/% | Mn[b] | PDi[b] |
|---|---|---|---|
| 60 | 19 | 2850 | 1.04 |
| 131 | 32 | 3230 | 1.10 |
| 199 | 45 | 3560 | 1.12 |
| 250 | 53 | 3760 | 1.12 |
| 298 | 56 | 3980 | 1.12 |

[a]Conversion was determined using 1H NMR.
[b]Molecular mass determined by SEC using PMMA standards.

Bisomer MPEG550MA was used as provided.
[PEG]/[I]/[Cu]/[L]=6.4/1/1/2 in 66% toluene solution (AJ U2-31b) @50° C.

N-hydroxy succinimide initiator, (0.5 g, 1.89 mmol), Cu(I)Br (0.27 g, 1.89 mmol, 1 eq) and methoxypolyethyleneglycol methacrylate (PEG) (average molecular weight=628, 7.57 g, 0.012 mol), and a magnetic follower were placed in an oven dried Schlenk tube. The Schlenk tube was evacuated and flushed with dry nitrogen three times. Deoxygenated toluene (14 mL) was added to the Schlenk tube. The resulting solution was deoxygenated via three freeze pump thaw cycles and then degassed N-ethyl-2-pyridylmethanimine (0.51 g, 3.79 mmol) was added. The reaction was placed in a thermostatically controlled oil bath at 50° C. (t=0) and samples were removed periodically for conversion and molecular weight analysis. Conversion was followed by $^1$H NMR spectrometry and molecular weight analysis by SEC.

TABLE 8

Data for the polymerization of methoxypolyethyleneglycol methacrylate (628) with an initiator derived from N-hydroxy succinimide at 50° C. in 66% toluene solution.

| Sample Time/minutes | Conversion$^a$/% | Mn$^b$ | PDi$^b$ |
| --- | --- | --- | --- |
| 59 | 39 | 3212 | 1.09 |
| 126 | 56 | 3958 | 1.11 |
| 195 | 69 | 4375 | 1.13 |
| 246 | 75 | 4649 | 1.13 |
| 295 | 82 | 4874 | 1.13 |

$^a$Conversion was determined using 1H NMR.
$^b$Molecular mass determined by SEC using PMMA standards.

Bisomer MPEG550MA was used as provided.

EXPERIMENTAL

General Experimental

For all following polymerisations conversion data was obtained by $^1$H NMR spectroscopy and molecular weight data (Mn and PDi) by SEC using PMMA standards.

Methoxypolyethyleneglycol methacrylates were obtained from Sigma-Aldrich or Laporte Performance Chemicals and used either as received (MPEG(395)MA: Mn 475 g mol$^{-1}$ and BISOMER MPEG(550)MA: Mn 628 g mol$^{-1}$) or freeze dried prior to use to remove all water (BISOMER S10W MPEG (1000)MA: Mn 2080 g mol$^{-1}$ and BISOMER S20W MPEG (2000)MA: Mn=2080 g mol$^{-1}$).

The ligands N-(n-alkyl)-2-pyridylmethanimine were prepared as described previously.[1] Copper(I) bromide was purified as necessary by a method based on that of Keller and Wycoff.[2]

All other reagents were obtained from either Sigma-Aldrich, Romil, Fisher or Acros and used as received.

Functional Initiators

The following table lists the functional initiators used to polymerise the methoxypolyethyleneglycol methacrylates.

TABLE 1

Functional initiators.

| Initiator code | Initiator structure |
| --- | --- |
| 8 | |
| 7 | |
| 5 | |
| 9 | |
| 6 | |
| 10 | |
| 11 | |
| 12 | |
| 13 | |
| 14 | |

TABLE 1-continued

Functional initiators.

| Initiator code | Initiator structure |
|---|---|
| 15 | 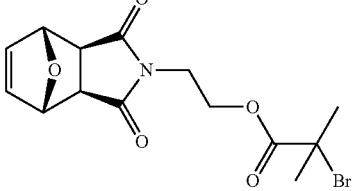 |

Functional Polymers

The following table lists the functional polymers prepared using methoxypolyethyleneglycol methacrylates and the initiators shown in Table 1. These polymers can be used either directly to react with useful biomolecules or converted simply into new macromolecules that will react with useful biomolecules.

TABLE 2

Functional polymers.

| Initiator used | Polymer structure |
|---|---|
| 8 | 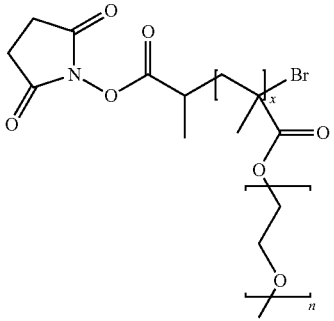 |
| 7 | 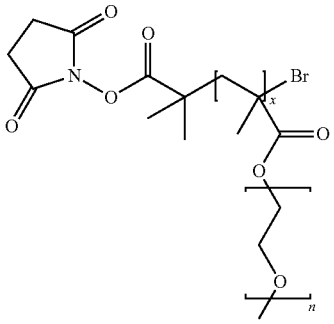 |
| 5 | 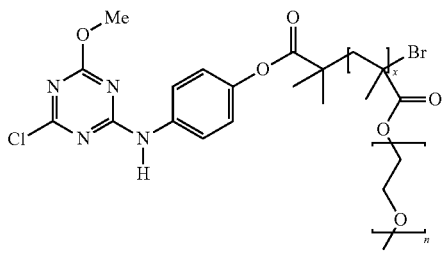 |

TABLE 2-continued

Functional polymers.

| Initiator used | Polymer structure |
|---|---|
| 9 | 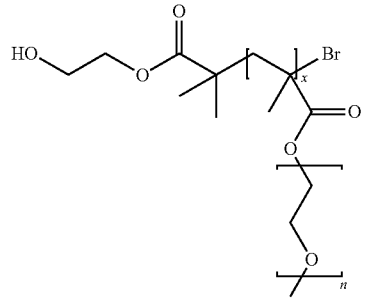 |
| 6 | 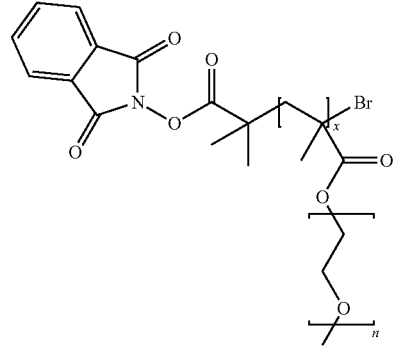 |
| 10 | 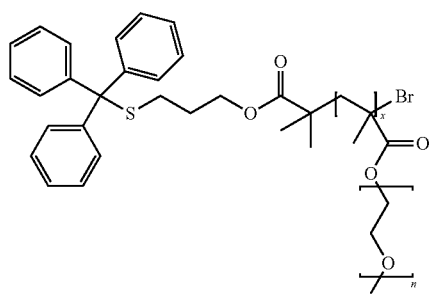 |
| 11 | 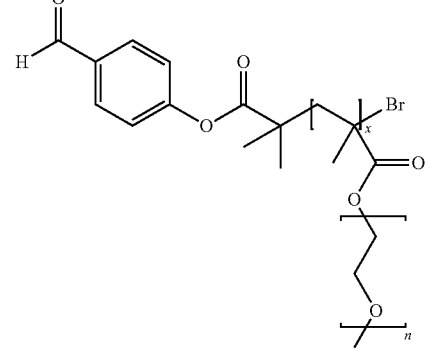 |

TABLE 2-continued

Functional polymers.

| Initiator used | Polymer structure |
|---|---|
| 12 | ![structure] |
| 13 | ![structure] |
| 14 | ![structure] |
| 15 | ![structure] |

PREPARATION OF INITIATORS AND INTERMEDIATES

Preparation of Initiator 8

N-Hydroxysuccinimde-2-Bromopropionate

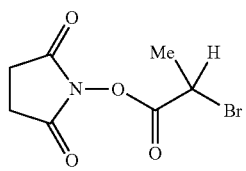

8

N-hydroxysuccinimide (4.51 g, 39.22 mmol) and 2-bromopropionic acid (2.9 mL, 32.68 mmol) were dissolved in anhydrous DCM (1000 ml) in a 2000 mL round-bottomed flask under nitrogen equipped with a magnetic stirrer. The flask was then cooled to 0° C. with an ice bath before the dropwise addition of a solution of N,N'-Dicyclohexylcarbodiimide (6.70 g, 32.68 mmol) in 50 mL of anhydrous DCM. After addition, the mixture was stirred at room temperature overnight. The reaction mixture was then filtered and the solvent evaporated to give a yellow solid that was purified by flash chromatography (CC, $SiO_2$, $Et_2OO$, $R_{f(ester)}$=0.31). Obtained 7.2 g (28.91 mmol, 74%) of product as a white solid. Melting point: 69-70° C. $^1$H NMR ($CDCl_3$) δ (ppm) 1.96 (d, 3H, CH(CH)Br, J=6.78 Hz), 2.86 (s, 4H, $H_{cycl}$), 4.61 (q, 1H, CH(CH$_3$)Br, J=7.03 Hz). $^{13}$C NMR ($CDCl_3$) δ (ppm) 21.67 (1C, CH(CH$_3$)Br) 25.74 (2C, $C_{cycl}$), 34.97 (1C, CH(CH$_3$)Br), 166.17 (1C, C=O), 168.69 (2C, $C_{cycl}$=O). IR (solid, ATR cell) ν (cm$^{-1}$) 1808, 1781 ($C_{cycl}$=O), 1729 (C=O). Mass spectroscopy (+EI, m/z) 248.964. Elem. Anal. Theoretical for $C_7H_8NO_4Br$: C, 33.62; H, 3.22; N, 5.60. Found: C, 33.47; H, 3.16; N, 5.46.

Preparation of Initiator 7

N-Hydroxysuccinimide-2-Bromo-2-Methylpropionate

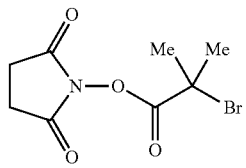

7

N-Hydroxysuccinimide (11.51 g, 0.1 mol) was dissolved in anhydrous dichloromethane (100 ml) with triethylamine (28.1 mL, 0.2 mol) under nitrogen in a 250 ml round-bottomed flask equipped with a magnetic stirrer. The flask was cooled to 0° C. with an ice bath before the dropwise addition of 2-bromo-2-methylpropionyl bromide (13.9 mL, 0.11 mol). Next the mixture was stirred for 45 minutes and allowed to reach room temperature. After this the reaction mixture was poured into an excess of cold water and extracted with diethyl ether (3×50 mL). The organic layer was subsequently washed with a saturated aqueous solution of sodium carbonate (3×50 mL), acidified water (pH=4.5, 3×50 mLl), and again the saturated aqueous solution of sodium carbonate (3×50 mL). The organic layer was dried over anhydrous magnesium sulphate and filtered. Finally the solvent was removed under reduced pressure by using the rotary evaporator in order to isolate the title compound in quantitative yield as a white solid. $^1$H NMR (CDCl$_3$) δ (ppm) 2.08 (s, 6H, C(C$\underline{H}_3$)$_2$Br), 2.87 (s, 4H, H$_{cycl}$). $^{13}$C NMR (CDCl$_3$) δ (ppm) 26.03 (2C, C$_{cycl}$), 31.09 (2C, C($\underline{C}H_3$)$_2$Br), 51.60 (1C, (CH$_3$)$_2$Br), 167.89 (1C, C=O), 169.02 (2C, C$_{cycl}$=O). IR (solid, ATR cell) ν (cm$^{-1}$) 1803, 1772 (C$_{cycl}$=O), 1728 (C=O), 1394, 1359, 1197, 1121, 1071, 996, 924, 856, 811, 731, 648. Mass spectroscopy (+EI, m/z) 266, 265, 156, 151, 149, 123, 121, 116, 115, 91, 87, 70, 69. Elem. Anal. Theoretical for C$_8$H$_{10}$NO$_4$Br: C, 36.39; H, 3.82; N, 5.30; Br, 30.26. Found: C, 36.35; H, 3.82; N, 5.03; Br, 30.17. Melting point 72-74° C.

Preparation of Initiator 5

2,4-Dichloro-6-Methoxy-1,3,5-Triazine$^3$

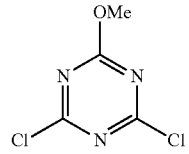

To 200 ml of methanol and 25 ml of water were added 33.6 g. (0.4 mole) of sodium bicarbonate and 36.8 g. (0.2 mole) of cyanuric chloride. This mixture was stirred at 30° C. for 30 minutes until the evolution of carbon dioxide had nearly ceased, and water was then added. The crystalline solid which separated was filtered, washed with water, and dried in a vacuum desiccator. The yield of crude 2,4-dichloro-6-methoxy-triazine was 10.5 g. (58%), m.p. 87-89° C. After recrystallization from heptane the m.p. was 88-90° C. Elem. Anal. Calcd. for C$_4$H$_3$N$_3$OCl$_2$: C, 26.67; H, 1.67; N, 23.35; Cl, 39.44. Found: C, 26.96; H, 1.84; N, 23.25; Cl, 39.19.

4-[(4-Chloro-6-Methoxy-1,3,5-Trazine-2-yl)Amino] Phenol

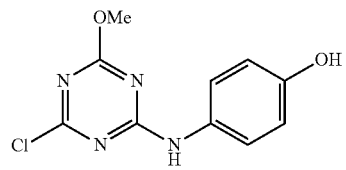 [SMILES: COc1nc(Cl)nc(Nc2ccc(O)cc2)n1]

A solution of 2,4-dichloro-6-methoxy-1,3,5-triazine (9.00 g, 50.0 mmol) in 100 mL of acetone was cooled to 0° C. and, under stirring, solid 4-amino phenol (5.46 g, 50.0 mmol) was added in small portion, over ca 2 min. The white suspension was then let to warm to room temperature and stirred for further 1 h, while being neutralized with a 2 M aqueous solution of Na$_2$CO$_3$ during the reaction. The mixture was then poured into 500 mL of ice/water and the resulting white precipitate was filtered and dried, to give 9.6 g (38.0 mmol, yield 76%) of 4-[(4-chloro-6-methoxy-1,3,5-triazin-2-yl) amino]phenol that can be used without further purifications. An analytical sample can be obtained by flash chromatography (CC, SiO$_2$, petroleum ether/Et$_2$O 1:1, Rf=: 0.14). The NMR analysis (DMSO d6) reveals the presence, in solution, of 2 rotational isomers (molar ratio 7:3). M.p was 172° C. IR ν$_{(NH)}$ 3476 cm$^{-1}$. ν$_{(OH)}$ 3269 cm$^{-1}$. Major isomer: $^1$H NMR (DMSO d6) δ=3.94 (s, 3H, OCH$_3$); 6.79 (d, J=8.8 Hz, 2H, CH Ar), 7.48 (d, J=8.8 Hz, 2H, CH Ar), 9.40 (s, 1H, OH), 10.46 (s, 1H, NH). $^{13}$C NMR (DMSO d6) δ 55.52 (1C, OCH$_3$); 115.46 (2C, CH Ar), 123.91 (2C, CH Ar), 129.49 (1C, C Ar), 154.44 (1C, C Ar), 164.81 (1C, C Ar), 169.57 (1C, C Ar), 171.23 (1C, C Ar). Minor isomer: $^1$H NMR (DMSO d6) δ 3.96 (s, 3H, OCH$_3$); 6.79 (d, J=8.9 Hz, 2H, CH Ar), 7.39 (d, J=8.9 Hz, 2H, CH Ar), 9.42 (bs, 1H, OH), 10.10.32 (s, 1H, NH). $^{13}$C NMR (DMSO d6) δ=55.10 (1C, OCH$_3$); 115.46 (2C, CH Ar), 123.03 (2C, CH Ar), 129.26 (1C, C Ar), 154.76 (1C, C Ar), 165.20 (1C, C Ar), 170.48 (1C, C Ar), 170.64 (1C, C Ar).

4-[(4-Chloro-6-Methoxy-1,3,5-Triazin-2-yl)Amino] Phenyl-2-bromo-2-Methylpropionate

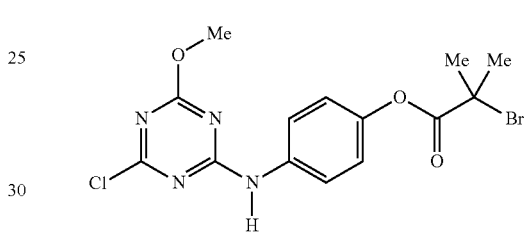

A solution of 2-bromoisobutryl bromide (1.0 mL, 7.90 mmol) in 20 mL of THF was added dropwise to a solution of 4-[(4-chloro-6-methoxy-1,3,5-triazin-2-yl)amino]phenol BIW009 (1.9 g, 7.52 mmol) and triethylamine (1.1 mL, 8.0 mmol) in 100 mL of THF, at −10° C. During the dropping (ca. 15 min) the precipitation of triethylammonium bromide was observed. The reaction was monitored by TLC (SiO$_2$, petroleum ether/Et$_2$O 1:1, BIW009 (starting material) Rf=0.14; BIW010 (final product) Rf=0.26). After 1.5 h the white suspension was poured into a conical flask containing 150 mL of Et$_2$O and the ammonium salt removed by filtration on a sintered glass frit. The solvent was then evaporated at reduced pressure to give a white crude residue that was suspended in 10 ml of pentane and filtered. Obtained 2.56 g (6.37 mmol, yield 85%) of BIW010 as white solid. The NMR analysis (DMSO d6) revealed the presence, in solution, of 2 rotational isomers (molar ratio 7:3). M.p. 107-108° C. IR ν$_{(NH)}$ 3365 cm$^{-1}$. ν$_{(C|O)}$ 1747 cm$^{-1}$. Major isomer: $^1$H NMR (DMSO d6) δ 2.05 (s, 6H, C(C$\underline{H}_3$)$_2$Br), 3.96 (s, 3H, OCH$_3$), 7.17 (d, J=8.9 Hz, 2H, CH Ar), 7.77 (d, J=8.9 Hz, 2H, CH Ar), 10.78 (s, 1H, NH). $^{13}$C{$^1$H} NMR (DMSO d6) δ=30.42 (2C, CH$_3$), 55.75 (bs, 1C, OCH$_3$), 57.29 (1C, $\underline{C}$(CH$_3$)$_2$Br), 121.96 (2C, CH Ar), 122.12 (2C, CH Ar), 136.29 (1C, C Ar), 146.61 (bs, 1C, C Ar), 165.10 (bs, 1C, C Ar), 169.89 (bs, 1C, C Ar), 170.16 (1C, O$\underline{C}$(O)C(CH$_3$)$_2$Br), 171.33 (bs, 1C, C Ar). Minor isomer. $^1$H NMR (DMSO d6) δ=2.05 (s, 6H, C(C$\underline{H}_3$)$_2$Br), 3.96 (s, 3H, OCH$_3$), 7.17 (d, J=8.9 Hz, 2H, CH Ar), 7.69 (d, J=8.9 Hz, 2H, CH Ar), 10.66 (s, 1H, NH).

$^{13}$C NMR (DMSO d6) δ=30.42 (2C, CH$_3$), 55.75 (bs, 1C, OCH$_3$), 57.29 (1C, $\underline{C}$(CH$_3$)$_2$Br), 121.96 (2C, CH Ar), 122.73 (2C, CH Ar), 136.29 (1C, C Ar), 146.61 (bs, 1C, C Ar), 165.10

(bs, 1C, C Ar), 169.89 (bs, 1C, C Ar), 170.16 (1C, OC(O)C(CH$_3$)$_2$B3r), 171.33 (bs, 1C, C Ar).

Preparation of Initiator 9

2-Hydroxyethyl-2-Bromo-2-Methylpropionate

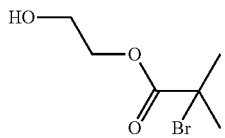

9

Ethylene glycol (279 g, 4500 mmol) and Et$_3$N (3.34 g, 33.0 mmol) were poured in a 2-necked round bottom flask. To this was added dropwise and a solution of 2-bromoisobutryl bromide (6.90 g, 30.0 mmol) in anhydrous THF (50 mL) at room temperature over ca. 1 h. The colourless solution was stirred overnight, then diluted in 500 mL of water and extracted with 3×200 mL of a mixture of Et$_2$O/CH$_2$Cl$_2$ (4:1). The organic layers, reunited, were washed with 2×200 mL of water and dried over MgSO$_4$. Evaporation of the solvent at reduced pressure (rotavapor, without heating) gave a pale yellow liquid. The latter was dissolved in ca. 30 mL of CH$_2$Cl$_2$ then 10 g of SiO$_2$ were added and the solvent evaporated again until a white powder was obtained. This was poured in a column packed with SiO$_2$, (ca 15 cm depth) previously eluted with petroleum ether/Et$_2$O 5:1 and purified by column chromatography (elute with petroleum ether/Et$_2$O 5:1) to eliminate the impurities. The desired product, using this solvent mixture, has an Rf~0 (stays on the bottom of the TLC plate). When the impurities have been eliminated, the column was eluted with 100% Et$_2$O, to give a colourless liquid. Yield 82%. IR $\nu_{(N-H)}$ 3388 cm$^{-}$ (broad); $\nu_{(C=O)}$ 1731 cm$^{-1}$. $^1$H NMR (CDCl$_3$) δ=1.97 (s, 6H, CH$_3$); 3.89 (t, J=4.6 Hz; 2H, OCH$_2$CH$_2$OH); 4.33 (t, J=4.6 Hz; 2H, OCH$_2$CH$_2$OH). $^{13}$C NMR (CDCl$_3$) δ=30.45 (2C, CH$_3$), 55.55 (1C, C(CH$_3$)$_2$Br); 60.66 (1C, OCH$_2$CH$_2$OH); 65.90 (1C, OCH$_2$CH$_2$OH); 171.69 (1C, C=O).

Preparation of Initiator 6

2-Phthalmidoethyl-2-Bromo-2-Methylpropionate

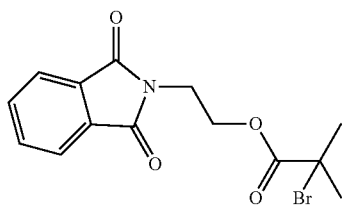

6

N-(2-hydroxyethyl)phthalimide (19.12 g, 0.1 mol) was dissolved in anhydrous THF (250 mL) with triethylamine (28.1 mL, 0.2 mol) under nitrogen in a 500 mL round bottom flask equipped with a magnetic stirrer and dropping funnel. The flask was cooled to 0° C. with an ice/salt bath before the dropwise addition of 2-bromo-2-methylpropionyl bromide (13.9 mL, 0.11 mol). The mixture was stirred for 45 minutes and allowed to reach room temperature before the mixture was poured into an excess of cold water and the product extracted with diethyl ether (3×100 mL). The organic layer was subsequently washed with a saturated aqueous solution of sodium carbonate (3×100 mL), acidified water (pH 4.6, 3×100 mL) and again with saturated aqueous solution of sodium carbonate (3×100 mL). The organic layer was dried over anhydrous magnesium sulphate and filtered. The product was isolated via reduction under reduced pressure to obtain a white solid (25.79 g, 75.8% yield). $^1$H NMR (CDCl$_3$) δ (ppm) 1.81 (s, 6H, C(Ct)$_2$Br), 3.95 (t, 2H, J=5.3 Hz, CH$_2$—N), 4.35 (t, 2H, J=5.4 Hz, CH$_2$—O), 7.67 (m, 2H, H$_{aro}$), 7.78 (m, 2H, H$_{aro}$). $^{13}$C NMR (CDCl$_3$) δ (ppm) 31.00 (2C, C(CH$_3$)$_2$Br), 37.12 (1C, CH$_2$—N), 55.92 (1C, C(CH$_3$)$_2$Br), 63.42 (1C, CH$_2$—O), 123.78 (2C, C$_{aro}$), 132.35 (1C, C$^{IV}_{aro}$), 133.54 (2C, C$_{aro}$), 168.40 (2C, C$_{cycl}$=O), 171.87 (1C, C=O). IR (solid, ATR cell) ν (cm$^{-1}$) 2975, 1774 (C$_{cycl}$=O), 1705 (C=O), 1417, 1392, 1321, 1276, 1158, 1105, 1063, 985, 763, 716, 632. Melting point 63-65° C.

Preparation of Initiator 10

Tritylthioether Propanol

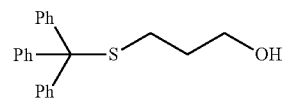

Sodium hydride (10.95 g, 0.273 mol, 60% in oil) was suspended in THF (750 mL) at 0° C. Triphenylmethanethiol (75.5 g, 0.273 mol) in THF (600 ml) was added to the suspension and stirred at 0° C. for 10 minutes. 3-Bromo-1-propanol (24.75 mL, 0.273 mol) in THF (300 mLl) was added and the mixture stirred at 0° C. for 20 minutes. After this time TLC showed mostly one major product (Rf approx 0.3 ethyl acetate/hexane 1:9). Water was added and the product extracted into ethyl acetate (2×1000 mL) (an aqueous NaCl solution was used to break up the emulsion), dried with sodium sulfate, filtered and concentrated. The product was purified by column chromatography using ethyl acetate/hexane 1:9 to 1:4 as the eluent (SiO$_2$) to give a white solid, which was triturated with hexane and filtered to give 65.2 g of product. $^1$H NMR (CDCl$_3$) δ ppm 7.6-7.1 (m, 15H H$_{aro}$), 3.58 (t, 2H, CH$_2$OH), 2.29 (t, 2H, SCH$_2$), 1.65 (q, 2H, CH$_2$CH$_2$CH$_2$), 1.45 (OH).

3-Tritylthioetherpropyl-2-Bromo-2-Methylpropionate

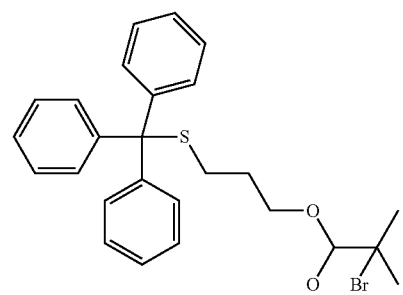

10

Tritylthioether propanol (50 g, 0.150 mol), triethylamine (31.3 mL, 0.225 mol) and anhydrous tetrahydrofuran (125 mL) were placed in a three-necked round bottom flask containing a magnetic follower and fitted with a pressure equalizing dropping funnel. The flask was cooled with the use of an ice bath and 2-bromoisobutyrl bromide (27.8 mL, 0.225 mol) was added to the dropping funnel. Whilst stirring the 2-bromoisobutyrl bromide was added drop-wise to the cooled solution and the solution left stirring over night. The mixture is then filtered to remove the triethylamine hydrochloride salt before the addition of dichloromethane (500 mL) and subsequently washed with dilute hydrochloric acid (2×300 mL), dilute sodium hydroxide (2×300 mL) and finally distilled water (3×300 mL). The Organic layer was separated and the product isolated by flash evaporation of solvent, the product was then triturated with hexane, filtered and the product collected in quantitative yield. $^1$H NMR (CDCl$_3$) δ ppm 7.4-7.1 (m, 15H, H$_{aro}$), 4.02 (t, 2H, CH$_2$CO$_2$), 2.15 (t, 2H, SCH$_2$), 1.78 (s, 3H, C(CH$_3$)$_2$Br), 1.63 (q, 2H, CH$_2$CH$_2$CH$_2$).

Preparation of Initiator 11

4-(2-Bromo-2-Methylpropionate) Benzaldehyde

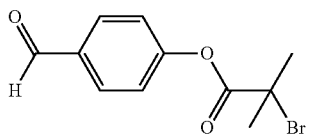

4-Hydroxybenzaldehyde 12.21 g (0.1 moles), triethylamine, 15.3 mL (0.11 moles) and anhydrous THF 400 mL were placed in a 3 neck round bottomed flask, Bromoisobutyryl bromide 13.6 mL (0.11 moles) was added slowly with stirring. A white precipitate of triethylammonium bromide was formed. The mixture was left to react for 6 hours with stirring. On completion of the reaction triethylammonium bromide was removed by filtration and the THF was removed by rotary evaporation. The resulting orange liquid was dissolved in dichloromethane and subsequently washed with 2×200 mL portions of saturated Na$_2$CO$_3$ (aq), dil. HCl (aq) and distilled water. The dichloromethane was dried using MgSO$_4$ and the solvent removed by rotary evaporation to give a yellow oily liquid which crystallised upon standing. This was recrystalised from diethyl ether×2. Yield=18.95 g (69.9%). $^1$H NMR (CDCl$_3$) δ (ppm) 10.00 (s, 1H, CHO), 7.94 (d, J=4.6 Hz, 2H, H$_{aro}$), 7.31 (d, J=4.8 Hz 2H, H$_{aro}$), 2.06 (s, 6H, C(CH$_2$Br). $^{13}$C NMR (CDCl$_3$) δ (ppm) 190.59, 169.33, 155.08, 134.07, 131.02, 121.71, 54.94, 30.25. IR (Solid, ATR Cell) 2984, 2820, 2730 (O=C—H), 1746 (C=O), 1693 (H—C=O), 1590, 1500, 1374, 1262, 1207, 1153, 1132, 1099, 1009, 932, 881, 808, 658: +EI MS (m/z) 273, 271 (mass peaks), 210, 193, 163, 151, 149, 140, 123, 121, 102. Elem. Anal. Theoretical for H11O3Br: C=48.73, H=4.09. Found: C=48.63, H=4.03.

Preparation of Initiator 12

2-(2,2-Dimethoxy-Ethoxy)-Ethanol

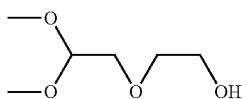

Potassium hydroxide (30 g, 0.51 mol) was suspended in ethylene glycol (100 ml) and the mixture was heated to 115° C. with stirring. After the KOH dissolved completely, 2-chloro-1,1-dimethoxy-ethane (30.0 mL, 0.263 mol) was added dropwise (ca. 30 minutes) and the solution was stirred at 115° C. for 72 h. The resulting suspension was cooled to room temperature and 150 mL water was added. The solution was extracted with dichloromethane (3×100 mL) and the organic layers combined was washed with brine (2×100 mL) and dried with MgSO$_4$. After filtration the solvent was removed under reduced pressure to give the product as a yellow oil (Yield, 17.7 g, 44.9%). $^1$H NMR (400.03 MHz, CDCl$_3$, 298 K) δ=2.20 (s, 1H, OH), 3.40 (s, 6H, OCH$_3$), 3.55 (d, J=5.3 Hz, 2H, CHCH$_2$), 3.63-3.61 (m, J=4.0 Hz, OCH$_2$), 3.74-3.72 (m, J=4.0 Hz, 2H, CH$_2$OH), 4.52 (t, 1H, CH(OCH$_3$)$_2$. $^{13}$C{H} NMR (100.59 MHz, CDCl$_3$, 298 K) δ=54.12 (2C, CH$_3$), 61.82 (1C, CH$_2$OH), 70.78 (1C, CH CH$_2$O), 73.00 (1C, OCH$_2$CH$_2$), 102.73 (1C, CH). Anal. Calcd. for C$_6$H$_{14}$O$_4$: C, 47.99; H, 9.40. Found C, 45.02; H, 8.74

2-Bromo-2-Methyl-Propionic Acid 2-(2,2-Dimethoxy-Ethoxy)-Ethyl Ester

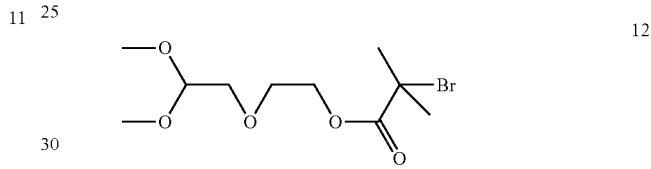

A solution of 2-(2,2-dimethoxy-ethoxy)-ethanol (11 g, 0.073 mol) and triethylamine (12 mL, 0.088 mol) in dichloromethane (150 mL) was cooled to 0° C. and a solution of 2-bromo-2-methyl propionyl bromide (8.5 mL, 0.069 mol) in 50 mL of dichloromethane was added dropwise in ca. 30 min. After stirring overnight at room temperature the resulting suspension was filtered and the yellow solution was washed with saturated NaHCO$_3$ aqueous solution (2×100 mL) and dried with MgSO$_4$. After filtration the solvent was removed under reduced pressure and the yellow oily residue was purified by distillation (b.p. 70° C./0.02 mbar) to give 14.0 g (0.061 mol, yield: 89%) of product as a colourless oil. $^1$H NMR (400.03 MHz, CDCl$_3$, 298 K) δ=1.94 (s, 6H, (CH$_3$)$_2$CBr), 3.39 (s, 6H, OCH$_3$), 3.56 (d, J=5.3 Hz, 2H, CHC H$_2$), 3.76 (t, J=4.8 Hz, CH$_2$OCH$_2$), 4.33 (t, J=4.8 Hz, 2H, C H$_2$OCO), 4.50 (t, 1H, CH(OCH$_3$)$_2$. $^{13}$C{$^1$H} NMR (100.59 MHz, CDCl$_3$, 298 K) δ=30.90 (2C, C(CH$_3$)$_2$), 54.13 (2C, CH$_3$O), 55.79 (1C, BrC(CH$_3$)$_2$), 65.24 (1C, CH$_2$OC(=O)), 69.21 (1C, CHCH$_2$O), 71.18 (1C, OCH$_2$CH$_2$), 102.83 (1C, CH).

Preparation of Initiator 13

3-(2,5-Dioxo-2,5-Dihydro-Pyrrol-1-yl)-Propionic Acid

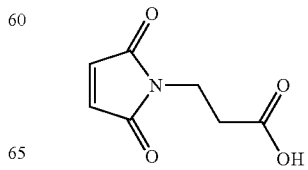

A solution of maleic anhydride (5.00 g, 0.0561 mol) in acetic acid (70 ml) was added dropwise to a solution of β-alanine (5.50 g, 0.0561 mol) in acetic acid (25 ml) and the mixture was stirred at room temperature for three hours. 50 mL of acetic acid was added to the white suspension and the mixture heated up to 115° C. After 1 h a limpid colourless solution was observed. The mixture was then stirred at this temperature overnight and the colour turned to orange. The solvent was then removed under reduced pressure and 30 mL of toluene was then added to the resulting orange oil. This was then evaporated under reduced pressure and this operation was repeated 3 times. The orange residue was then purified by flash chromatography (CC, SiO$_2$, CH$_2$Cl$_2$/ethyl acetate 9:1) to give the product as a white solid (3.86 g, 0.0228 mol, 41%). m.p. 105-107° C. IR (neat): 3092, 2883, 2537, 1695, 1445, 1411, 1373, 1337, 1305, 1230, 1151, 1081, 1043, 924, 830, 773, 694, 618 cm$^{-1}$ $^1$H NMR (400.03 MHz, CDCl$_3$, 298 K) δ=2.69 (t, J=7.3 Hz, 2H, CH$_2$), 3.82 (t, J=7.3 Hz, 2H, CH$_2$), 6.71 (s, 2H, CH$_{vinyl}$), 10.07 (bs, 1H, COOH). $^{13}$C{$^1$H} NMR (100.59 MHz, CDCl$_3$, 298 K) δ=32.62 (1C, CH$_2$), 33.36 (1C, CH$_2$), 134.38 (2C, CH$_{vinyl}$), 170.48 (1C, C), 176.64 (2C, C). Anal. Calcd. for C$_7$H$_7$NO$_4$: C, 49.71; H, 4.17; N, 8.28. Found C, 49.35; H, 4.19; N, 7.95.

3-(2,5-Dioxo-2,5-Dihydro-Pyrrol-1-yl)-Proponyl Chloride (3-malemidopropionyl Chloride)

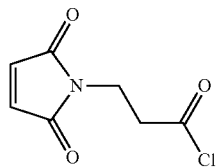 [SMILES: O=C(Cl)CCN1C(=O)C=CC1=O]

3-(2,5-Dioxo-2,5-dihydro-pyrrol-1-yl)-propionic acid (2.20 g, 0.0130 mol) was dissolved in CH$_2$Cl$_2$ (100 mL). Oxalyl chloride (1.1 mL, 0.0130 mol) was then added, at room temperature. 50 μL of DMF were added dropwise and an intense evolution of gas was observed. The solution was colourless before the addition of DMF and remained colourless for 1 h, then slowly turned to very pale yellow (but still very limpid). After 3 h the solvent was removed under reduced pressure to give an off-white solid that became pale brown after standing under vacuum at room temperature for 1 h. The acid chloride product so obtained was used directly without further purifications. IR (neat): 3095, 1803 1698, 1446, 1410, 1387, 1360, 1307, 1230, 1148, 1131, 1083, 1011, 948, 922, 833, 719, 689, cm$^{-1}$. $^1$H NMR (400.03 MHz, CDCl$_3$, 298 K) δ=3.25 (t, J=6.9 Hz, 2H, CH$_2$), 3.86 (t, J=6.9 Hz, 2H, CH$_2$), 6.73 (s, 2H, CH$_{vinyl}$). $^{13}$C{$^1$H} NMR (100.59 MHz, CDCl$_3$, 298 K) δ=33.21 (1C, CH$_2$), 44.97 (1C, CH$_2$), 134.47 (2C, CH$_{vinyl}$), 170.08 (2C, C), 171.50 (1C, C).

2-Bromo-2-Methyl-Propionic Acid 2-[3-(2,5-dioxo-2,S-Dihydro-Pyrrol-1-yl)-Propionyloxy]-Ethyl Ester

13

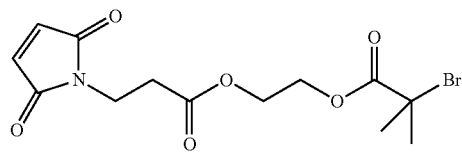

2-Hydroxyethyl-2-bromo-2-methylpropionate (initiator 9) (0.187 g, 0.887 mmol) and 3-(2,5-Dioxo-2,5-dihydro-pyrrol-1-yl)-propionic acid (0.300 g, 1.77 mmol) were dissolved in dichloromethane (10 ml) under nitrogen in a 25 ml round-bottomed flask. Then N,N'-Dicyclohexylcarbodiimide (DCC) (0.366 g, 1.77 mmol) was added to the solution. After one day at room temperature, very low conversion was observed and 0.5 ml (9.50×10$^{-3}$ mmol) of a solution of 4-dimethylaminopyridine (DMAP) in dichloromethane (Conc.$_{DMAP}$=19 mmol/l) was added. Total conversion was then achieved in 12 hours and the solvent was removed under reduced pressure. The solid residue was extracted with 3×50 ml of petroleum ether and the petroleum ether was removed by evaporation under vacuum in order to isolate a colourless oil (0.270 g, 0.745 mmol, 84%). The pale pink residue was extracted with 3×50 ml of diethylether, but TLC(CH$_2$Cl$_2$/AcOEt 9:1) revealed that only traces of the ester were present. An analytical pure sample was obtained by flash chromatography (cc, SiOz, Pet. Ether/Et$_2$O 3:1).

$^1$H NMR (CDCl$_3$) δ (ppm) 1.88 (s, 6H, C(Ch)$_2$Br), 2.62 (t, 2H, CH$_2$—COO(CH$_2$)$_2$—O, J$_{ab}$=7.02 Hz), 3.78 (t, 2H, (CO)$_2$N—CH$_2$, J$_{ab}$=7.07 Hz), 4.27-4.35 (m, 4H, O—(CH$_2$)$_2$—O), 6.68 (s, 2H, OC—CH═CH—CO). $^{13}$C NMR (CDCl$_3$) δ (ppm) 30.61 (2C, C(CH$_3$)$_2$Br), 32.75 (1C, CH$_2$—COO(CH$_2$)—O), 33.46 (1C, (CO)$_2$N-CH$_2$), 55.45 (1C, C(CH$_3$)$_2$Br), 62.04 (1C, CH$_2$—COO—CH$_2$), 63.35 (1C, CH$_2$—OOC—C(CH$_3$)$_2$Br), 134.25 (2C, OC—CH═CH—CO), 170.29 (1C, C═O ester), 170.40 (1C, C═O ester), 171.39 (2C, O═C—N(CH$_2$)—C═O). IR (solid, ATR cell) ν (cm$^{-1}$) 1769 ($\overline{\nu}_{(C═O, imide)}$), 1736 ($\overline{\nu}_{(C═O, acid)}$), 1707 ($\overline{\nu}_{(C═O, imide)}$).

Preparation of Initiator 14

2-Bromo-2-Methyl-Propionic Acid 3-Tert-Butoxycarbonylamino-Propyl Ester

14

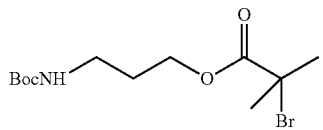

A solution of 3-amino propanol (3.00 mL, 0.0392 mol) in 100 mL of THF was cooled to 0° C. and Boc$_2$O (8.56 g, 0.0322 mol) in THF (50 mL) was added dropwise (ca. 20 min.). The solution was then warmed up to room temperature and stirred for 3 h. TLC analysis (SiO$_2$, 100% Et$_2$O) revealed the complete disappearance of the amino alcohol starting material (R$_f$=0) and the presence of the expected N-Boc-protected amino alcohol intermediate (R$_f$=0.25). The mixture was then cooled to 0° C. and Et$_3$N (6.0 mL, 0.0431 mol) was added via syringe. A solution of 2-bromo isobutyryl bromide (4.85 mL, 0.0392 mol) in THF (50 mL) was added dropwise in ca. 30 min. and the resulting white suspension stirred at 0° C. for 1 h and at room temperature for further 2 h. The mixture was then diluted with Et$_2$O (200 mL) and the ammonium salt was filtered off and washed with 3×50 mL of Et$_2$O. The colourless solution was washed with 3×100 mL of water and dried over MgSO$_4$. Removal of the solvent under reduced pressure gave the product a colourless oil that was purified by flash chromatography (CC, SiO$_2$, Petroleum ether/Et$_2$O 8:1).

Obtained 10.42 g (0.0321 mol, 82%) of (1) as colourless oil. IR (neat): 3295, 2976, 1734, 1713, 1695, 1517, 1463, 1391, 1366 1273, 1163, 1109, 1013, 633 cm$^{-1}$. $^1$H NMR (400.03 MHz, CDC$_3$, 298 K) δ=1.43 (s, 9H, CH$_3$), 1.88 (quint., J=6.3 Hz, 2H, CH$_2$), 1.93 (s, 6H, CH$_3$), 3.23 (q, J=6.0 Hz, 2H, CH$_2$), 4.24 (q, J=6.0 Hz, 2H, CH$_2$), 4.77 (bs, 1H, NH). $^{13}$C {$^1$H} NMR (100.59 MHz, CDCl$_3$, 298 K) δ=28.54 (3C, CH$_3$), 28.99 (1C, CH$_2$), 30.88 (2C, CH)), 37.57 (1C, CH$_2$), 55.95 (1C, C), 63.86 (1C, CH$_2$), 156.03 (1C, C), 171.89 (1C, C). Anal. Calcd. for C$_{12}$H$_{22}$BrNO$_4$: C, 44.46; H, 6.84; N, 4.32; Br, 24.65. Found C, 44.48; H, 6.91; N, 4.33. Br, 24.91.

Preparation of Initiator 15

4,10-Dioxa-Tricyclo[5.2.1.0$^{2,6}$]Dec-8-Ene-3,5-Dione

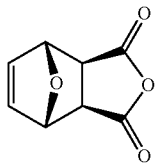 [SMILES: O=C1OC(=O)[C@H]2[C@@H]1[C@@H]1C=C[C@H]2O1]

Maleic anhydride (30.00 g, 0.306 mol) was suspended in 150 mL of toluene and the mixture warmed to 80° C. Furan (33.4 mL, 0.459 mol) was added via syringe and the turbid solution stirred for 6 h. The mixture was then cooled to room temperature and the stirring was stopped. After 1 h the resulting white crystals were filtered off and the solid washed with 2×30 mL of petroleum ether. Obtained 44.40 g (0.267 mol, 87% yield) of the desired product as small white needless. m.p. 124-127° C. (dec.) IR (neat): 1857, 1780, 1309, 1282, 1211, 1145, 1083, 1019, 947, 920, 902, 877, 847, 800, 732, 690, 674, 633, 575 cm$^{-1}$. $^1$H NMR (400.03 MHz, CDCl$_3$, 298 K) δ=3.17 (s, 2H, CH), 5.45 (t, J=1.0 Hz, 2H, CHO); 6.57 (t, J=1.0 Hz, 2H, CH$_{vinyl}$). $^{13}$C{$^1$H} NMR (100.59 MHz, CDCl$_3$, 298 K) δ=48.85 (2C, CH), 82.35 (2H, CHO), 137.12 (2C, CH$_{vinyl}$), 170.04 (2C, CO). Anal. Calcd. for C$_8$H$_6$O$_4$: C, 57.84; H, 3.64. Found C, 57.74; H, 3.68.

4-(2-Hydroxy-Ethyl)-10-Oxa-4-Aza-Tricyclo [5.2.1.0$^{2,6}$]Dec-8-Ene-3,5-Dione

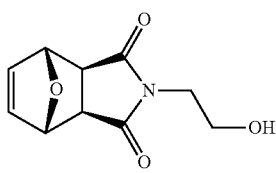 [SMILES: O=C1[C@@H]2[C@H](C(=O)N1CCO)[C@H]1C=C[C@@H]2O1]

The anhydride, 4,10-dioxa-tricyclo[5.2.1.0$^{2,6}$]dec-8-ene-3,5-dione, (2.00 g, 12.0×10$^{-3}$ mol) was suspended in 50 mL of MeOH and the mixture cooled to 0° C. A solution of ethanolamine (0.72 mL, 12.0×10$^{-3}$ mol) in 20 mL of MeOH was added dropwise (10 min) and the resulting solution was stirred for 5 min at 0° C., then 30 min at room temperature and finally refluxed for 4 h. After cooling to room temperature the solvent was removed under reduced pressure, the white residue was dissolved in 150 mL of CH$_2$Cl$_2$ and washed with 3×100 mL of water. The organic layer was dried over MgSO$_4$ and filtered. Removal of the solvent under reduced pressure furnished the desired product (1.04 g 5.0×10$^{-3}$ mol, 42% yield) as white solid that was used for the next step without further purifications. An analytical sample was obtained by flash chromatography (CC, SiO$_2$, 100% ethyl acetate, R$_f$(6)=0.26). m.p. 139-141° C. (dec). IR (neat): 3472, 1681, 1435, 1405, 1335, 1269, 1168, 1100, 1053, 1013, 959, 916, 875, 850, 807, 722, 705, 654 cm$^{-1}$. $^1$H NMR (400.03 MHz, CDCl$_3$, 298 K) δ 1.90 (bs, 1H, OH); 2.90 (s, 2H, CH), 3.69-3.72 (m, 2H, CH$_2$), 3.76-3.78 (m, 2H, CH$_2$), 5.28 (t, J=0.9 Hz, 2H, CH), 6.52 (t, J=0.9 Hz, 2H, CH$_{vinyl}$). $^{13}$C{$^1$H} NMR (100.59 MHz, CDCl$_3$, 298 K) δ=41.77 (2C, NCH$_2$), 60.18 (2C, OCH$_2$), 47.50 (2C, CH), 81.04 (2C, CH), 136.60 (2C, CH$_{vinyl}$), 176.97 (2C, C). Anal. Calcd. for C$_{10}$H$_{11}$NO$_4$: C, 57.41; H, 5.30; N, 6.70. Found C, 57.16; H, 5.37; N, 6.62.

2-Bromo-2-Methyl-Propionic Acid 2-(3,5-Diaxo-10-Oxa-4-Aza-Tricyclo[5.2.1.0$^{2,6}$]Dec-8-En-4-Yl)-Ethyl Ester

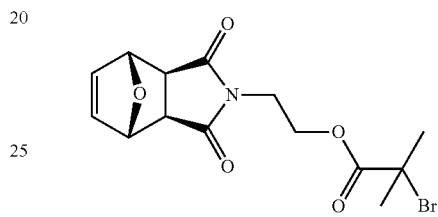

A solution of the alcohol, 4-(2-hydroxy-ethyl)-10-oxa-4-aza-tricyclo[5.2.1.0$^{2,6}$]dec-8-ene-3,5-dione, (2.22 g, 10.6×10$^{-3}$ mol) and Et$_3$N (1.6 mL, 11.7×10$^{-3}$ mol) in 120 mL of THF (the solution remains slightly turbid) was cooled to 0° C. and a solution of 2-bromo isobutiryl bromide (1.4 mL, 11.1×10$^{-3}$ mol) in 40 mL of THF was added dropwise (30 min). The white suspension was stirred for 3 h at 0° C., then at room temperature overnight. The ammonium salt was filtered off and the solvent removed under reduced pressure to give a pale-yellow residue that was purified by flash chromatography (CC, SiO$_2$, petroleum ether/ethyl acetate 1:1, R$_f$(7)=0.23). Obtained 3.54 g (9.88×10$^{-3}$ mol, 93% yield) of initiator 15 as a white solid. m.p. 83-85° C. IR (neat): 1733, 1695, 1419, 1395, 1336, 1278, 1157, 1106, 1015, 874, 852, 824, 724, 706, 654, 603 cm$^{-1}$. $^1$H NMR (400.03 MHz, CDCl$_3$, 298 K) δ=1.86 (s, 6H, CH$_3$), 2.84 (s, 2H, CH), 3.78 (t, J=5.3 Hz, 2H, NCH$_2$); 4.30 (t, J=5.3 Hz, 2H, OCH$_2$); 5.23 (t, J=1.0 Hz, 2H, CHO); 6.49 (t, J=1.0 Hz, 2H, CH$_{vinyl}$). $^{13}$C{$^1$H} NMR (100.59 MHz, CDCl$_3$, 298 K) δ=30.65 (2C, CH$_2$), 37.65 (2C, NCH$_2$), 47.56 (2C, CH), 55.80 (1C, C(CH$_3$)$_2$Br), 62.26 (OCH$_2$), 80.91 (2H, CHO), 136.62 (2C, CH$_{vinyl}$), 171.46 (1C, CO$_{ester}$), 175.95 (2C, CO$_{imide}$). Anal. Calcd. for C$_{14}$H$_{16}$NO$_5$: C, 46.95; H, 4.50; N, 3.91; Br, 22.31. Found C, 46.88; H, 4.55; N, 3.79; Br, 22.22

PREPARATION OF POLYPEG POLYMERS

Polymerisations Using Initiator 8

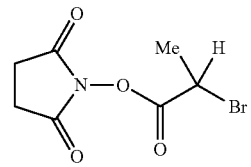

Polymerisation of MPEG(395)MA

[PEG]/[I]/[Cu]/[L]=10/1/1/2 in 50v/v % Toluene Solution at 30° C.

A dry Schlenk tube was charged with Cu(I)Br (0.326 g, $2.27\times10^{-3}$ mol), initiator 8 (0.569 g, $2.27\times10^{-3}$ mol) and a magnetic follower prior to being deoxygenated by cycling between nitrogen and vacuum three times. To a second Schlenk tube was added MPEG(395)MA (10 mL, $22.74\times10^{-3}$ mol), N-(n-ethyl)-2-pyridylmethanimine (0.64 mL, $4.54\times10^{-3}$ mol) and toluene (10 mL). The mixture was immediately subjected to five freeze-pump-thaw degassing cycles. This solution was then transferred to the Schlenk tube containing the initiator and Cu(I)Br via a cannula. The resulting brown solution was stirred at 30° C. Samples were removed periodically using degassed syringes and quenched in liquid nitrogen for conversion and molecular weight analysis.

TABLE 3

Kinetic data for the polymerisation of MPEG(395)MA initiated by 8 in toluene solution (50% v/v) at 30° C. ([MPEG(395)MA]$_0$/[CuBr]$_0$/[NHSBr]$_0$/[ligand]$_0$ = 10/1/1/2).

| Experiment | Time (h) | Conversion (%) | ln([M]$_0$/[M]) | $M_{n,then}$ (g·mol$^{-1}$) | $M_{n,SEC}$ (g·mol$^{-1}$) | $M_w/M_n$ |
|---|---|---|---|---|---|---|
| Toluene | 2 | 4.5 | 0.046 | 230 | 3040 | 1.07 |
| Ethyl Ligand | 4 | 17.3 | 0.190 | 870 | 3710 | 1.30 |
|  | 6 | 30.2 | 0.359 | 1510 | 4480 | 1.13 |
|  | 8 | 40.2 | 0.514 | 2010 | 4950 | 1.11 |
|  | 10 | 49.3 | 0.679 | 2470 | 5530 | 1.10 |
|  | 21 | 92.3 | 2.564 | 4620 | 7980 | 1.09 |

Polymerisation of MPEG(550)MA

[PEG]/[I]/[Cu]/[L]=6.37/1/1/2 in 73 w/v % Toluene Solution at 50/70° C.

Initiator 8 (0.10 g, 0.400 mmol), Cu(I)Br (0.057 g, 0.400 mmol, 1 eq) and MPEG(550)MA, (1.60 g, 2.55 mmol), and a magnetic follower were placed in an oven dried Schlenk tube. The Schlenk tube was evacuated and flushed with dry nitrogen three times. Deoxygenated toluene (5.90 mL) was added to the Schlenk tube. The resulting solution was deoxygenated by bubbling with nitrogen for 1 hour and then degassed N-propyl-2-pyridylmethanimine (0.114 g, 0.797 mmol) was added. The reaction was placed in a thermostatically controlled oil bath at 50° C. (t=0) and samples were removed periodically for conversion and molecular weight analysis. The temperature was increased to 70° C. after 5 hours 32 minutes.

TABLE 4

Data for the polymerization of MPEG(550)MA with initiator 8 at 50/70° C. in 73 w/v % toluene solution.

| Sample Time/minutes | Conversion/% | Mn | PDi |
|---|---|---|---|
| 385 | 15 | 4730 | 1.05 |
| 1357 | 42 | 10440 | 1.10 |
| 1663 | 45 | 10280 | 1.12 |

[PEG]/[I]/[Cu]/[L]=6.37/1/1/2 in 73 w/v % Toluene Solution at 90° C.

Initiator 8 (0.10 g, 0.400 mmol), Cu(I)Br (0.057 g, 0.400 mmol, 1 eq) and MPEG(550)MA (1.60 g, 2.341 mmol), and a magnetic follower were placed in an oven dried Schlenk tube. The Schlenk tube was evacuated and flushed with dry nitrogen three times. Deoxygenated toluene (5.90 mL) was added to the Schlenk tube. The resulting solution was deoxygenated by bubbling with nitrogen for 1 hour and then degassed N-propyl-2-pyridylmethanimine (0.114 g, 0.797 mmol) was added. The reaction was placed in a thermostatically controlled oil bath at 90° C. (t=0) and samples were removed periodically for conversion and molecular weight analysis.

TABLE 5

Data for the polymerization of MPEG(550)MA with initiator 8 at 90° C. in 73 w/v % toluene solution.

| Sample Time/minutes | Conversion/% | Mn | PDi |
|---|---|---|---|
| 138 | 46 | 6950 | 1.09 |
| 240 | 46 | 7220 | 1.12 |
| 314 | 48 | 7370 | 1.12 |
| 1293 | 59 | 7690 | 1.14 |

[PEG]/[I]/[Cu]/[L]=31.9/1/1/2 in 67 v/v % Toluene Solution at 50° C.

Initiator 8 (0.10 g, 0.40 mmol), Cu(I)Br (0.0574 g, 0.40 mmol, 1 eq) and MPEG(550)MA (8.0 g, 12.7 mmol), and a magnetic follower were placed in an oven dried Schlenk tube. The Schlenk tube was evacuated and flushed with dry nitrogen three times. Deoxygenated toluene (14.7 mL) was added to the Schlenk tube. The resulting solution was deoxygenated via three freeze pump thaw cycles and then degassed N-ethyl-2-pyridylmethanimine (0.107 g, 0.80 mmol) was added. The reaction was placed in a thermostatically controlled oil bath at 50° C. (t=0) and samples were removed periodically for conversion and molecular weight analysis. The polymer was purified by removing the solvent in vacuo and dialysising the residue using acidic water (pH ~4). Subsequent freeze drying isolated the product.

TABLE 6

Data for the polymerization of MPEG(550)MA with initiator 8 at 50° C. in 67 v/v % toluene solution.

| Sample Time/minutes | Conversion/% | Mn | PDi |
|---|---|---|---|
| 120 | 7 | 7189 | 1.089 |
| 240 | 15 | 8976 | 1.074 |
| 360 | 20 | 10477 | 1.074 |
| 1320 | 87 | 23051 | 1.147 |

[PEG]/[I]/[Cu]/[L]=6.4/1/1/2 in 67 v/v % Toluene Solution at 50° C.

Initiator 8 (0.10 g, 0.40 mmol), Cu(I)Br (0.0574 g, 0.40 mmol, 1 eq) and MPEG(550)MA (1.60 g, 2.55 mmol), and a magnetic follower were placed in an oven dried Schlenk tube. The Schlenk tube was evacuated and flushed with dry nitrogen three times. Deoxygenated toluene (3.0 mL) was added to the Schlenk tube. The resulting solution was deoxygenated via three freeze pump thaw cycles and then degassed N-ethyl-2-pyridylmethanimine (0.107 g, 0.80 mmol) was added. The reaction was placed in a thermostatically controlled oil bath at 50° C. (t=0) and samples were removed periodically for conversion and molecular weight analysis.

TABLE 7

Data for the polymerization of MPEG(550)MA
with initiator 8 at 50° C. in 67 v/v %
toluene solution.

| Sample Time/minutes | Conversion/% | Mn | PDi |
|---|---|---|---|
| 180 | 13 | 4984 | 1.064 |
| 360 | 31 | 6628 | 1.110 |
| 1320 | 86 | 11282 | 1.104 |

[PEG]/[I]/[Cu(I)]/[Cu(II)]/[L]=6.4/1/0.95/0.05/2 in 67 v/v % Toluene Solution at 50° C.

Initiator 8 (0.10 g, 0.40 mmol), Cu(I)Br (0.0545 g, 0.38 mmol, 0.95 eq), Cu(II)Br (0.0045 g, 0.02 mmol, 0.05 eq), and MPEG(550)MA (1.60 g, 2.55 mmol), and a magnetic follower were placed in an oven dried Schlenk tube. The Schlenk tube was evacuated and flushed with dry nitrogen three times. Deoxygenated toluene (3.0 mL) was added to the Schlenk tube. The resulting solution was deoxygenated via three freeze pump thaw cycles and then degassed N-ethyl-2-pyridylmethanimine (0.107 g, 0.80 mmol) was added. The reaction was placed in a thermostatically controlled oil bath at 50° C. (t=0) and samples were removed periodically for conversion and molecular weight analysis.

TABLE 8

Data for the polymerization of MPEG(550)MA
with initiator 8 at 50° C. in 67 v/v %
toluene solution.

| Sample Time/minutes | Conversion/% | Mn | PDi |
|---|---|---|---|
| 180 | 5 | 4743 | 4743 |
| 360 | 16 | 5904 | 5904 |
| 1320 | 65 | 11202 | 11202 |
| 1800 | 78 | 12245 | 12245 |

[PEG]/[I]/[Cu]/[L]=64/1/1/2 in 67v/v % Toluene Solution at 50° C.

Initiator 8 (0.10 g, 0.40 mmol), Cu(I)Br (0.0574 g, 0.40 mmol, 1 eq) and MPEG(550)MA (1.60 g, 2.55 mmol), and a magnetic follower were placed in an oven dried Schlenk tube. The Schlenk tube was evacuated and flushed with dry nitrogen three times. Deoxygenated toluene (3.0 mL) was added to the Schlenk tube. The resulting solution was deoxygenated via three freeze pump thaw cycles and then degassed N-propyl-2-pyridylmethanimine (0.119 g, 0.80 mmol) was added. The reaction was placed in a thermostatically controlled oil bath at 50° C. (t=0) and samples were removed periodically for conversion and molecular weight analysis.

TABLE 9

Data for the polymerization of MPEG(550)MA
with initiator 8 at 50° C. in 67 v/v %
toluene solution.

| Sample Time/minutes | Conversion/% | Mn | PDi |
|---|---|---|---|
| 180 | 13 | 4875 | 1.041 |
| 360 | 22 | 5601 | 1.087 |
| 1320 | 66 | 9897 | 1.091 |

[PEG]/[I]/[Cu]/[L]=6.4/1/2 in 67 v/v % Toluene Solution at 50° C.

Initiator 8 (0.10 g, 0.40 mmol), Cu(I)Br (0.0574 g, 0.40 mmol, 1 eq) and MPEG(550)MA (1.60 g, 2.55 mmol), and a magnetic follower were placed in an oven dried Schlenk tube. The Schlenk tube was evacuated and flushed with dry nitrogen three times. Deoxygenated toluene (3.0 mL) was added to the Schlenk tube. The resulting solution was deoxygenated via three freeze pump thaw cycles and then degassed N-octyl-2-pyridylmethanimine (0.175 g, 0.80 mmol) was added. The reaction was placed in a thermostatically controlled oil bath at 50° C. (t=0) and samples were removed periodically for conversion and molecular weight analysis.

TABLE 10

Data for the polymerization of MPEG(550)MA
with initiator 8 at 50° C. in 67 v/v %
toluene solution.

| Sample Time/minutes | Conversion/% | Mn | PDi |
|---|---|---|---|
| 180 | 19 | 5034 | 1.075 |
| 360 | 33 | 6636 | 1.101 |
| 1320 | 85 | 11294 | 1.097 |

[PEG]/[I]/[Cu]/[L]=64/1/1/2 in 67 v/v % Toluene Solution at 70° C.

Initiator 8 (0.10 g, 0.40 mmol), Cu(I)Br (0.0574 g, 0.40 mmol, 1 eq) and MPEG(550)MA (1.60 g, 2.55 mmol), and a magnetic follower were placed in an oven dried Schlenk tube. The Schlenk tube was evacuated and flushed with dry nitrogen three times. Deoxygenated toluene (3.0 mL) was added to the Schlenk tube. The resulting solution was deoxygenated via three freeze pump thaw cycles and then degassed N-ethyl-2-pyridylmethanimine (0.107 g, 0.80 mmol) was added. The reaction was placed in a thermostatically controlled oil bath at 70° C. (t=0) and samples were removed periodically for conversion and molecular weight analysis.

TABLE 11

Data for the polymerization of MPEG(550)MA
with initiator 8 at 70° C. in 67 v/v %
toluene solution.

| Sample Time/minutes | Conversion/% | Mn | PDi |
|---|---|---|---|
| 60 | 20 | 5455 | 1.096 |
| 120 | 52 | 7898 | 1.114 |
| 180 | 73 | 9544 | 1.086 |
| 240 | 80 | 10207 | 1.095 |

[PEG]/[I]/[Cu]/[L]==6.4/1/112 in 67 v/v % Toluene Solution at 50° C.

Initiator 8 (6.0 g, 24 mmol), Cu(I)Br (3.44 g, 24 mmol, 1 eq) and MPEG(550)MA (96 g, 0.153 mol), and a magnetic follower were placed in an oven dried Schlenk tube. The Schlenk tube was evacuated and flushed with dry nitrogen three times. Deoxygenated toluene (176 mL) was added to the Schlenk tube. The resulting solution was deoxygenated by bubbling with nitrogen for 1 hour and then degassed N-ethyl-2-pyridylmethanimine (6.44 g, 48 mmol) was added. The reaction was placed in a thermostatically controlled oil bath at 50° C. (t=0) and samples were removed periodically for conversion and molecular weight analysis. The polymer was purified by removing the solvent in vacuo and dialysising the residue using acidic water (pH ~4). Subsequent freeze drying isolated the product.

TABLE 12

Data for the polymerization of MPEG(550)MA with initiator 8 at 50° C. in 67 v/v % toluene solution.

| Sample Time/minutes | Conversion/% | Mn | PDi |
|---|---|---|---|
| 1200 | 66 | 8207 | 1.118 |
| 1500 | 75 | 9276 | 1.082 |
| 1680 | 81 | 9342 | 1.096 |

[PEG]/[I]/[Cu]/[L]==23.2/1/1/2 in 80 v/v % Toluene Solution at 50° C.

Initiator 8 (0.10 g, 0.40 mmol), Cu(I)Br (0.0574 g, 0.40 mmol, 1 eq) and MPEG(1000)MA (10.0 g, 9.3 mmol), and a magnetic follower were placed in an oven dried Schlenk tube. The Schlenk tube was evacuated and flushed with dry nitrogen three times. Deoxygenated toluene (40 mL) was added to the Schlenk tube. The resulting solution was deoxygenated by bubbling with nitrogen for 1 hour and then degassed N-ethyl-2-pyridylmethanimine (0.107 g, 0.80 mmol) was added. The reaction was placed in a thermostatically controlled oil bath at 50° C. (t—0) and samples were removed periodically for conversion and molecular weight analysis. The polymer was purified by removing the solvent in vacuo and dialysising the residue using acidic water (pH ~4). Subsequent freeze drying isolated the product.

TABLE 13

Data for the polymerization of MPEG(1000)MA with initiator 8 at 50° C. in 80 w/v % toluene solution.

| Sample Time/minutes | Conversion/% | Mn | PDi |
|---|---|---|---|
| 300 | 3 | 9760 | 1.056 |
| 1260 | 41 | 19436 | 1.087 |
| 3000 | 79 | 29013 | 1.132 |
| 7020 | 87 | 30046 | 1.149 |

[PEG]/[I]/[Cu]/[L]==46.3/1/1/2 in 80 v/v % Toluene Solution at 50° C.

Initiator 8 (0.10 g, 0.40 mmol), Cu(I)Br (0.0574 g, 0.40 mmol, 1 eq) and MPEG(1000)MA (20.0 g, 18.5 mmol), and a magnetic follower were placed in an oven dried Schlenk tube. The Schlenk tube was evacuated and flushed with dry nitrogen three times. Deoxygenated toluene (80 mL) was added to the Schlenk tube. The resulting solution was deoxygenated by bubbling with nitrogen for 1 hour and then degassed N-ethyl-2-pyridylmethanimine (0.107 g, 0.80 mmol) was added. The reaction was placed in a thermostatically controlled oil bath at 50° C. (t=0) and samples were removed periodically for conversion and molecular weight analysis. The polymer was purified by removing the solvent in vacuo and dialysising the residue using acidic water (pH ~4). Subsequent freeze drying isolated the product.

TABLE 14

Data for the polymerization of MPEG(1000)MA with initiator 8 at 50° C. in 80 w/v % toluene solution.

| Sample Time/minutes | Conversion/% | Mn | PDi |
|---|---|---|---|
| 300 | 4 | 11014 | 1.070 |
| 1260 | 15 | 14388 | 1.080 |
| 3000 | 31 | 26378 | 1.096 |
| 7020 | 53 | 33388 | 1.154 |

[PEG]/[I]/[Cu]/[L]==23.2/1/1/2 in 80 w/v % Toluene Solution at 50° C.

Initiator 8 (1.0 g, 4.0 mmol), Cu(I)Br (0.574 g, 4.0 mmol, 1 eq) and MPEG(1000)MA (100 g, 93.0 mmol), and a magnetic follower were placed in an oven dried Schlenk tube. The Schlenk tube was evacuated and flushed with dry nitrogen three times. Deoxygenated toluene (200 mL) was added to the Schlenk tube. The resulting solution was deoxygenated by bubbling with nitrogen for 1 hour and then degassed N-ethyl-2-pyridylmethanimine (1.07 g, 8.0 mmol) was added. The reaction was placed in a thermostatically controlled oil bath at 50° C. (t=0) and samples were removed periodically for conversion and molecular weight analysis. The polymer was purified by removing the solvent in vacuo and dialysising the residue using acidic water (pH ~4). Subsequent freeze drying isolated the product.

TABLE 15

Data for the polymerization of MPEG(1000)MA with initiator 8 at 50° C. in 80 w/v % toluene solution.

| Sample Time/minutes | Conversion/% | Mn | PDi |
|---|---|---|---|
| 4320 | 89 | 37676 | 1.143 |

Polymerisations Using Initiator 7

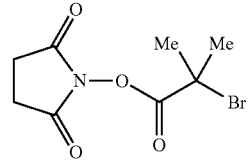

7

Polymerisation of MPEG(395)MA

[PEG]/[I]/[Cu]/[L]=10/1/1/2 in 50 v/v % Toluene Solution at 30° C.

A dry Schlenk tube was charged with Cu(I)Br (0.326 g, 2.27 mmol), initiator 7 (0.601 g, 2.27 mmol) and a magnetic follower prior to being deoxygenated by cycling between nitrogen and vacuum three times. To a second Schlenk tube was added MPEG(395)MA (10 mL, 22.74 mmol), N-(n-propyl)-2-pyridylmethanimine (0.71 mL, 4.54 mmol) and toluene (10 mL). The mixture was immediately subjected to five freeze-pump-thaw degassing cycles. This solution was then transferred to the Schlenk tube containing the initiator and Cu(I)Br via a cannula. The resulting brown solution was stirred at 30° C. Samples were removed periodically using degassed syringes and quenched in liquid nitrogen for conversion and molecular weight analysis.

TABLE 16

Kinetic data for the polymerisation of MPEG(395)MA initiated by 7 in toluene solution (50% v/v) at 30° C. ([MPEG(395)MA]$_0$/[CuBr]$_0$/[NHSBr]$_0$/[ligand]$_0$ = 10/1/1/2).

| Solvent/ Ligand | Time (h) | Conversion (%) | ln([M]$_0$/ [M]) | M$_{n,theo}$ (g·mol$^{-1}$) | M$_{n,SEC}$ (g·mol$^{-1}$) | M$_w$/M$_n$ |
|---|---|---|---|---|---|---|
| Toluene Propyl ligand | 1 | 8.9 | 0.0933 | 450 | 2350 | 1.10 |
|  | 2 | 18.4 | 0.204 | 920 | 2860 | 1.26 |
|  | 3 | 27.1 | 0.316 | 1360 | 3100 | 1.20 |
|  | 4 | 34.7 | 0.4259 | 1740 | 3600 | 1.13 |
|  | 17 | 80.8 | 1.6510 | 4050 | 5670 | 1.06 |

[PEG]/[I]/[Cu]/[L]=10/1/1/2 in 50 v/v % Anisole Solution at 30° C.

A dry Schlenk tube was charged with Cu(I)Br (0.326 g, 2.27 mmol), initiator 7 (0.601 g, 2.27 mmol) and a magnetic follower prior to being deoxygenated by cycling between nitrogen and vacuum three times. To a second Schlenk tube was added MPEG(395)MA (10 mL, 22.74 mmol), N-(n-ethyl)-2-pyridylmethanimine (0.64 mL, 4.54 mmol) and anisole (10 mL). The mixture was immediately subjected to five freeze-pump-thaw degassing cycles. This solution was then transferred to the Schlenk tube containing the initiator and Cu(I)Br via a cannula. The resulting brown solution was stirred at 30° C. Samples were removed periodically using degassed syringes and quenched in liquid nitrogen for conversion and molecular weight analysis.

TABLE 17

Kinetic data for the polymerisation of MPEG(395)MA initiated by 7 in anisole solution (50% v/v) at 30° C. ([MPEG(395)MA]$_0$/[CuBr]$_0$/[NHSBr]$_0$/[ligand]$_0$ = 10/1/1/2).

| Solvent/ Ligand | Time (h) | Conversion (%) | ln([M]$_0$/ [M]) | M$_{n,theo}$ (g·mol$^{-1}$) | M$_{n,SEC}$ (g·mol$^{-1}$) | M$_w$/M$_n$ |
|---|---|---|---|---|---|---|
| Anisole Ethyl ligand | 2 | 17.0 | 0.1861 | 850 | 2670 | 1.11 |
|  | 4 | 26.8 | 0.3116 | 1340 | 3460 | 1.12 |
|  | 6 | 34.8 | 0.4277 | 1740 | 4260 | 1.11 |
|  | 22 | 81.4 | 1.6809 | 4080 | 6350 | 1.06 |

[PEG]/[I]/[Cu]/[L]=10/1/1/2 in 50 v/v % Anisole Solution at 30° C.

A dry Schlenk tube was charged with Cu(I)Br (0.326 g, 2.27 mmol), initiator 7 (0.601 g, 2.27 mmol) and a magnetic follower prior to being deoxygenated by cycling between nitrogen and vacuum three times. To a second Schlenk tube was added MPEG(395)MA (10 mL, 22.74 mmol), N-(n-propyl)-2-pyridylmethanimine (0.71 mL, 4.54 mmol) and anisole (10 mL). The mixture was immediately subjected to five freeze-pump-thaw degassing cycles. This solution was then transferred to the Schlenk tube containing the initiator and Cu(I)Br via a cannula. The resulting brown solution was stirred at 30° C. Samples were removed periodically using degassed syringes and quenched in liquid nitrogen for conversion and molecular weight analysis.

TABLE 18

Kinetic data for the polymerisation of MPEG(395)MA initiated by 7 in anisole solution (50% v/v) at 30° C. ([MPEG(395)MA]$_0$/[CuBr]$_0$/[NHSBr]$_0$/[ligand]$_0$ = 10/1/1/2).

| Solvent/ Ligand | Time (h) | Conversion (%) | ln([M]$_0$/ [M]) | M$_{n,theo}$ (g·mol$^{-1}$) | M$_{n,SEC}$ (g·mol$^{-1}$) | M$_w$/M$_n$ |
|---|---|---|---|---|---|---|
| Anisole Propyl ligand | 2 | 9.8 | 0.1030 | 490 | 2070 | 1.10 |
|  | 4 | 16.8 | 0.1837 | 842 | 2480 | 1.12 |
|  | 6 | 28.7 | 0.3378 | 1440 | 2870 | 1.13 |
|  | 27 | 83.4 | 1.7985 | 4180 | 6280 | 1.06 |

Polymerisation of MPEG(550)MA
[PEG]/[I]/[Cu]/[L]=6.4/1/1/2 in 66 w/v % Toluene Solution at 30° C.

Initiator 7 (0.5 g, 1.89 mmol), Cu(I)Br (0.27 g, 1.89 mmol, 1 eq) and MPEG(550)MA (7.57 g, 0.012 mol), and a magnetic follower were placed in an oven dried Schlenk tube. The Schlenk tube was evacuated and flushed with dry nitrogen three times. Deoxygenated toluene (14 mL) was added to the Schlenk tube. The resulting solution was deoxygenated via three freeze pump thaw cycles and then degassed N-ethyl-2-pyridylmethanimine (0.51 g, 3.79 mmol) was added. The reaction was placed in a thermostatically controlled oil bath at 30° C. (t=0) and samples were removed periodically for conversion and molecular weight analysis.

TABLE 19

Data for the polymerization of MPEG(550)MA with initiator 7 at 30° C. in 66 w/v % toluene solution.

| Sample Time/ minutes | Conversion/ % | Mn | PDi |
|---|---|---|---|
| 60 | 19 | 2850 | 1.04 |
| 131 | 32 | 3230 | 1.10 |
| 199 | 45 | 3560 | 1.12 |
| 250 | 53 | 3760 | 1.12 |
| 298 | 56 | 3980 | 1.12 |

[PEG]/[I]/[Cu]/[L]=6.4/1/1/2 in 66 w/v % Toluene Solution at 50° C.

Initiator 7 (0.5 g, 1.89 mmol), Cu(I)Br (0.27 g, 1.89 mmol, 1 eq) and MPEG(550)MA (7.57 g, 0.012 mol), and a magnetic follower were placed in an oven dried Schlenk tube. The Schlenk tube was evacuated and flushed with dry nitrogen three times. Deoxygenated toluene (15 mL) was added to the Schlenk tube. The resulting solution was deoxygenated via three freeze pump thaw cycles and then degassed N-ethyl-2-pyridylmethanimine (0.51 g, 3.79 mmol) was added. The reaction was placed in a thermostatically controlled oil bath at 50° C. (t=0) and samples were removed periodically for conversion and molecular weight analysis.

TABLE 20

Data for the polymerization of MPEG(550)MA with initiator 7 at 50° C. in 66 w/v % toluene solution.

| Sample Time/ minutes | Conversion/ % | Mn | PDi |
|---|---|---|---|
| 59 | 39 | 3212 | 1.09 |
| 126 | 56 | 3958 | 1.11 |
| 195 | 69 | 4375 | 1.13 |
| 246 | 75 | 4649 | 1.13 |
| 295 | 82 | 4874 | 1.13 |

[PEG]/[I]/[Cu]/[L]=23.9/1/1/2 in 66 w/v % Toluene Solution at 90° C.

Initiator 7 (2.5 g, 9.47 mmol), Cu(I)Br (1.35 g, 9.47 mmol, 1 eq) and MPEG(550)MA (142.0 g, 0.226 mol), and a magnetic follower were placed in an oven dried Schlenk tube. The Schlenk tube was evacuated and flushed with dry nitrogen three times. Deoxygenated toluene (261 mL) was added to the Schlenk tube. The resulting solution was deoxygenated via three freeze pump thaw cycles and then degassed N-propyl-2-pyridylmethanimine (2.80 g, 0.019 mol) was added. The reaction was placed in a thermostatically controlled oil bath at 90° C. (t=0) and samples were removed periodically for conversion and molecular weight analysis The polymer was purified by the dropwise addition of the reaction solution to a vigorously stirred solution of diethyl ether (1000 mL). The resulting oil was washed with diethyl ether (3×1000 mL) and then dried in vacuo.

TABLE 21

Data for the polymerization of MPEG(550)MA with initiator 7 at 90° C. in 66 w/v % toluene solution.

| Sample Time/ minutes | Conversion/ % | Mn | PDi |
| --- | --- | --- | --- |
| 48 | 21 | 4449 | 1.11 |
| 132 | 40 | 7198 | 1.08 |
| 185 | 44 | 7779 | 1.07 |
| 245 | 46 | 8105 | 1.09 |
| 300 | 48 | 8331 | 1.09 |

[PEG]/[I]/[Cu]/[L]=6.4/1/1/2 in 66 w/v % Toluene Solution at 50° C.

Initiator 7 (10.0 g, 0.038 mol), Cu(I)Br (5.41 g, 0.038 mol, 1 eq) and MPEG(550)MA (151.0 g, 0.240 mol), and a magnetic follower were placed in an oven dried Schlenk tube. The Schlenk tube was evacuated and flushed with dry nitrogen three times. Deoxygenated toluene (302 mL) was added to the Schlenk tube. The resulting solution was deoxygenated by bubbling with nitrogen for 1 hour and then degassed N-ethyl-2-pyridylmethanimine (10.2 g, 0.0761 mol) was added. The reaction was placed in a thermostatically controlled oil bath at 50° C. (t=0). Conversion was followed by $^1$H NMR spectrometry and molecular weight analysis by SEC.

TABLE 22

Data for the polymerization of MPEG(550)MA with initiator 7 at 50° C. in 66 w/v % toluene solution.

| Sample Time/ minutes | Conversion/ % | Mn | PDi |
| --- | --- | --- | --- |
| 235 | 86.4 | 5140 | 1.13 |

[PEG]/[I]/[Cu]/[L]=6.46/1/1/2 in 62 w/v % Toluene at 50° C.

Initiator 7 (2.95 g, $1.119 \times 10^{-2}$ mol), Cu(I)Br (1.60 g, $1.119 \times 10^{-2}$ mol) and MPEG(550)MA (45.42 g, $7.23 \times 10^{-2}$ mol) and a magnetic follower were placed in an oven dried Schlenk tube. The Schlenk tube was evacuated and flushed with dry nitrogen three times. Toluene (73 mL) was then added to the Schlenk tube and the mixture degassed via three consecutive freeze, pump, thaw cycles. On completion deoxygenated N-ethyl-2-pyridylmethanimine (3.16 mL, $2.24 \times 10^{-2}$ mol) was added and the Schlenk placed in a thermostatically controlled oil bath at 50° C. (t=0) and sampled for conversion and molecular weight analysis. The polymer was isolated by washing with diethyl ether and subsequently dialysed in acidified water (pH ~4)

TABLE 23

Data for the polymerization of MPEG(550)MA with initiator 7 at 50° C. in 62 w/v % toluene solution.

| Sample Time/ minutes | Conversion/ % | Mn | PDi |
| --- | --- | --- | --- |
| 300 | 84.9 | 4590 | 1.22 |

[PEG]/[I]/[Cu]/[L]==23.9/1/1/2 in 67 w/v % Toluene Solution at 50° C.

Initiator 7 (0.05 g, 0.189 mmol), Cu(I)Br (0.027 g, 0.189 mmol, 1 eq), 2,2'-bipyridyl (0.059 g, 0.378 mmol), MPEG(550)MA, (2.84 g, 4.52 mmol) and a magnetic follower were placed in an oven dried Schlenk tube. The Schlenk tube was evacuated and flushed with dry nitrogen three times. Deoxygenated toluene (5.68 mL) was added to the Schlenk tube and the resulting solution was deoxygenated via three freeze pump thaw cycles. The reaction was placed in a thermostatically controlled oil bath at 50° C. (t=0) and samples were removed periodically for conversion and molecular weight analysis.

TABLE 24

Data for the polymerization of MPEG(550)MA with initiator 7 at 50° C. in 67 w/v % toluene solution using 2,2'-bipyridyl ligand.

| Sample Time/ minutes | Conversion/ % | Mn | PDi |
| --- | --- | --- | --- |
| 240 | 85 | 15443 | 1.11 |

[PEG]/[I]/[Cu]/[L]=23.9/1/1/2 in 67 w/v % Toluene Solution at 50° C.

Initiator 7 (0.05 g, 0.189 mmol), Cu(I)Br (0.027 g, 0.189 mmol, 1 eq), 4,4'-dinonyl-2,2'-dipyridyl (0.1545 g, 0.378 mmol), MPEG(550)MA, (2.84 g, 4.52 mmol) and a magnetic follower were placed in an oven dried Schlenk tube. The Schlenk tube was evacuated and flushed with dry nitrogen three times. Deoxygenated toluene (5.68 mL) was added to the Schlenk tube and the resulting solution was deoxygenated via three freeze pump thaw cycles. The reaction was placed in a thermostatically controlled oil bath at 50° C. (t=0) and samples were removed periodically for conversion and molecular weight analysis.

TABLE 25

Data for the polymerization of MPEG(550)MA with initiator 7 at 50° C. in 67 w/v % toluene solution using 4,4'-dinonyl-2,2'-dipyridyl ligand.

| Sample Time/ minutes | Conversion/ % | Mn | PDi |
| --- | --- | --- | --- |
| 240 | 79 | 15936 | 1.16 |

[PEG]/[I]/[Cu]/[L]=23.9/1/1/1 in 67 w/v % Toluene Solution at 50° C.

Initiator 7 (0.05 g, 0.189 mmol), Cu(I)Br (0.027 g, 0.189 mmol, 1 eq), 1,1,4,7,10,10-hexamethyltriethylenetetramine (0.0435 g, 0.189 mmol), MPEG(550)MA, (2.84 g, 4.52 mmol) and a magnetic follower were placed in an oven dried Schlenk tube. The Schlenk tube was evacuated and flushed with dry nitrogen three times. Deoxygenated toluene (5.68 mL) was added to the Schlenk tube and the resulting solution was deoxygenated via three freeze pump thaw cycles. The reaction was placed in a thermostatically controlled oil bath at 50° C. (t=0) and samples were removed periodically for conversion and molecular weight analysis.

TABLE 26

Data for the polymerization of MPEG(550)MA with initiator 7 at 50° C. in 67 w/v % toluene solution using 1,1,4,7,10,10-hexamethyltriethylenetetramine ligand.

| Sample Time/ minutes | Conversion/ % | Mn | PDi |
|---|---|---|---|
| 240 | 86 | 19060 | 1.16 |

[PEG]/[I]/[Cu]/[L]=23.9/1/1/1 in 67 w/v % Toluene Solution at 50° C.

Initiator 7 (0.05 g, 0.189 mmol), Cu(I)Br (0.027 g, 0.189 mmol, 1 eq), N,N,N',N'',N''-pentamethyldiethylenetriamine (0.0328 g, 0.189 mmol), MPEG(550)MA, (2.84 g, 4.52 mmol) and a magnetic follower were placed in an oven dried Schlenk tube. The Schlenk tube was evacuated and flushed with dry nitrogen three times. Deoxygenated toluene (5.68 mL) was added to the Schlenk tube and the resulting solution was deoxygenated via three freeze pump thaw cycles. The reaction was placed in a thermostatically controlled oil bath at 50° C. (t=0) and samples were removed periodically for conversion and molecular weight analysis.

TABLE 27

Data for the polymerization of MPEG(550)MA with initiator 7 at 50° C. in 67 w/v % toluene solution using N,N,N',N'',N''-pentamethyldiethylenetriamine ligand.

| Sample Time/ minutes | Conversion/ % | Mn | PDi |
|---|---|---|---|
| 240 | 95 | 19019 | 1.20 |

Polymerisation of MPEG(1000)MA

[PEG]/[I]/[Cu]/[L]=13.9/1/1/2 in 66 w/v % Toluene Solution at 90° C.

Initiator 7 (0.526 g, 1.99 mmol), Cu(I)Br (0.29 g, 2.02 mmol, 1 eq) and MPEG(1000)MA (29.62 g, 0.027 mol), and a magnetic follower were placed in an oven dried Schlenk tube. The Schlenk tube was evacuated and flushed with dry nitrogen three times. Deoxygenated toluene (60 mL) was added to the Schlenk tube. The resulting solution was deoxygenated via three freeze pump thaw cycles and then degassed N-ethyl-2-pyridylmethanimine (0.51 g, 3.96 mol) was added. The reaction was placed in a thermostatically controlled oil bath at 90° C. (t=0) and samples were removed periodically for conversion and molecular weight analysis.

The polymer was purified by the dropwise addition of the reaction solution to a vigorously stirred solution of diethyl ether (1000 mL). The resulting oil was washed with diethyl ether (3×1000 mL) and then dried in vacuo.

TABLE 28

Data for the polymerization of MPEG(1000)MA with initiator 7 at 90° C. in 66 w/v % toluene solution.

| Sample Time/ minutes | Conversion/ % | Mn | PDi |
|---|---|---|---|
| 1250 | 47.3 | 12180 | 1.16 |
| 2460 | 50.4 | 12460 | 1.16 |
| 3890 | 52.8 | 12540 | 1.20 |

[PEG]/[I]/[Cu]/[L]=9.01/0.24/0.24 in 75 w/v % Toluene Solution at 50° C.

Initiator 7 (5.0 g, 0.019 mol), Cu(I)Br (0.66 g, 4.61 mmol, 0.24 eq) and MPEG(1000)MA (185.0 g, 0.171 mol), and a magnetic follower were placed in an oven dried Schlenk tube. The Schlenk tube was evacuated and flushed with dry nitrogen three times. Deoxygenated toluene (740 mL) was added to the Schlenk tube. The resulting solution was deoxygenated by bubbling with nitrogen for 1 hour and then degassed N-ethyl-2-pyridylmethanimine (1.24 g, 9.24 mmol) was added. The reaction was placed in a thermostatically controlled oil bath at 50° C. (t=0) and samples were removed periodically for conversion and molecular weight analysis.

TABLE 29

Data for the polymerization of MPEG(1000)MA with initiator 7 at 50° C. in 75 w/v % toluene solution.

| Sample Time/ minutes | Conversion/ % | Mn | PDi |
|---|---|---|---|
| 60 | 7 | 5650 | 0.93 |
| 120 | 11 | 5595 | 0.97 |
| 285 | 20 | 6315 | 1.02 |
| 1340 | 43 | 7993 | 1.08 |
| 7476 | 63 | 9543 | 1.06 |

[PEG]/[I]/[Cu]/[L]=18.5/1/1/2 in 75 w/v % Toluene Solution at 50° C.

Initiator 7 (1.0 g, 3.79 mmol), Cu(I)Br (0.54 g, 3.79 mmol, 1 eq) and MPEG(1000)MA (151.4 g, 0.140 mol), and a magnetic follower were placed in an oven dried Schlenk tube. The Schlenk tube was evacuated and flushed with dry nitrogen three times. Deoxygenated toluene (608 mL) was added to the Schlenk tube. The resulting solution was deoxygenated by bubbling with nitrogen for 1 hour and then degassed N-ethyl-2-pyridylmethanimine (1.02 g, 7.57 mmol) was added. The reaction was placed in a thermostatically controlled oil bath at 50° C. (t=0) and samples were removed periodically for conversion and molecular weight analysis.

TABLE 30

Data for the polymerization of MPEG(1000)MA with initiator 7 at 50° C. in 75 w/v % toluene solution.

| Sample Time/ minutes | Conversion/ % | Mn | PDi |
|---|---|---|---|
| 4005 | 100 | 8607 | 1.32 |

[PEG]/[I]/[Cu]/[L]=18.5/1/1/2 in 75 w/v % Toluene Solution at 50° C.

Initiator 7 (2.0 g, 7.57 mmol), Cu(I)Br (1.08 g, 7.57 mmol, 1 eq) MPEG(1000)MA (151.47 g, 0.140 mol), and a magnetic follower were placed in an oven dried Schlenk tube. The Schlenk tube was evacuated and flushed with dry nitrogen three times. Deoxygenated toluene (606 mL) was added to the Schlenk tube. The resulting solution was deoxygenated by bubbling with nitrogen for 1 hour and then degassed N-ethyl-2-pyridylmethanimine (2.03 g, 0.015 mol) was added. The reaction was placed in a thermostatically controlled oil bath at 50° C. (t=0) and samples were removed periodically for conversion and molecular weight analysis.

TABLE 31

Data for the polymerization of MPEG(1000)MA with initiator 7 at 50° C. in 75 w/v % toluene solution.

| Sample Time/ minutes | Conversion/ % | Mn | PDi |
|---|---|---|---|
| 195 | 20 | 7270 | 1.04 |
| 1380 | 53 | 11964 | 1.08 |
| 2735 | 73 | 13945 | 1.08 |

Polymerisation of MPEG(2000)MA

[PEG]/[I]/[Cu]/[L]=19.2/1/1/2 in 80 w/v % toluene solution at 30° C.

Initiator 7 (0.05 g, 0.189 mmol), Cu(I)Br (0.027 g, 0.189 mmol, 1 eq) and (MPEG(2000)MA) (7.55 g, 3.63 mmol), and a magnetic follower were placed in an oven dried Schlenk tube. The Schlenk tube was evacuated and flushed with dry nitrogen three times. Deoxygenated toluene (28 mL) was added to the Schlenk tube. The resulting solution was deoxygenated via three freeze pump thaw cycles and then degassed N-ethyl-2-pyridylmethanimine (0.05 g, 0.38 mmol) was added. The reaction was placed in a thermostatically controlled oil bath at 30° C. (t=0) and samples were removed periodically for conversion and molecular weight analysis.

The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). This procedure was repeated three times.

TABLE 32

Data for the polymerization of MPEG(2000)MA with initiator 7 at 30° C. in 80 w/v % toluene solution.

| Sample Time/ minutes | Conversion/ % | Mn | PDi |
|---|---|---|---|
| 89 | 4 | 3380 | 1.04 |
| 291 | 9 | 9820 | 1.09 |
| 901 | 17 | 10030 | 1.07 |
| 1369 | 23 | 11080 | 1.07 |
| 2760 | 26 | 12610 | 1.07 |
| 3965 | 28 | 14830 | 1.04 |

[PEG]/[I]/[Cu]/[L]=19.2/1/1/2 in 80 w/v % Toluene Solution at 50° C.

Initiator 7 (0.05 g, 0.189 mmol), Cu(I)Br (0.027 g, 0.189 mmol, 1 eq) and MPEG(2000)MA (7.55 g, 3.63 mmol), and a magnetic follower were placed in an oven dried Schlenk tube. The Schlenk tube was evacuated and flushed with dry nitrogen three times. Deoxygenated toluene (28 mL) was added to the Schlenk tube. The resulting solution was deoxygenated via three freeze pump thaw cycles and then degassed N-ethyl-2-pyridylmethanimine (0.05 g, 0.38 mmol) was added. The reaction was placed in a thermostatically controlled oil bath at 50° C. (t=0) and samples were removed periodically for conversion and molecular weight analysis. The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). This procedure was repeated three times.

TABLE 33

Data for the polymerization of MPEG(2000)MA with initiator 7 at 50° C. in 80 w/v % toluene solution.

| Sample Time/ minutes | Conversion/ % | Mn | PDi |
|---|---|---|---|
| 86 | 7 | 8700 | 1.06 |
| 289 | 12 | 10920 | 1.07 |
| 899 | 24 | 14450 | 1.05 |
| 1367 | 33 | 15810 | 1.04 |
| 2758 | 45 | 20220 | 1.07 |
| 3962 | 53 | 23180 | 1.07 |

[PEG]/[I]/[Cu]/[L]=19.2/1/1/2 in 80 w/v % Toluene Solution at 90° C.

Initiator 7 (0.05 g, 0.189 mmol), Cu(I)Br (0.027 g, 0.189 mmol, 1 eq) and MPEG(2000)MA (7.55 g, 3.63 mmol), and a magnetic follower were placed in an oven dried Schlenk tube. The Schlenk tube was evacuated and flushed with dry nitrogen three times. Deoxygenated toluene (28 mL) was added to the Schlenk tube. The resulting solution was deoxygenated via three freeze pump thaw cycles and then degassed N-ethyl-2-pyridylmethanimine (0.05 g, 0.38 mmol) was added. The reaction was placed in a thermostatically controlled oil bath at 90° C. (t=0) and samples were removed periodically for conversion and molecular weight analysis. The polymer was purified by the dropwise addition of the reaction solution to a vigorously stirred solution of diethyl ether (400 mL). The resulting white powder was filtered, dissolved in toluene (20 mL) and precipitated in diethyl ether (400 mL). this procedure was repeated three times.

TABLE 34

Data for the polymerization of MPEG(2000)MA with initiator 7 at 90° C. in 80 w/v % toluene solution.

| Sample Time/ minutes | Conversion/ % | Mn | PDi |
|---|---|---|---|
| 86 | 18 | 11100 | 1.08 |
| 289 | 26 | 14870 | 1.08 |
| 899 | 31 | 17900 | 1.08 |
| 1367 | 35 | 18110 | 1.09 |
| 2758 | 38 | 18110 | 1.09 |
| 3962 | 39 | 18240 | 1.08 |

[PEG]/[I]/[Cu]/[L]==9.3/1/1/2 in 66 w/v % Toluene Solution at 90° C.

Initiator 7 (0.5 g, 1.89 mmol), Cu(I)Br (0.27 g, 1.89 mmol, 1 eq) and MPEG(1000)MA (18.90 g, 0.018 mol), and a magnetic follower were placed in an oven dried Schlenk tube. The Schlenk tube was evacuated and flushed with dry nitrogen three times. Deoxygenated toluene (35 mL) was added to the Schlenk tube. The resulting solution was deoxygenated via three freeze pump thaw cycles and then degassed N-ethyl-2-pyridylmethanimine (0.51 g, 3.79 mmol) was added. The reaction was placed in a thermostatically controlled oil bath at 90° C. (t=0) and samples were removed periodically for conversion and molecular weight analysis.

TABLE 35

Data for the polymerization of MPEG(1000)MA with initiator 7 at 90° C. in 66 w/v % toluene solution.

| Sample Time/ minutes | Conversion/ % | Mn | PDi |
|---|---|---|---|
| 4160 | 88.7 | 9870 | 1.22 |

[PEG]/[I]/[Cu]/[L]=19.2/1/1/2 in 80 w/v % Toluene Solution at 50/70° C.

Initiator 7 (0.67 g, 2.53 mmol), Cu(I)Br (0.36 g, 2.53 mmol, 1 eq) and MPEG(2000)MA (101.24 g, 0.049 mol), and a magnetic follower were placed in an oven dried Schlenk tube. The Schlenk tube was evacuated and flushed with dry nitrogen three times. Deoxygenated toluene (405 mL) was added to the Schlenk tube. The resulting solution was deoxygenated via three freeze pump thaw cycles and then degassed N-ethyl-2-pyridylmethanimine (0.68 g, 5.07 mmol) was added. The reaction was placed in a thermostatically controlled oil bath at 50° C. (t=0) and samples were removed periodically for conversion and molecular weight analysis. The temperature was increased to 70° C. after 45 hours 15 minutes.

TABLE 36

Data for the polymerization of MPEG(2000)MA with initiator 7 at 50/70° C. in 80 w/v % toluene solution.

| Sample Time/ minutes | Conversion/ % | Mn | PDi |
|---|---|---|---|
| 4030 | 47 | 24,600 | 1.06 |

[PEG]/[I]/[Cu]/[L]=19.2/1/1/2 in 75 w/v % Toluene at 50/70° C.

Initiator 7 (0.66 g, 2.5×10⁻³ mol), Cu(I)Br (0.36 g, 2.5×10⁻³ mol) and MPEG(2000)MA (100.0 g, 4.81×10⁻² mol) and a magnetic follower were placed in an oven dried Schlenk tube. The Schlenk tube was evacuated and flushed with dry nitrogen three times. Toluene (300 mL) was then added to the Schlenk tube and the mixture deoxygenated by purging with nitrogen for 1 hour. Deoxygenated N-ethyl-2-pyridylmethanimine (0.706 mL, 5.0×10⁻³ mol) was then added and the Schlenk placed in a thermostatically controlled oil bath at 50° C. (t=0). The temperature was increased to 70° C. after 24 hours. The polymer was isolated by washing with diethyl ether and subsequently dialysed in acidified water (pH ~4).

TABLE 37

Data for the polymerization of MPEG(2000)MA with initiator 7 at 50/70° C. in 75 w/v % toluene solution.

| Sample Time/ minutes | Conversion/ % | Mn | PDi |
|---|---|---|---|
| 2880 | 94.2 | 21900 | 1.21 |

[PEG]/[I]/[Cu]/[L]=28.8/1/1/2 in 75 w/v % Toluene at 50/70° C.

Initiator 7 (0.44 g, 1.67×10⁻³ mol), Cu(I)Br (0.24 g, 1.67×10⁻³ mol) and MPEG(2000)MA (100.0 g, 4.81×10⁻² mol) and a magnetic follower were placed in an oven dried Schlenk tube. The Schlenk tube was evacuated and flushed with dry nitrogen three times. Toluene (300 mL) was then added to the Schlenk tube and the mixture deoxygenated by purging with nitrogen for 1 hour. Deoxygenated N-ethyl-2-pyridylmethanimine (0.47 mL, 3.33×10⁻³ mol) was then added and the Schlenk placed in a thermostatically controlled oil bath at 50° C. C (t=0). The temperature was increased to 70° C. after 24 hours. The polymer was isolated by washing with diethyl ether and subsequently dialysed in acidified water (pH ~4).

TABLE 38

Data for the polymerization of MPEG(2000)MA with initiator 7 at 50/70° C. in 75 w/v % toluene solution.

| Sample Time/ minutes | Conversion/ % | Mn | PDi |
|---|---|---|---|
| 2880 | 92.8 | 26370 | 1.26 |

Polymerisations Using Initiator 5

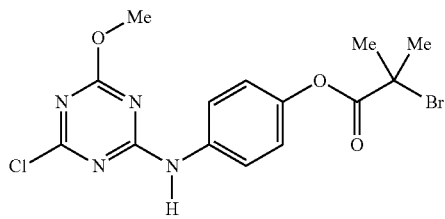

5

Polymerisation of MPEG(550)MA

[PEG]/[I]/[Cu]/[L]=64/1/in 75 w/v % Toluene Solution at 50/90° C.

Initiator 5 (0.25 g, 0.622 mmol), Cu(I)Br (0.089 g, 0.622 mmol, 1 eq) and MPEG(550)MA (24.90 g, 0.040 mol), and a magnetic follower were placed in an oven dried Schlenk tube. The Schlenk tube was evacuated and flushed with dry nitrogen three times. Deoxygenated toluene (100 mL) was added to the Schlenk tube. The resulting solution was deoxygenated by bubbling with nitrogen for 1 hour and then degassed N-ethyl-2-pyridylmethanimine (0.167 g, 1.245 mmol) was added. The reaction was placed in a thermostatically controlled oil bath at 50° C. (t=0) and samples were removed periodically for conversion and molecular weight analysis. The temperature was increased to 90° C. after 3 hours 15 minutes.

TABLE 39

Data for the polymerization of MPEG(550)MA with initiator 5 at 50/90° C. in 75 w/v % toluene solution.

| Sample Time/ minutes | Conversion/ % | Mn | PDi |
|---|---|---|---|
| 150 | 3 | 5376 | 1.07 |
| 353 | 9 | 10390 | 1.09 |
| 1750 | 27 | 13890 | 1.16 |

Polymerisation of MPEG(1000)MA

[PEG]/[I]/[Cu]/[L]=37/1/1/2 in 75 w/v % Toluene Solution at 50° C.

Initiator 5 (0.125 g, 0.031 mmol), Cu(I)Br (0.044 g, 0.031 mmol, 1 eq) and MPEG(1000)MA (12.45 g, 0.012 mol), and a magnetic follower were placed in an oven dried Schlenk tube. The Schlenk tube was evacuated and flushed with dry nitrogen three times. Deoxygenated toluene (50 mL) was added to the Schlenk tube. The resulting solution was deoxygenated by bubbling with nitrogen for 1 hour and then degassed N-ethyl-2-pyridylmethanimine (0.083 g, 0.062 mmol) was added. The reaction was placed in a thermostatically controlled oil bath at 50° C. (t=0) and samples were removed periodically for conversion and molecular weight analysis.

TABLE 40

Data for the polymerization of MPEG(1000)MA with initiator 5 at 50° C. in 75 w/v % toluene solution.

| Sample Time/ minutes | Conversion/ % | Mn | PDi |
| --- | --- | --- | --- |
| 62 | 0 | 0 | 0 |
| 352 | 10 | 9713 | 1.06 |
| 1716 | 15 | 10924 | 1.08 |
| 2725 | 16 | 11240 | 1.08 |
| 4142 | 15 | 12800 | 1.11 |

Polymerisations Using Initiator 9

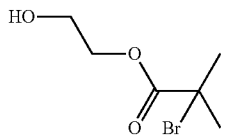

9

Polymerisation of MPEG(2000)MA

[PEG]/[I]/[Cu]/[L]=28.8:1/1/2 in 67 w/v % Acetone at 50° C.

Initiator 9 (0.035 g, 1.667×10$^{-4}$ mol), Cu(I)Br (0.024 g, 1.667×10$^{-4}$ mol) and MPEG(2000)MA (10 g, 4.81×10$^{-3}$ mol) and a magnetic follower were placed in an oven dried Schlenk tube. The Schlenk tube was evacuated and flushed with dry nitrogen three times. Acetone (20 mL) was then added to the Schlenk tube and the mixture degassed via three consecutive freeze, pump, thaw cycles. On completion deoxygenated N-ethyl-2-pyridylmethanimine (0.05 mL, 3.54×10$^{-4}$ mol) was added and the Schlenk placed in a thermostatically controlled oil bath at 50° C. (t=0) and samples removed periodically for conversion and molecular weight analysis.

TABLE 41

Data for the polymerization of MPEG(2000)MA with initiator 9 at 50° C. in 67 w/v % acetone solution

| Sample Time/ minutes | Conversion/ % | Mn | PDi |
| --- | --- | --- | --- |
| 60 | 3 | 25270 | 1.06 |
| 360 | 19 | 22690 | 1.08 |
| 3480 | 74 | 32080 | 1.14 |

Polymerisations Using Initiator 6

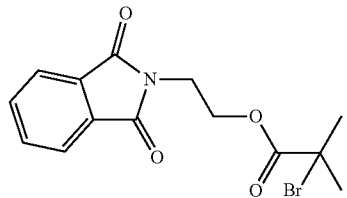

6

Polymerisation of MPEG(2000)MA

[PEG]/[I]/[Cu]/[L]=14.4/1/1/2 in 67 w/v % Toluene at 30° C.

Initiator 6 (0.119 g, 3.333×10$^{-4}$ mol), Cu(I)Br (0.048 g, 3.333×10$^{-4}$ mol) and MPEG(2000)MA (10 g, 4.81×10$^{-3}$ mol) and a magnetic follower were placed in an oven dried Schlenk tube. The Schlenk tube was evacuated and flushed with dry nitrogen three times. Toluene (20 mL) was then added to the Schlenk tube and the mixture degassed via three consecutive freeze, pump, thaw cycles. On completion deoxygenated N-n-propyl-2-pyridylmethanimine (0.10 mL, 6.667×10$^{-4}$ mol) was added and the Schlenk placed in a thermostatically controlled oil bath at 30° C. (t=0) and sampled for conversion and molecular weight analysis.

TABLE 42

Data for the polymerization of MPEG(2000)MA with initiator 6 at 30° C. in 67 w/v % toluene solution.

| Sample Time/ minutes | Conversion/ % | Mn | PDi |
| --- | --- | --- | --- |
| 3900 | 29.5 | 24120 | 1.08 |

[PEG]/[I]/[Cu]/[L]=21.63/1/1/2 in 67 w/v % Toluene at 30° C.

Initiator 6 (0.079 g, 2.222×10$^{-4}$ mol), Cu(I)Br (0.031 g, 2.222×10$^{-4}$ mol) and PEG(2000)MA (10 g, 4.81×10$^{-3}$ mol) and a magnetic follower were placed in an oven dried Schlenk tube. The Schlenk tube was evacuated and flushed with dry nitrogen three times. Toluene (20 mL) was then added to the Schlenk tube and the mixture degassed via three consecutive freeze, pump, thaw cycles. On completion deoxygenated N-n-propyl-2-pyridylmethanimine (0.066 mL, 4.444×10$^{-4}$ mol) was added and the Schlenk placed in a thermostatically controlled oil bath at 30° C. (t=0) and sampled for conversion and molecular weight analysis.

TABLE 43

Data for the polymerization of MPEG(2000)MA with initiator 6 at 30° C. in 67 w/v % toluene solution.

| Sample Time/ minutes | Conversion/ % | Mn | PDi |
| --- | --- | --- | --- |
| 6600 | 27 | 27480 | 1.10 |

[PEG]/[I]/[Cu]/[L]=28.8/1/1/2 in 67 w/v % Toluene at 30° C.

Initiator 6 (0.059 g, 1.667×10$^{-4}$ mol), Cu(I)Br (0.024 g, 1.667×10$^{-4}$ mol) and MPEG(2000)MA (10 g, 4.81×10$^{-3}$ mol) and a magnetic follower were placed in an oven dried Schlenk tube. The Schlenk tube was evacuated and flushed with dry nitrogen three times. Toluene (20 mL) was then added to the Schlenk tube and the mixture degassed via three consecutive freeze, pump, thaw cycles. On completion deoxygenated N-n-propyl-2-pyridylmethanimine (0.049 mL, $1.667 \times 10^{-4}$ mol) was added and the Schlenk placed in a thermostatically controlled oil bath at 30° C. (t=0) and sampled for conversion and molecular weight analysis.

TABLE 44

Data for the polymerization of MPEG(2000)MA with initiator 6 at 30° C. in 67 w/v % toluene solution.

| Sample Time/ minutes | Conversion/ % | Mn | PDi |
|---|---|---|---|
| 6600 | 18.3 | 25290 | 1.09 |

Polymerisations Using Initiator 10

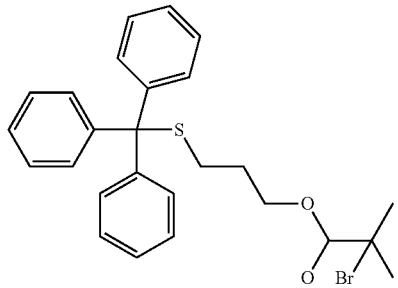

Polymerisation of MPEG(395)MA

[PEG]/[I]/[Cu]/[L]==25/1/1/2 in 67 w/v % Toluene at 50° C.

Initiator 10 (0.81 g, $1.68 \times 10^{-3}$ mol), Cu(I)Br (0.24 g, $1.68 \times 10^{-3}$ mol) and MPEG(395)MA (20.0 g, $4.21 \times 10^{-2}$ mol) and a magnetic follower were placed in an oven dried Schlenk tube. The Schlenk tube was evacuated and flushed with dry nitrogen three times. Toluene (41 mL) was then added to the Schlenk tube and the mixture deoxygenated by purging with nitrogen for 1 hour. Deoxygenated N-n-propyl-2-pyridylmethanimine (0.53 mL, $3.37 \times 10^{-3}$ mol) was then added and the Schlenk placed in a thermostatically controlled oil bath at 50° C. (t=0) and sampled for conversion and molecular weight analysis.

TABLE 45

Data for the polymerization of MPEG(395) with initiator 10 at 50° C. in 67 w/v % toluene solution.

| Sample Time/ minutes | Conversion/ % | Mn | PDi |
|---|---|---|---|
| 900 | 52.9 | 6300 | 1.11 |

Polymerisations using Initiator 11

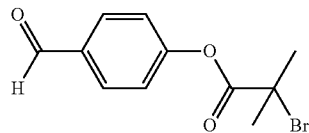

Polymerisation of MPEG(550)MA

[PEG]/[I]/[Cu]/[L]=6.4/1/1/2 in 67 v/v % Toluene Solution at 50° C.

Initiator 11 (0.103 g, 0.380 mmol), Cu(I)Br (0.054 g, 0.380 mmol, 1 eq) and MPEG(550)MA (1.51 g, 2.41 mmol), and a magnetic follower were placed in an oven dried Schlenk tube. The Schlenk tube was evacuated and flushed with dry nitrogen three times. Deoxygenated toluene (2.78 mL) was added to the Schlenk tube. The resulting solution was deoxygenated via three freeze pump thaw cycles and then degassed N-ethyl-2-pyridylmethanimine (0.10 g, 0.758 mmol) was added. The reaction was placed in a thermostatically controlled oil bath at 50° C. (t=0) and samples were removed periodically for conversion and molecular weight analysis.

TABLE 46

Data for the polymerization of MPEG(550)MA with initiator 11 at 50° C. in 67 v/v % toluene solution.

| Sample Time/ minutes | Conversion/ % | Mn | PDi |
|---|---|---|---|
| 60 | 24 | 3545 | 1.080 |
| 120 | 41 | 4002 | 1.102 |
| 180 | 53 | 4243 | 1.104 |
| 240 | 64 | 4506 | 1.109 |
| 300 | 70 | 4677 | 1.108 |

[PEG]/[I]/[Cu]/[L]=6.4/1/1/2 in 67 v/v % Toluene Solution at 50° C.

Initiator 11 (3.0 g, 11.1 mmol), Cu(I)Br (1.584 g, 11.1 mmol, 1 eq) and MPEG(550)MA (44.27 g, 70.5 mmol), and a magnetic follower were placed in an oven dried Schlenk tube. The Schlenk tube was evacuated and flushed with dry nitrogen three times. Deoxygenated toluene (81.3 mL) was added to the Schlenk tube. The resulting solution was deoxygenated by bubbling with nitrogen for 1 hour and then degassed N-ethyl-2-pyridylmethanimine (2.97 g, 22.2 mmol) was added. The reaction was placed in a thermostatically controlled oil bath at 50° C. (t=0) and samples were removed periodically for conversion and molecular weight analysis. The polymer was purified by removing the solvent in vacuo and dialysising the residue using acidic water (pH ~4). Subsequent freeze drying isolated the product.

TABLE 47

Data for the polymerization of MPEG(550)MA with initiator 11 at 50° C. in 67 v/v % toluene solution.

| Sample Time/ minutes | Conversion/ % | Mn | PDi |
|---|---|---|---|
| 60 | 27 | 4800 | 1.096 |
| 120 | 45 | 5427 | 1.115 |

TABLE 47-continued

Data for the polymerization of MPEG(550)MA with initiator 11 at 50° C. in 67 v/v % toluene solution.

| Sample Time/ minutes | Conversion/ % | Mn | PDi |
|---|---|---|---|
| 180 | 60 | 5895 | 1.127 |
| 240 | 67 | 6215 | 1.133 |
| 300 | 72 | 6343 | 1.125 |

Polymerisation of MPEG(2000)MA

[PEG]/[I]/[Cu]/[L]=12/11/2 in 80 w/v % Toluene Solution at 50/70° C.

Initiator 11 (0.1 g, 0.369 mmol), Cu(I)Br (0.053 g, 0.369 mmol, 1 eq) and MPEG(2000)MA (9.24 g, 4.44 mmol), and a magnetic follower were placed in an oven dried Schlenk tube. The Schlenk tube was evacuated and flushed with dry nitrogen three times. Deoxygenated toluene (37 mL) was added to the Schlenk tube. The resulting solution was deoxygenated by bubbling with nitrogen for 1 hour and then degassed N-ethyl-2-pyridylmethanimine (0.10 g, 0.758 mmol) was added. The reaction was placed in a thermostatically controlled oil bath at 50° C. (t=0) and samples were removed periodically for conversion and molecular weight analysis. The temperature was increased to 70° C. after 113 hours. The polymer was purified by removing the solvent in vacuo and dialysising the residue using acidic water (pH ~4). Subsequent freeze drying isolated the product.

TABLE 48

Data for the polymerization of MPEG(2000)MA with initiator 11 at 50/70° C. in 80 w/v % toluene solution.

| Sample Time/ minutes | Conversion/ % | Mn | PDi |
|---|---|---|---|
| 1020 | 21 | — | — |
| 1440 | 23 | — | — |
| 6780 | 40 | — | — |
| 9660 | 62 | 20333 | 1.117 |

[PEG]/[I]/[Cu]/[L]=24/1/1/2 in 80 w/v % Toluene Solution at 50/70° C.

Initiator 11 (0.1 g, 0.369 mmol), Cu(I)Br (0.053 g, 0.369 mmol, 1 eq) and MPEG(2000)MA (18.48 g, 8.88 mmol), and a magnetic follower were placed in an oven dried Schlenk tube. The Schlenk tube was evacuated and flushed with dry nitrogen three times. Deoxygenated toluene (74 mL) was added to the Schlenk tube. The resulting solution was deoxygenated by bubbling with nitrogen for 1 hour and then degassed N-ethyl-2-pyridylmethanimine (0.10 g, 0.758 mmol) was added. The reaction was placed in a thermostatically controlled oil bath at 50° C. (t=0) and samples were removed periodically for conversion and molecular weight analysis. The temperature was increased to 70° C. after 113 hours. The polymer was purified by removing the solvent in vacuo and dialysising the residue using acidic water (pH ~4). Subsequent freeze drying isolated the product.

TABLE 49

Data for the polymerization of MPEG(2000)MA with initiator 11 at 50/70° C. in 80 w/v % toluene solution.

| Sample Time/ minutes | Conversion/ % | Mn | PDi |
|---|---|---|---|
| 1020 | 16 | — | — |
| 2580 | 19 | — | — |
| 6780 | 22 | — | — |
| 8220 | 53 | — | — |
| 9660 | 0.57 | 22262 | 1.140 |

Polymerisations Using Initiator 12

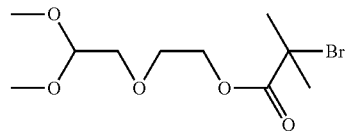

12

Polymerisation of MPEG(1000)MA

[PEG]/[I]/[Cu]/[L]=5/1/1/2 in 66 v/v % Toluene Solution at 70° C.

N-(ethyl)-2-pyridylmethanimine ligand (1.41 mL, 10.92 mmol), initiator 12 (1.633 g, 5.46 mmol), and MPEG(1000)MA (27.3 mL, 30 g, 27.3 mmol) were charged to a dry Schlenk tube along with toluene (60 mL) as the solvent and mesitylene (1 mL) as an internal standard. The tube was sealed with a rubber septum and subjected to three freeze pump thaw cycles. This solution was then cannulated under nitrogen into another Schlenk tube, previously evacuated and filled with nitrogen, containing Cu(I)Cl (0.543 g, 5.46 mmol) and a magnetic follower. The brown solution was subsequently heated to 70° C. with constant stirring (t=0). Samples were removed periodically using a degassed syringe for molecular weight and conversion analysis. After 48 h the mixture was diluted with 50 mL of toluene, air was bubbled for 6 h and the green suspension was kept at 0° C. overnight. After filtration through a short neutral alumina column to remove the copper salt, the polymer was precipitated from diethyl ether. The polymer was collected by filtration and dried in vacuum oven (40° C.) overnight.

TABLE 50

Data for the polymerization of MPEG(1000)MA with initiator 12 at 70° C. in 66 v/v % toluene solution.

| Sample Time/ hours | Conversion/ % | Mn | PDi |
|---|---|---|---|
| 1 | 17.8 | 1370 | 1.23 |
| 2.5 | 56.6 | 10700 | 1.09 |
| 4 | 73.5 | 11600 | 1.15 |
| 5 | 78.9 | 11600 | 1.11 |
| 6 | 81.3 | 11600 | 1.19 |
| 7 | 85.9 | 12600 | 1.15 |

[PEG]/[I]/[Cu]/[L]=20/1/1/2 in 66 v/v % Toluene Solution at 50° C.

N-(ethyl)-2-pyridylmethanimine ligand (0.35 mL, 2.73 mmol), initiator 12 (0.41 g, 1.37 mmol), PEG(1000)MA (27.3 mL, 30 g, 27.3 mmol) were charged to a dry Schlenk tube along with toluene (60 mL) as the solvent and mesitylene (1 mL) as internal standard. The tube was sealed with a rubber septum and subjected to three freeze pump thaw cycles. This solution was then cannulated under nitrogen into another Schlenk tube, previously evacuated and filled with nitrogen, containing Cu(I)Br (0.197 g, 1.37 mmol) and a magnetic follower. The brown solution was subsequently heated to 50° C. with constant stirring (t=0). Samples were removed periodically using a degassed syringe for molecular weight and conversion analysis. Half the reaction solution was removed with a dry cannula when conversion was at 66%, bubbled for 6 h with air, and passed over a short neutral alumina column to removed copper salt. The solvent was removed under vacuum and the unreacted monomer was removed by dialysis to give the polymer as a white powder. After 48 h the remaining reaction mixture was diluted with 50 mL of toluene, air was bubbled for 6 h and the green suspension was kept at 0° C. overnight. After filtration through a short neutral alumina column to remove the copper salt, the polymer was precipitated from diethyl ether. The polymer was collected by filtration and dried in vacuum oven (40° C.) overnight.

TABLE 51

Data for the polymerization of MPEG(1000)MA with initiator 12 at 50° C. in 66 v/v % toluene solution.

| Sample Time/ hours | Conversion/ % | Mn | PDi |
|---|---|---|---|
| 1 | 5 | 1566 | 1.14 |
| 3 | 11 | 11400 | 1.06 |
| 6 | 26 | 13000 | 1.07 |
| 8 | 31 | 12700 | 1.09 |
| 21 | 61 | 13600 | 1.13 |
| 24 | 66 | 13800 | 1.14 |
| 28 | 73 | 14500 | 1.2 |
| 31 | 76 | 14900 | 1.21 |
| 46 | 87 | 14600 | 1.18 |
| 50.5 | 89 | 16000 | 1.2 |
| 54 | 0.9 | 17600 | 1.19 |

Polymerisations Using Initiator 13

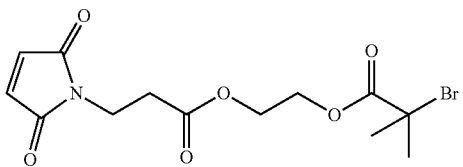

13

Polymerisation of MPEG(550)MA

[PEG]/[I]/[Cu]/[L]=15.9/1/1/2 in 67 w/v % Toluene Solution at 30° C.

Initiator 13 (0.10 g, 0.28 mmol), Cu(I)Br (0.039 g, 0.28 mmol, 1 eq) and MPEG(550)MA (2.76 g, 4.39 mmol), and a magnetic follower were placed in an oven dried Schlenk tube. The Schlenk tube was evacuated and flushed with dry nitrogen three times. Deoxygenated toluene (5.5 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 30° C. (t=0) and samples were removed periodically for conversion and molecular weight analysis.

TABLE 52

Data for the polymerization of MPEG(550)MA with initiator 13 at 30° C. in 67 w/v % toluene solution.

| Sample Time/ minutes | Conversion/ % | Mn | PDi |
|---|---|---|---|
| 1440 | 7.8 | 5626 | 1.08 |
| 4260 | 14.0 | 6153 | 1.11 |

[PEG]/[I]/[Cu]/[L]=8/1/1/2 in 67 w/v % Toluene Solution at 50° C.

Initiator 13 (0.10 g, 0.28 mmol), Cu(I)Br (0.039 g, 0.28 mmol, 1 eq) and MPEG(550)MA (1.38 g, 2.20 mmol), and a magnetic follower were placed in an oven dried Schlenk tube. The Schlenk tube was evacuated and flushed with dry nitrogen three times. Deoxygenated toluene (2.75 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 50° C. (t=0) and samples were removed periodically for conversion and molecular weight analysis.

TABLE 53

Data for the polymerization of MPEG(550)MA with initiator 13 at 50° C. in 67 w/v % toluene solution.

| Sample Time/ minutes | Conversion/ % | Mn | PDi |
|---|---|---|---|
| 7200 | 44.8 | 7880 | 1.16 |

[PEG]/[I]/[Cu]/[L]=15.9/1/1/2 in 67 w/v % Toluene Solution at 50° C.

Initiator 13 (0.10 g, 0.28 mmol), Cu(I)Br (0.039 g, 0.28 mmol, 1 eq) and MPEG(550)MA (2.76 g, 4.39 mmol), and a magnetic follower were placed in an oven dried Schlenk tube. The Schlenk tube was evacuated and flushed with dry nitrogen three times. Deoxygenated toluene (5.5 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 50° C. (t=0) and samples were removed periodically for conversion and molecular weight analysis.

TABLE 54

Data for the polymerization of MPEG(550)MA with initiator 13 at 50° C. in 67 w/v % toluene solution.

| Sample Time/ minutes | Conversion/ % | Mn | PDi |
|---|---|---|---|
| 1440 | 16.4 | 7971 | 1.12 |
| 8640 | 27.2 | 8378 | 1.14 |

[PEG]/[I]/[Cu]/[L]=31.8/1/1/2 in 67 w/v % Toluene Solution at 50° C.

Initiator 13 (0.10 g, 0.28 mmol), Cu(I)Br (0.039 g, 0.28 mmol, 1 eq) and MPEG(550)MA (5.51 g, 8.77 mmol), and a magnetic follower were placed in an oven dried Schlenk tube. The Schlenk tube was evacuated and flushed with dry nitrogen three times. Deoxygenated toluene (11.0 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 50° C. (t=0) and samples were removed periodically for conversion and molecular weight analysis.

TABLE 55

Data for the polymerization of MPEG(550)MA with initiator 13 at 50° C. in 67 w/v % toluene solution.

| Sample Time/ minutes | Conversion/ % | Mn | PDi |
|---|---|---|---|
| 1440 | 9.6 | 8504 | 1.11 |
| 5760 | 16.8 | 9999 | 1.14 |
| 8640 | 17.8 | 10208 | 1.13 |

[PEG]/[I]/[Cu]/[L]=15.9/1/1/2 in 67 w/v % Toluene Solution at 70° C.

Initiator 13 (0.10 g, 0.28 mmol), Cu(I)Br (0.039 g, 0.28 mmol, 1 eq) and MPEG(550)MA (2.76 g, 4.39 mmol), and a magnetic follower were placed in an oven dried Schlenk tube. The Schlenk tube was evacuated and flushed with dry nitrogen three times. Deoxygenated toluene (5.5 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 70° C. (t=0) and samples were removed periodically for conversion and molecular weight analysis.

TABLE 56

Data for the polymerization of MPEG(550)MA with initiator 13 at 70° C. in 67 w/v % toluene solution.

| Sample Time/ minutes | Conversion/ % | Mn | PDi |
|---|---|---|---|
| 120 | 13.6 | 5768 | 1.09 |
| 300 | 21.3 | 6814 | 1.10 |
| 4260 | 41.0 | 8444 | 1.15 |

[PEG]/[I]/[Cu]/[L]=15.9/1/1/2 in 67 w/v % Toluene Solution at 50/90° C.

Initiator 13 (0.10 g, 0.28 mmol), Cu(I)Cl (0.0273 g, 0.28 mmol, 1 eq) and MPEG(550)MA (2.76 g, 4.39 mmol), and a magnetic follower were placed in an oven dried Schlenk tube. The Schlenk tube was evacuated and flushed with dry nitrogen three times. Deoxygenated toluene (5.5 mL) was added to the Schlenk tube. The resulting solution was deoxygenated via three freeze pump thaw cycles and then degassed N-ethyl-2-pyridylmethanimine (0.074 g, 0.56 mmol) was added. The reaction was placed in a thermostatically controlled oil bath at 50° C. (t=0) and samples were removed periodically for conversion and molecular weight analysis. The temperature was increased to 90° C. after 163 hours

TABLE 57

Data for the polymerization of MPEG(550)MA with initiator 13 at 50/90° C. in 67 w/v % toluene solution.

| Sample Time/ minutes | Conversion/ % | Mn | PDi |
|---|---|---|---|
| 9780 | 3.8 | 4090 | 1.09 |
| 12660 | 81.0 | 16504 | 1.31 |

Polymerisations Using Initiator 14

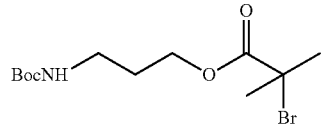

14

Polymerisation of MPEG(395)MA

[PEG]/[I]/[Cu]/[L]=6/1/1/2 in 50 v/v % Toluene Solution at 40° C.

N-(ethyl)-2-pyridylmethanimine ligand (1.07 mL, 1.017 g, $7.58 \times 10^{-3}$ mol), initiator 14 (1.229 g, $3.79 \times 10^{-3}$ mol) and MPEG(395)MA (10.80 g, $22.70 \times 10^{-3}$ mol) were charged to a dry Schlenk tube along with toluene (10 mL) as the solvent (50% v/v). The tube was sealed with a rubber septum and subjected to three freeze-pump-thaw cycles. This solution was then cannulated under nitrogen into another Schlenk tube, previously evacuated and filled with nitrogen, containing Cu(I)Br (0.544 g, $3.79 \times 10^{-3}$ mol) and a magnetic follower. The brown solution was subsequently heated to 40° C. with constant stirring (t=0). Samples were removed periodically using a degassed syringe for molecular weight and conversion analysis. After 48 h the mixture was diluted with 50 mL of toluene, air was bubbled for 6 h and the green suspension was kept at 0° C. overnight. After filtration through a Celite® pad, the solvent was removed under reduced pressure to give a yellow-brown oil which was dissolved in water (250 mL) and purified by dialysis (Millipore, regenerated cellulose, MWCO 1 kDa, filtration area 0.23 m$^2$) to give the expected polymer as a pale yellow oil.

TABLE 58

Polymerisation data for TMM-LRP of MPEG(395)MA using initiator 14, [monomer]:[initiator]:[CuBr]:[L] = 6:1:1:2.

| Monomer/ Initiator | Time (mins) | Conv. (%) | ln([M]$_0$/[M]) | M$_n$ | PDI |
|---|---|---|---|---|---|
| 6:1 (40° C.) | 60 | 34.76 | 0.478 | 5876 | 1.03 |
| | 120 | 49.43 | 0.667 | 7250 | 1.08 |
| | 180 | 62.05 | 0.889 | 8089 | 1.08 |
| | 240 | 71.54 | 1.118 | 9013 | 1.10 |
| | 300 | 76.33 | 1.359 | 9262 | 1.10 |
| | 360 | 80.18 | 1.556 | 9561 | 1.07 |
| | 420 | 86.93 | 1.904 | 9932 | 1.10 |
| | 480 | 88.72 | 2.216 | 10195 | 1.10 |

[PEG]/[I]/[Cu]/[L]=28/1/1/2 in 50 v/v % Toluene Solution at 40° C.

N-(ethyl)-2-pyridylmethanimine ligand (1.07 mL, 1.017 g, $7.58 \times 10^{-3}$ mol), initiator 14 (0.263 g, $0.812 \times 10^{-3}$ mol) and MPEG(395)MA (10.80 g, $22.70 \times 10^{-3}$ mol) were charged to a dry Schlenk tube along with toluene (10 mL) as the solvent (50% v/v). The tube was sealed with a rubber septum and subjected to three freeze-pump-thaw cycles. This solution was then cannulated under nitrogen into another Schlenk tube, previously evacuated and filled with nitrogen, containing Cu(I)Br (0.116 g, $0.812 \times 10^{-3}$ mol) and a magnetic follower. The brown solution was subsequently heated to 40° C. with constant stirring (t=0). Samples were removed periodically using a degassed syringe for molecular weight and conversion analysis. After 48 h the mixture was diluted with 50 mL of toluene, air was bubbled for 6 h and the green suspension was kept at 0° C. overnight. After filtration through a Celite® pad, the solvent was removed under reduced pressure to give a yellow-brown oil which was dissolved in water (250 mL) and purified by dialysis (Millipore, regenerated cellulose, MWCO 1 kDa, filtration area 0.23 m²) to give the expected polymer as a pale yellow oil.

TABLE 59

Polymerisation data for TMM-LRP of MPEG(395)MA using initiator 14, [monomer]:[initiator]:[CuBr]:[L] = 28:1:1:2. T = 40° C.

| Monomer/ Initiator | Time (mins) | Conv. (%) | ln([M]$_0$/[M]) | M$_n$ | PDI |
|---|---|---|---|---|---|
| 28:1 (40° C.) | 60 | 21.8 | 0.246 | 5500 | 1.05 |
| | 120 | 24.7 | 0.284 | 5798 | 1.06 |
| | 180 | 37.4 | 0.468 | 7001 | 1.09 |
| | 240 | 41.5 | 0.536 | 7202 | 1.08 |
| | 300 | 46.2 | 0.620 | 7633 | 1.07 |
| | 360 | 49.3 | 0.680 | 7733 | 1.09 |
| | 420 | 50.7 | 0.707 | 7899 | 1.09 |
| | 480 | 55.4 | 0.808 | 8099 | 1.08 |

[PEG]/[I]/[Cu]/[L]=28/1/1/2 in 50 v/v % Toluene Solution at 60° C.

N-(ethyl)-2-pyridylmethanimine ligand (1.07 mL, 1.02 g, 7.58×10⁻³ mol), initiator 14 (0.263 g, 0.812×10⁻³ mol) and MPEG(395)MA (10.80 g, 22.70×10⁻³ mol) were charged to a dry Schlenk tube along with toluene (10 mL) as the solvent (50% v/v). The tube was sealed with a rubber septum and subjected to three freeze-pump-thaw cycles. This solution was then cannulated under nitrogen into another Schlenk tube, previously evacuated and filled with nitrogen, containing Cu(I)Br (0.116 g, 0.812×10⁻³ mol) and a magnetic follower. The brown solution was subsequently heated to 60° C. with constant stirring (t=0). Samples were removed periodically using a degassed syringe for molecular weight and conversion analysis. After 48 h the mixture was diluted with 50 mL of toluene, air was bubbled for 6 h and the green suspension was kept at 0° C. overnight. After filtration through a Celite® pad, the solvent was removed under reduced pressure to give a yellow-brown oil which was dissolved in water (250 mL) and purified by dialysis (Millipore, regenerated cellulose, MWCO 1 kDa, filtration area 0.23 m²) to give the expected polymer as a pale yellow oil.

TABLE 60

Polymerisation data for TMM-LRP of MPEG(395)MA using initiator 14, [monomer]:[initiator]:[CuBr]:[L] = 28:1:1:2. T = 60° C.

| Monomer/ Initiator | Time (mins) | Conv. (%) | ln([M]$_0$/[M]) | M$_n$ | PDI |
|---|---|---|---|---|---|
| 28:1 (60° C.) | 60 | 38.0 | 0.427 | 5233 | 1.06 |
| | 120 | 48.7 | 0.682 | 5656 | 1.07 |
| | 180 | 58.9 | 0.969 | 6116 | 1.06 |
| | 240 | 67.3 | 1.257 | 6185 | 1.08 |
| | 300 | 74.3 | 1.441 | 6416 | 1.07 |
| | 360 | 78.9 | 1.618 | 6284 | 1.08 |
| | 420 | 85.1 | 2.035 | 6291 | 1.08 |
| | 480 | 89.1 | 2.182 | 6610 | 1.08 |

[PEG]/[I]/[Cu]/[L]=10/1/1/2 in 50 v/v % d$_8$-Toluene Solution at 40° C.

N-(n-octyl)-2-pyridylmethanimine ligand (0.052 mL, 0.050 g, 0.228×10⁻³ mol), initiator 14 (0.037 g, 0.114×10⁻³ mol) and MPEG(395)MA (0.050 mL, 0.540 g, 1.14×10⁻³ mol) were charged to a dry Schlenk tube along with d$_8$-toluene (0.50 mL) as the solvent (50% v/v). The tube was sealed with a rubber septum and subjected to three freeze-pump-thaw cycles. This solution was then cannulated under nitrogen into an NMR tube, previously evacuated and filled with nitrogen, containing Cu(I)Br (0.016 g, 0.114×10⁻³ mol). The tube was then heated to 40° C. and ¹H NMR spectra were recorded every 15 minutes.

Polymerisations Using Initiator 15

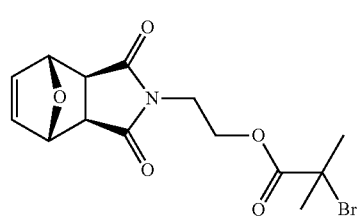

15

Polymerisation of MPEG(395)MA

[PEG]/[I]/[Cu]/[L]=8/1/1/2 in 50 wv % Toluene Solution at 30° C.

N-(ethyl)-2-pyridylmethanimine ligand (0.80 mL, 0.76 g, 5.68×10⁻³ mol), initiator 15 (2.03 g, 5.68×10⁻³ mol) MPEG (395)MA (20.0 mL, 21.6 g, 45.50×10⁻³ mol) were charged to a dry Schlenk tube along with toluene (20 mL) as the solvent (50% v/v). The tube was sealed with a rubber septum and subjected to three freeze-pump-thaw cycles. This solution was then cannulated under nitrogen into another Schlenk tube, previously evacuated and filled with nitrogen, containing Cu(I)Br (0.41 g, 2.84×10⁻³ mol) and a magnetic follower (t=0). The brown solution was subsequently stirred at 30° C. Samples were removed periodically using a degassed syringe for molecular weight and conversion analysis. After 7 h the mixture was diluted with 50 mL of toluene, air was bubbled for 6 h and the green suspension was kept at 0° C. overnight. After filtration through a Celite® pad, the solvent was removed under reduced pressure to give a yellow-brown oil which was dissolved in water (250 mL) and purified by dialysis (Millipore, regenerated cellulose, MWCO I kDa, filtration area 0.23 m²) to give the expected polymer as a pale yellow oil.

TABLE 61

Polymerisation data for TMM-LRP of MPEG(395)MA using initiator 15, [monomer]:[initiator]:[CuBr]:[L] = 8:1:1:2. T = 30° C.

| Monomer/ Initiator | Time (mins) | Conv. (%) | ln([M]$_0$/[M]) | M$_n$ | PDI |
|---|---|---|---|---|---|
| 8:1 (30° C.) | 60 | 22.90 | 0.478 | 4532 | 1.07 |
| | 120 | 34.64 | 0.667 | 5008 | 1.11 |
| | 180 | 45.66 | 0.889 | 5379 | 1.11 |
| | 246 | 50.97 | 1.118 | 5662 | 1.09 |
| | 420 | 67.14 | 1.359 | 6165 | 1.08 |

Reactions of PolyPEG Polymers

Reactions of PolyPEG Polymers Prepared from Initiator 8

Hydrolytic Stability of the Succinimide End Group of PolyPEG Polymer Initiated by 8

On-line ¹H NMR experiments was carried out, each using a different buffer. N-succinimidyl (initiator 8) terminated poly(MPEG(395)MA (Mn=6400 g/mol, PDI=1.09) (50 mg, 0.00781×10$^{-3}$ mol) were introduced in an NMR tube and dissolved in 0.5 mL of the appropriate phosphate buffer (pH=8, C=100 mM or 200 mM). NMR spectra were recorded regularly.

TABLE 62

Kinetic data for the hydrolysis of N-succinimidyl terminated poly(MPEG(395)MA initiated by 8 in different buffers.

| 100 mM phosphate buffer (pH = 8) | | 200 mM phosphate buffer (pH = 8) | |
|---|---|---|---|
| Time (h) | Conversion (%) | Time (h) | Conversion (%) |
| 0 | 0 | 0 | 0 |
| 0.5 | 4.8 | 0.5 | 8.6 |
| 1 | 9.5 | 1 | 13.5 |
| 1.5 | 10.1 | 1.5 | 17.5 |
| 2 | 15.8 | 2 | 19.8 |
| 2.5 | 14.2 | 2.5 | 22.7 |
| 3 | 15.1 | 3 | 25.5 |
| 3.5 | 18.5 | 3.5 | 26.7 |
| 4 | 22.4 | 4 | 28.9 |
| 4.5 | 23.2 | 4.5 | 33.7 |
| 5 | 26.0 | 5 | 33.2 |
| 5.5 | 30.1 | 5.5 | 37.1 |
| 6 | 28.7 | 6 | 38.9 |
| 6.5 | 30.7 | 6.5 | 39.6 |
| 7 | 30.7 | 7 | 44.1 |
| 7.5 | 30.1 | 7.5 | 43.0 |
| 8 | 37.3 | 8 | 44.0 |
| 8.5 | 35.9 | 8.5 | 45.2 |
| 9 | 36.7 | 9 | 45.8 |
| 9.5 | 40.7 | 9.5 | 46.5 |
| 10 | 45.2 | 10 | 50.6 |
| 10.5 | 40.8 | 10.5 | 49.7 |
| 11 | 43.2 | 11 | 52.2 |
| 11.5 | 42.5 | 11.5 | 52.5 |
| 12 | 44.8 | 12 | 55.6 |
| 12.5 | 45.4 | 12.5 | 55.5 |
| 13 | 45.1 | 13 | 56.9 |
| 13.5 | 45.0 | 13.5 | 53.7 |
| 14.5 | 48.9 | | |
| 15 | 48.4 | | |
| 15.5 | 50.1 | | |
| 16 | 49.6 | | |
| 16.5 | 50.1 | | |
| 17 | 52.6 | | |
| 17.5 | 50.2 | | |
| 18 | 53.2 | | |
| 18.5 | 52.0 | | |
| 19 | 54.9 | | |
| 19.5 | 55.1 | | |
| 20 | 53.9 | | |
| 20.5 | 55.5 | | |
| 21 | 55.9 | | |
| 21.5 | 53.0 | | |
| 22 | 54.5 | | |
| 22.5 | 55.9 | | |
| 23 | 55.3 | | |
| 23.5 | 57.6 | | |
| 24 | 58.9 | | |

Bioconjuction of Succinimide Terminated PolyPEG Polymer Initiated by 8

A set of three experiments was carried out, each containing a different ratio polymer/lysozyme. Low molecular weight succinimidyl ester terminated poly(MPEG(395)MA) prepared from initiator 8 (Mn=6400 g/mol, PDI=1.11) (8.9 mg, 1.39×10$^{-6}$ mol) for a ratio 2/1, (22.6 mg, 3.50×10$^{-6}$ mol) for a ratio 5/1 and (89.5 mg, 13.99×10$^{-6}$ mol) for a ratio 20/1 and lysozyme (10 mg, 0.699×10$^{-6}$ mol) was dissolved in 10 ml of anhydrous DMSO and 0.5 mL of anhydrous TEA and stirred at room temperature under nitrogen. Samples were taken periodically and analyzed by HPLC. The HPLC system was fitted with a guard column, a BioSep-SEC-S3000 column and a UV detector continuously measuring the relative absorbance of the mobile phase at 215 nm. The system was eluted with 0.1% v/v trifluoroacetic acid solution in water and acetonitrile (69/31 v/v) at a rate of 0.5 mL/min. In the case of a ratio 30:1, the crude was analysed by SDS-PAGE (polyacrylamide resolving gel cross-linking: 15%, running buffer. 25 mM TRIS base, 250 mM glycine, 0.1% SDS, pH 8.7).

Reactions of PolyPEG Polymers Prepared from Initiator 7

Hydrolytic Stability of the Succinimide End Group of PolyPEG Polymer Initialed by 7

On-line 1H NMR experiments was carried out, each using a different buffer. N-succinimidyl (initiator 7) terminated Poly(MPEG(395)MA (Mn=2700 g/mol, PDI=1.12) (50 mg, 0.0185×10-3 mol) were introduced in an NMR tube and dissolved in 0.5 mL of the appropriate buffer (200 mM phosphate buffer (pH=6 and pH=8), 100 mM phosphate buffer (pH=8) or 200 mM borate buffer (pH=9.2)). NMR spectra were recorded regularly.

TABLE 63

Kinetic data for the hydrolysis of the succinimide end group of Poly(MPEG(395)MA polymer initiated by 7 in different buffers.

| 200 mM phosphate buffer (pH = 6) | | 100 mM phosphate buffer (pH = 8) | | 200 mM phosphate buffer (pH = 8) | | 200 mM borate buffer (pH = 9.2) | |
|---|---|---|---|---|---|---|---|
| Time (h) | Conversion (%) | Time (h) | Conversion (%) | Time (h) | Conversion (%) | Time (h) | Conversion (%) |
| 0.03 | 5.0 | 0.5 | 2.5 | 0.5 | 3 | 48 | 0.8 |
| 0.067 | 15.0 | 1 | 4.8 | 1 | 5.48 | 192 | 3 |
| 0.10 | 25.0 | 1.5 | 6.4 | 1.5 | 7.6 | 336 | 5.2 |
| 0.13 | 35.0 | 2 | 9.1 | 2 | 9.13 | 504 | 9.6 |
| 0.17 | 43.8 | 2.5 | 10.2 | 3 | 11.56 | | |
| 0.20 | 48.5 | 3 | 11.2 | 4 | 14.33 | | |
| 0.23 | 55.0 | 3.5 | 12.4 | 5 | 16.5 | | |
| 0.27 | 60.0 | 4 | 14.1 | 21 | 31.7 | | |
| 0.30 | 64.0 | 4.5 | 16.1 | 22 | 31.32 | | |
| 0.33 | 66.0 | 5 | 17.4 | 23 | 33.86 | | |
| 0.37 | 69.0 | 5.5 | 19.6 | 24 | 34.04 | | |
| 0.40 | 70.0 | 6 | 20.6 | 25 | 33.35 | | |
| 0.43 | 72.0 | 6.5 | 24 | 39 | 42.73 | | |
| 0.47 | 73.0 | 7 | 26.2 | 57 | 49.2 | | |
| 0.50 | 74.5 | 7.5 | 26.9 | 77 | 54.11 | | |
| 0.67 | 81.4 | 8 | 27.7 | 99 | 57.3 | | |
| 0.83 | 87.2 | 8.5 | 29.4 | 125 | 63 | | |
| 1.00 | 92.9 | 9 | 28.9 | 146 | 65.24 | | |
| 1.17 | 96.7 | 9.5 | 30 | 171 | 67.35 | | |
| 1.33 | 100 | 10 | 32.7 | 195 | 69.7 | | |
| | | 12.5 | 35.7 | 220 | 72.22 | | |
| | | 15 | 38.9 | 257 | 75 | | |
| | | 17.5 | 41.9 | 270 | 75.47 | | |
| | | 20 | 46 | 299 | 78.07 | | |
| | | 22.5 | 49 | | | | |
| | | 25 | 50.7 | | | | |
| | | 27.5 | 53.4 | | | | |
| | | 30 | 54.4 | | | | |
| | | 32.5 | 57.6 | | | | |
| | | 35 | 59 | | | | |
| | | 37.5 | 61.6 | | | | |
| | | 40 | 62.9 | | | | |
| | | 42.5 | 65.1 | | | | |
| | | 45 | 66.3 | | | | |
| | | 47.5 | 68.4 | | | | |

TABLE 63-continued

Kinetic data for the hydrolysis of the succinimide end group of Poly(MPEG(395)MA) polymer initiated by 7 in different buffers.

| 200 mM phosphate buffer (pH = 6) | | 100 mM phosphate buffer (pH = 8) | | 200 mM phosphate buffer (pH = 8) | | 200 mM borate buffer (pH = 9.2) | |
|---|---|---|---|---|---|---|---|
| Time (h) | Conversion (%) | Time (h) | Conversion (%) | Time (h) | Conversion (%) | Time (h) | Conversion (%) |
| | | 50 | 69.1 | | | | |
| | | 52.5 | 70 | | | | |
| | | 55 | 72 | | | | |
| | | 59.5 | 73.3 | | | | |

Conversion of Succinimide End Group of PolyPEG to Amine Group

Ethylenediamine (22.4 mL, 0.333 mol) and a magnetic follower were placed into a three necked round bottom flask fitted with a pressure equalising dropping funnel. The system was flushed with nitrogen and placed under positive pressure. A solution of succinimide terminated poly(MPEG(50)MA) [Mn 4590 PDi 1.22](3.0 g, 9.38×10$^{-4}$ mol) dissolved in anhydrous dichloromethane (12 mL) was added to the dropping funnel and the solution added drop-wise to the ethylenediamine. The solution was left stirring for 16 hours before dialysing and subsequently freeze drying to isolate the product. $^1$H NMR spectra shows the reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (14.85 mL, 0.222 mol) and a magnetic follower were placed into a three necked round bottom flask fitted with a pressure equalising dropping funnel. The system was flushed with nitrogen and placed under positive pressure. A solution of succinimide terminated poly(MPEG(550)MA) [Mn 4590 PDi 1.22](2.0 g, 6.25×10$^{-4}$ mol) dissolved in water (20 mL) was added to the dropping funnel and the solution added drop-wise to the ethylenediamine. The solution was left stirring for 16 hours before dialysing and subsequently freeze drying to isolate the product. $^1$H NMR spectra shows reduction of the succinimide O=C—C$\underline{H}_2$—CH$_2$—C=O resonance at 2.75 ppm.

Conversion of Succinimide End Group of PolyPEG to Amine Group

Ethylenediamine (20.0 mL, 0.299 mol), water (20 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(550)MA) [Mn 4590 PDi 1.22](5.0 g, 1.56×10$^{-3}$ mol) dissolved in water (50 mL) was added to the dropping funnel and the solution added drop-wise to the ethylenediamine. The solution was left stirring for 24 hours before dialysing and subsequently freeze drying to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (1.35 mL, 0.02 mol), water (5 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(550)MA) [Mn 4590 PDi 1.22](1.0 g, 3.13×10$^{-4}$ mol) dissolved in water (25 mL) was added to the dropping funnel and the solution added drop-wise to the ethylenediamine. The solution was left stirring for 3 hours before adding the solution to 2 L of water and dialysing. Subsequently the dialysed solution was freeze dried to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (1.35 mL, 0.02 mol), anhydrous dichloromethane (5 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(550)MA) [Mn 4590 PDi 1.22](1.0 g. 3.13×10$^{-4}$ mol) dissolved in anhydrous dichloromethane (25 mL) was added to the dropping funnel and the solution added drop-wise to the ethylenediamine. The solution was left stirring for 3 hours before adding the solution to 2 L of water and dialysing. Subsequently the dialysed solution was freeze dried to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (2.68 mL, 0.04 mol), water (10 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(550)MA) [Mn 4590 PDi 1.22](2.0 g, 6.25×10$^{-4}$ mol) dissolved in water (50 mL) was added to the dropping funnel and the solution added drop-wise to the ethylenediamine. The solution was left stirring for 5.5 hours before adding the solution to 2 L of water and dialysing. Subsequently the dialysed solution was freeze dried to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (2.67 mL, 0.04 mol), water (10 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(550)MA) [Mn 4590 PDi 1.22] (2.0 g, 6.25×10$^{-4}$ mol) dissolved in water (50 mL) was added to the dropping funnel and the solution added drop-wise to the ethylenediamine. The solution was stirred for 4 hours before neutralising the solution with 2M HCl and the water subsequently removed using high vacuum. The polymer was dialysed and then freeze dried to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (0.836 mL, 0.013 mol), water (1 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(2000) MA) [Mn 24600 PDi 1.06](5.0 g, 2.03×10$^{-4}$ mol) dissolved in water (100 mL) was added to the dropping funnel and the solution added drop-wise to the ethylenediamine. The solution was stirred for 4 hours before neutralising the solution with 2M HCl and the water subsequently removed using high vacuum. The polymer was dialysed and then freeze dried to isolate the product $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (2.5 mL, 0.038 mol), water (10 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(2000) MA) [Mn 24600 PDi 1.06](15.0 g, 7.5×10$^{-4}$ mol) dissolved in water (400 mL) was added to the dropping funnel and the solution added drop-wise to the ethylenediamine. The solution was stirred for 4 hours before neutralising the solution with 2M HCl then adding NaCl (140 g) before extracting into dichloromethane (4×150 mL). The organic layers were combined and dried over Na$_2$SO$_4$ filtered and then evaporated to dryness before being washed with diethyl ether. The polymer was dialysed and then freeze dried to isolate the product. $^1$H NMR spectra shows reduction of the succinimide O=C—C$\underline{H}_2$—C$\underline{H}_2$—C=O resonance at 2.75 ppm.

Conversion of Succinimide End Group of PolyPEG to Amine Group

Ethylenediamine (5.60 mL, 0.08 mol), water (10 mL) and a magnetic follower were placed into a three necked round bottom flask fitted with a pressure equalising dropping funnel and the solution cooled by placing in an ice bath. The system was flushed with nitrogen and placed under positive pressure. A solution of succinimide terminated poly(MPEG(2000) MA) [Mn 21900 PDi 1.21](33.5 g, 1.53×10$^{-3}$ mol) dissolved in water (500 mL) was added to the dropping funnel and the solution added drop-wise to the ethylenediamine. The solution was stirred for 4 hours before neutralising the solution with 2M HCl then adding NaCl (140 g) before extracting into dichloromethane (4×150 mL). The organic layers were combined and dried over Na$_2$SO$_4$ filtered and then evaporated to dryness before being washed with diethyl ether. The polymer was dialysed and then freeze dried to isolate the product. $^1$H NMR spectra shows reduction of the succinimide O=C—C$\underline{H}_2$—C$\underline{H}_2$—C=O resonance at 2.75 ppm.

Conversion of Amine End Group of PolyPEG to Maleimide Group

Amine terminated poly(MPEG(550)MA) [Mn 3200](0.5 g, 1.56×10$^{-4}$ mol), saturated sodium hydrogen carbonate (2.5 mL) and a magnetic follower were placed into a three necked round bottom flask and cooled by placing in an ice bath. The system was flushed with nitrogen and placed under an inert atmosphere. To this solution N-methoxycarbonylmaleimide (0.1 g, 6.45×10$^{-4}$ mol) was added with vigorous stirring. After ten minutes water (5 mL) was added and the reaction left stirring for a further 45 minutes. The pH was then adjusted to 3 with 0.5N sulfuric acid and NaCl (0.15 g) was added. The polymer was then extracted in to dichloromethane (3×50 mL), the extracts were combined and dried over Na$_2$SO4 before being filtered and evaporated to dryness. The polymer was then washed with diethyl ether and dried under vacuum at room temperature. $^1$H NMR spectra shows appearance of the maleimide resonances at ~5.9-6.4 and ~6.7 ppm.

Conversion of Amine End Group of PolyPEG to Maleimide Group

Amine terminated poly(MPEG(550)MA) [Mn 3200](1.0 g, 3.13×10$^{-4}$ mol), saturated sodium hydrogen carbonate (5 mL) and a magnetic follower were placed into a three necked round bottom flask and cooled by placing in an ice bath. The system was flushed with nitrogen and placed under an inert atmosphere. To this solution N-methoxycarbonylmaleimide (0.2 g, 1.29×10$^{-3}$ mol) was added with vigorous stirring. After ten minutes water (10 mL) was added and the reaction left stirring for a further 45 minutes. The pH was then adjusted to 3 with 0.5N sulfuric acid and NaCl (0.30 g) was added. The polymer was then extracted in to dichloromethane (3×50 mL), the extracts were combined and dried over Na$_2$SO4 before being filtered and evaporated to dryness. The polymer was then washed with diethyl ether and dried under vacuum at room temperature. $^1$H NMR spectra shows appearance of the maleimide resonances at ~5.9-6.4 and ~6.7 ppm.

Conversion of Amine End Group of PolyPEG to Maleimide Group

Amine terminated poly(MPEG(550)MA) [Mn 3200](1.0 g, 3.13×10$^{-4}$ mol), saturated sodium hydrogen carbonate (5 mL) and a magnetic follower were placed into a three necked round bottom flask and cooled by placing in an ice bath. The system was flushed with nitrogen and placed under an inert atmosphere. To this solution N-methoxycarbonylmaleimide (0.20 g, 1.29×10$^{-3}$ mol) was added with vigorous stirring. After ten minutes water (10 mL) was added and the reaction left stirring for a further 45 minutes. The pH was then adjusted to 3 with 0.5N sulfuric acid and NaCl (3.75 g) was added. The polymer was then extracted in to dichloromethane (3×50 mL), the extracts were combined and dried over Na$_2$SO4 before being filtered and evaporated to dryness. The polymer was then washed with diethyl ether and dried under vacuum at room temperature. $^1$H NMR spectra shows appearance of the maleimide resonances at ~5.9-6.4 and ~6.7 ppm.

Conversion of Amine End Group of PolyPEG to Maleimide Group

Amine terminated poly(MPEG(2000)MA) [Mn 24600](5.0 g, 2.03×10$^{-4}$ mol), saturated sodium hydrogen carbonate (15 mL) and a magnetic follower were placed into a three necked round bottom flask and cooled by placing in an ice bath. The system was flushed with nitrogen and placed under an inert atmosphere. To this solution N-methoxycarbonylmaleimide (0.13 g, 8.13×10⁻⁴ mol) was added with vigorous stirring. After ten minutes water (15 mL) was added and the reaction left stirring for a further 45 minutes. The pH was then adjusted to 3 with 0.5N sulfuric acid and NaCl (7.5 g) was added. The polymer was then extracted in to dichloromethane (4×50 mL), the extracts were combined and dried over $Na_2SO4$ before being filtered and evaporated to dryness. The polymer was then washed with diethyl ether and dried under vacuum at room temperature. $^1H$ NMR spectra shows appearance of the maleimide resonances at ~5.9-6.4 and ~6.7 ppm.

Conversion of Amine End Group of PolyPEG to Maleimide Group

Amine terminated poly(MPEG(2000)MA) [Mn 24600 PDi 1.06](15.0 g, 6.1×10⁻⁴ mol), saturated sodium hydrogen carbonate (45 mL) and a magnetic follower were placed into a three necked round bottom flask and cooled by placing in an ice bath. The system was flushed with nitrogen and placed under an inert atmosphere. To this solution N-methoxycarbonylmaleimide (0.38 g, 2.44×10⁻³ mol) was added with vigorous stirring. After ten minutes water (15 mL) was added and the reaction left stirring for a further 45 minutes. The pH was then adjusted to 3 with 0.5N sulfuric acid and NaCl (7.5 g) was added. The polymer was then extracted in to dichloromethane (3×50 mL), the extracts were combined and dried over $Na_2SO4$ before being filtered and evaporated to dryness. The polymer was then washed with diethyl ether and dried under vacuum at room temperature before final purification through dialysis and isolation by freeze drying. $^1H$ NMR spectra shows appearance of the maleimide resonances at ~5.9-6.4 and ~6.7 ppm.

Coupling of Succinimide Terminated PolyPEG to Benzylamine

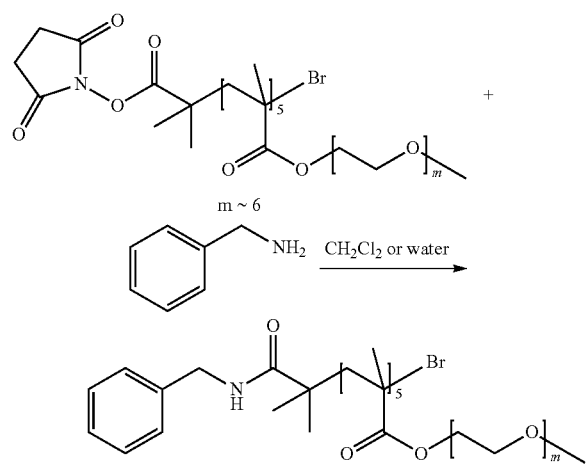

Two different experiments were carried out, each using a different solvent. Low molecular weight poly(MPEG(395)MA) (Mn=2700 g/mol, PDI=1.12) (1 g, 0.370×10⁻³ mol) prepared from initiator 7 (i.e. succinimide terminated) and benzylamine (0.40 ml, 3.7×10⁻³ mol) was dissolved in 10 ml of dry chloroform or distilled water and stirred at room temperature for 20 hours under nitrogen. After reaction, the solvent was removed under vacuum by using a rotary evaporator. The crude was purified by preparative GPC before being precipitated of the polymer in cold Petroleum Ether (40-60° C. Fraction).

Bioconjuction of Succinimide Terminated PolyPEG Polymer

A set of three experiments was carried out, each containing a different ratio polymer/lysozyme. Moreover each set of experiments was left to react for either 4 hours or 20 hours. Low molecular weight poly(MPEG(395)MA) prepared from initiator 7 (i.e. succinimide terminated) (Mn=2700 g/mol, PDI=1.12) (41.6 mg, 15.4×10⁻³ mol) for a ratio 5/1, (83.2 mg, 30.8×10⁻³ mol) for a ratio 10/1 and (249.5 mg, 92.4×10⁻³ mol) for a ratio 30/1 and lysozyme (50 mg, 3.08×10⁻³ mol) was dissolved in 10 ml of 200 mM phosphate buffer (pH=8) and stirred at 4° C. for 4 hours or 20 hours under nitrogen. The reaction was followed by HPLC in the case of a ratio polymer/lysozyme 30/1. The HPLC system was fitted with a guard column, a BioSep-SEC-S3000 column and a UV detector continuously measuring the relative absorbance of the mobile phase at 215 nm. The system was eluted with 0.1% v/v trifluoroacetic acid solution in water and acetonitrile (69/31 v/v) at a rate of 0.5 mL/min. In each case, the crude was purified in dialysis bag (Spectra/Porl, MWCO=6-8000 g/mol) and analysed by SDS-PAGE (polyacrylamide resolving gel cross-linking: 15%, running buffer: 25 mM TRIS base, 250 mM glycine, 0.1% SDS, pH 8.7).

Reactions of PolyPEG Polymers Prepared from Initiator 12

Conversion of Acetal End Group of PolyPEG to Aldehyde Group

Acetal-terminated polymer (Mn 11000, PDi 1.15, 3.0 g, 0.27 mmol) was dissolved in a 1:1 trifluoroacetic acid (TFA)/$H_2O$ solution (100 mL) and the solution was stirred at room temperature for 48 hours. Most of the acid was removed under reduced pressure and the crude was dissolved in water and purified by dialysis. The aqueous solution was then freeze-dried to give the desired aldehyde terminal polymer (2.8 g, 0.25 mmol, 93%) as an off-white solid. ($M_n$~11,000, PDi 1.13)

Conversion of Acetal End Group of PolyPEG to Aldehyde Group

Acetal-terminated polymer (Mn 22,000, PDi 1.09, 3.0 g, 0.14 mmol) was dissolved in a 1:1 trifluoroacetic acid (TFA)/$H_2O$ solution (100 mL) and the solution was stirred at room temperature for 48 hours. Most of the acid was removed under reduced pressure and the crude was dissolved in water and purified by dialysis. The aqueous solution was then freeze-dried to give the desired aldehyde terminal polymer (2.8 g, 1.3 mmol, 93%) as an off-white solid. ($M_n$~22,000, PDi 1.09)

Conversion of Acetal End Group of PolyPEG to Aldehyde Group

Acetal-terminated polymer (Mn=32,000, PDi=1.09, 3.0 g, 0.094 mmol) was dissolved in a 1:1 trifluoroacetic acid (TFA)/$H_2O$ solution (100 mL) and the solution was stirred at room temperature for 48 hours. Most of the acid was removed under reduced pressure and the crude was dissolved in water and purified by dialysis. The aqueous solution was then freeze-dried to give the desired aldehyde terminal polymer (2.7 g, 0.084 mmol, 90%) as an off-white solid. ($M_n$~32,000, PDi 1.11)

Bioconjugation of Deprotected PolyPEG Polymers Prepared from Initiator 12

Bioconjuction of Aldehyde-Terminated PolyPEG Polymer

Lysozyme (6 mg, $4.2 \times 10^{-4}$ mmol) and aldehyde-terminated polymer ($M_n$~22,000, PDi 1.09, 110 mg, 0.01 mmol) was dissolved in 5 mL of acetate/acetic acid buffer (pH=5) and 0.15 mL of NaCNBH$_3$ (0.25 mM in water) was added dropwise. The solution was stirred at room temperature and samples were taken at regular intervals. The reaction was monitored by HPLC fitted with a guard column, a bioSep-SEC-S3000 column and an UV detector.

Bioconjuction of Aldehyde-Terminated PolyPEG Polymer

Lysozyme (6 mg, $4.2 \times 10^{-4}$ mmol) and aldehyde terminated polymer ($M_n$~22,000, PDi 1.09, 110 mg, 0.01 mmol) was dissolved in 5 mL of phosphate buffer (pH=6) and 0.15 mL of NaCNBH$_3$ (0.25 mM solution in water) was added dropwise. The solution was stirred at room temperature and samples were taken at regular intervals. The reaction was monitored by HPLC fitted with a guard column, a bioSep-SEC-S3000 column and an UV detector.

Reactions of PolyPEG Polymers Prepared from Initiator 14

Conversion of BOC End Group of PolyPEG to Amine Group

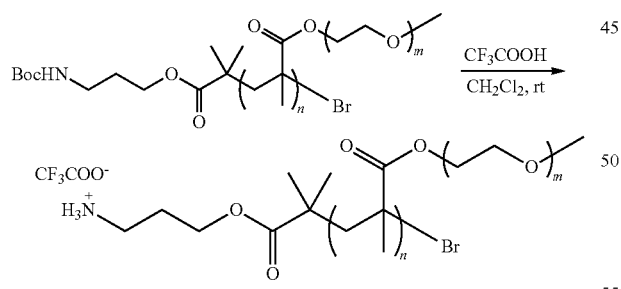

BOC terminated polymer ($M_n$=6400 g mol$^{-1}$, 3.2 g, 1.0 mmol) was dissolved in CH$_2$Cl$_2$ (25 mL), trifluoroacetic acid (3.9 mL, 50 mmol) was added via syringe and the resulting solution was stirred at room temperature for 16 h. The solvent was then removed under reduced pressure and the resulting orange-brown oil was dissolved in deionized water and dialyzed. The polymer solution was freeze-dried. Toluene (50 mL) was then added and the solvent was removed under reduced pressure. This procedure was repeated three times and the expected amine terminated polymer as the trifluoroacetic acid salt (2.5 g, 0.81 mmol, 81% yield) was obtained as a yellow-orange oil. $^1$H NMR revealed the complete disappearance of the singlet relative to the Boc group at 1.4 ppm. $M_w/M_n$ (GPC)=1.11

Conversion of Amine End Group of PolyPEG to Malemide Group

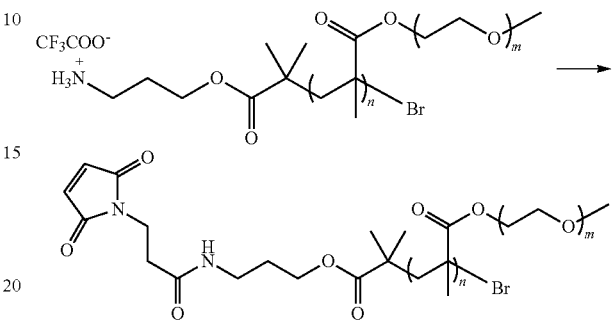

3-Maleimidepropionyl chloride (13.0 mmol) was dissolved in 100 mL of CH$_2$Cl$_2$, diisopropylethylamine (DIPEA, 2.3 ml, 13.0 mmol) was added via syringe and the solution was cooled to 0° C. A solution of amine terminated polymer as the trifluoracetic acid salt (1.5 g, 0.47 mmol) in 30 mL of CH$_2$Cl$_2$ was added dropwise (ca. 15 min) and the mixture was stirred at 0° C. for 1 h, then at room temperature for 2 days. The solvent was then removed under reduced pressure and 200 mL of water were added to the brown residue. The suspension was centrifugate and purified by dialysis (Millipore, regenerated cellulose, MWCO 1 kDa, filtration area 0.23 m$^2$).

The polymer solution was freeze-dried. Toluene (50 mL) was then added and the solvent was removed under reduced pressure. This procedure was repeated three times and the expected malemide terminated polymer was obtained as a pale yellow oil. A conversion of 80% can be calculated by $^1$H NMR, comparing the integration of the vinylic protons of the maleimide moiety and that of the terminal OCH$_3$ of the PEG side-chains. Mw/Mn (GPC)=1.06.

Reactions of PolyPEG Polymers Prepared from Initiator 15

Conversion of Furan End Group of PolyPEG to malemide Group

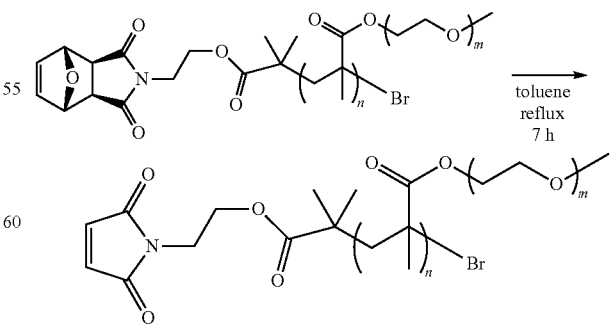

A solution of polymer prepared from initiator 15 (3.0 g, 0.36 mmol) in toluene (25 mL) was warmed to reflux and the reaction was monitored by $^1$H NMR analysis on samples taken at regular intervals of time. After 7 h the solvent was removed under reduced pressure to give the maleimide terminated polymer as a pale orange oil. Comparison of the integration of the maleimide vinyl signals and the terminal OCH$_3$ of the PEG side-chains confirmed that the maleimide function did not decompose during the deprotection step.

References

1. D. M. Haddleton, M. C. Crossman, B. H. Dane, D. J. Duncalf, A. M. Henning, D. Kukulj and A. J. Shooter, *Macromolecules*, 1999, 32, 2110.
2. R. N. Keller and W. D. Wycoff, *Inorg. Synth.*, 1947, 2, 1.
3. James R. Dudley, Jack T. Thurston, Frederic C. Schaefer, Dagfrid Holm-Hansen, Clarence J. Hull, and Pierrepont Adams, *J. Am. Chem. Soc.*, 1951, 73, 2986.

The invention claimed is:

1. A comb polymer having the general formula:

A-(D)$_d$-(E)$_e$-(F)$_f$ where:
    A is a moiety capable of covalently binding to a protein or a polypeptide, provided that A is not a hydroxyl group;
    (D)$_d$ is a polymeric unit produced by polymerizing a plurality of monomer molecules selected from one or more olefinically unsaturated monomers by addition polymerization, wherein said monomers are not the monomers used to produce (E)$_e$;
    (E)$_e$ is a polymeric unit comprising an alkoxy polyether, said polymeric unit produced by polymerizing by addition polymerization a plurality of monomer molecules which are linear, branched, or star-shaped, substituted or non-substituted and have an olefinically unsaturated moiety;
    (F)$_f$ is a polymeric unit produced by polymerizing by addition polymerization a plurality of monomer molecules selected from one or more olefinically unsaturated monomers which are not as defined in E;
    d and f are each independently an integer between 0 and 500; and
    e is an integer of 10 to 1000.

2. A comb polymer according to claim 1, wherein (E)$_e$ comprises a poly(alkylene glycol) or polytetrahydrofuran.

3. The comb polymer according to claim 2, wherein the poly(alkylene glycol) is poly(ethylene glycol) (PEG) or poly(propylene glycol).

4. A comb polymer according to claim 1, having a number average molecular weight of 2,000 to 80,000.

5. The comb polymer according to claim 1, wherein the monomers which are polymerized to produce each of (D)$_d$, (E)$_e$, and (F)$_f$ comprise an olefinically unsaturated group independently selected from acrylate, methacrylate, methylmethacrylate, styrene, methylacrylate and diene.

6. The comb polymer according to claim 1, wherein the moiety capable of binding to the protein or the polypeptide comprises succinimidyl succinate, N-hydroxysuccinimide, succinimidyl propionate, succinimidyl butanoate, triazine, vinyl sulfone, propionaldehyde, acetaldehyde, tresylate, benzotriazole carbonate, maleimide, pyridyl sulfide, iodoacetamide or succinimidyl carbonate.

7. A comb polymer according to claim 1, wherein the moiety which is capable of reacting with the protein or the polypeptide comprises:

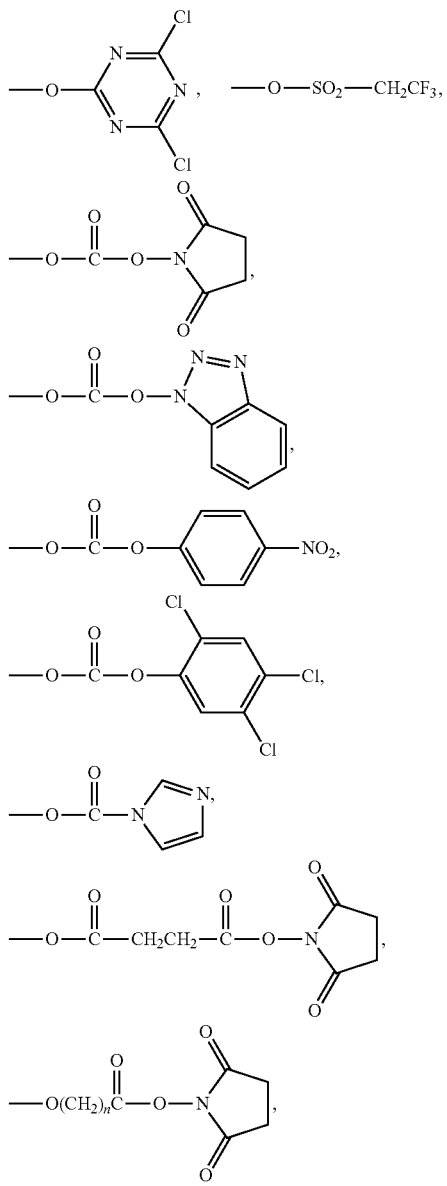

where n = integer of 0 to 10;

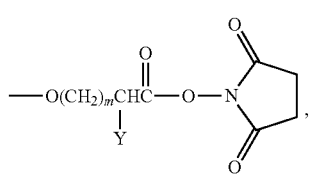

where m = integer of 0 to 10, Y is an aliphatic or aromatic moiety;

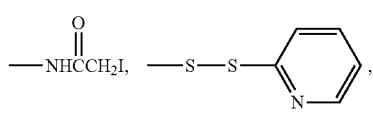

-continued

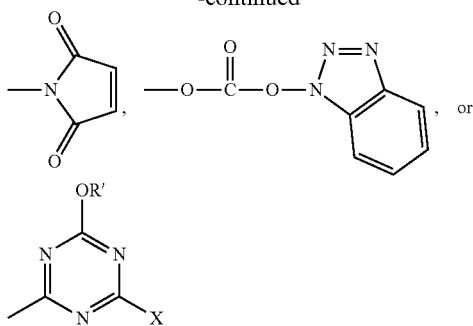

where R' is H, methyl, ethyl, propyl or butyl, and X =halide.

8. The comb polymer according to claim 1 comprising a fluorescent label.

9. The comb polymer according to claim 8, wherein the fluorescent label is a coumarin.

10. A polymer-biomolecule conjugate produced by a method comprising the step of reacting a protein or a polypeptide with the comb polymer of claim 1, thereby forming the polymer-biomolecule conjugate.

11. The polymer-biomolecule conjugate of claim 10, which is biologically-active.

12. The polymer-biomolecule conjugate according to claim 10, which is a drug.

13. A pharmaceutical composition comprising the polymer-biomolecule conjugate of claim 10 and a pharmaceutically acceptable carrier.

14. A comb polymer produced by a method comprising the steps of:
   (a) providing:
      (i) a plurality of monomers which are linear, branched or star-shaped, substituted or non-substituted, and have an olefinically unsaturated moiety, the olefinically unsaturated moiety being capable of undergoing addition polymerization, wherein the monomers comprise alkoxy polyethers;
      (ii) an initiator compound; the initiator compound comprising a homolytically cleavable bond, wherein said initiator compound comprises a moiety which when attached to the comb polymer is capable of binding to a protein, polypeptide, carbohydrate, fat or nucleic acid, wherein said moiety is optionally protected, provided that the initiator compound is not 2-hydroxyethyl-2'-bromopropionate; and
      (iii) a catalyst capable of catalyzing the polymerisation of the monomer; and
   (b) causing the catalyst to catalyse, in combination with the initiator, the polymerisation of a plurality of the monomers to produce the comb polymer; and
   (c) optionally deprotecting the moiety which when attached to the comb polymer is capable of binding to a protein, polypeptide, carbohydrate, fat or nucleic acid.

15. The comb polymer of claim 14, wherein the alkoxy polyether is poly(alkylene glycol) or polytetrahydrofuran.

16. The comb polymer of claim 14, wherein the olefinically unsaturated moiety is acrylate, methacrylate, methylmethacrylate, styrene, methylacrylate, or a diene.

17. The comb polymer of claim 14, wherein the initiator compound is selected from:

A-S—C(O)—R, A-S—C(S)—O—R, R-S—C(O)—A, R-S—C(S)—O—A, A-B—X,

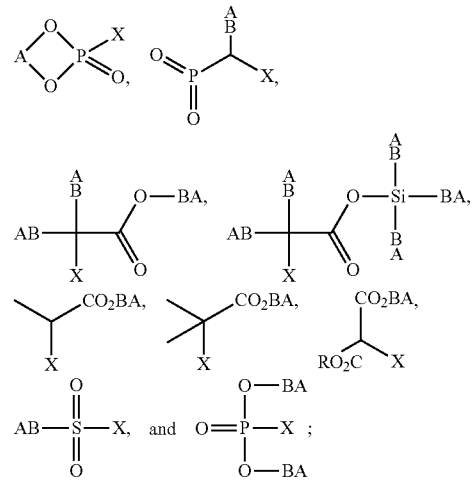

wherein X is a halide;

R is $C_1$ to $C_{20}$ substituted or non-substituted, straight chain, branched chain, cyclic, heterocyclic or aromatic alkyl;

A is an optionally protected moiety which, when attached to the comb polymer, is capable of binding to a protein or polypeptide; and B is a linker or a direct bond.

18. The comb polymer of claim 17, wherein A is selected from succinimidyl succinate, N-hydroxysuccinimide, succinimidyl propionate, succinimidyl butanoate, triazine, vinyl sulfone, propionaldehyde, acetaldehyde, tresylate, benzotriazole carbonate, maleimide, pyridyl sulfide, iodoacetamide and succinimidyl carbonate.

19. The comb polymer of claim 14, wherein the initiator compound is selected from the group consisting of:

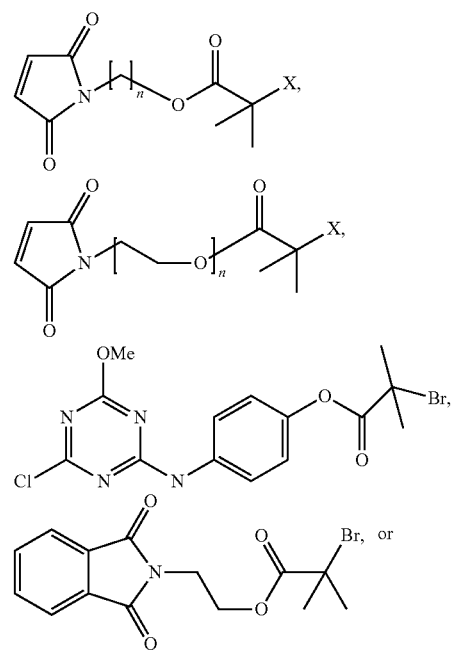

93
-continued
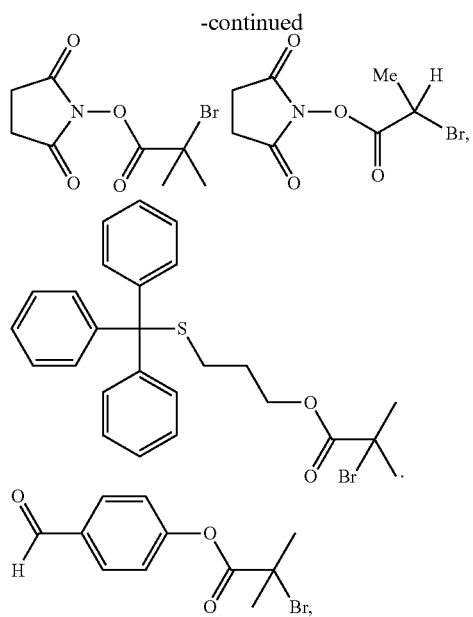
94
-continued
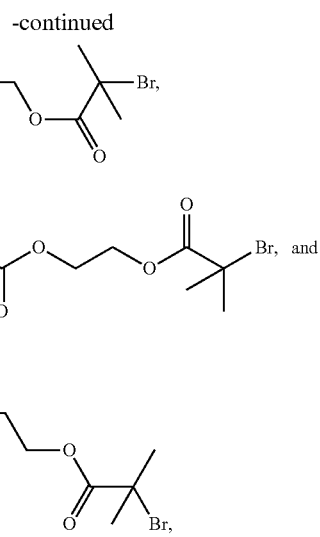
where n is an integer of 0 to 10, and X is a halide.
* * * * *